United States Patent
Kaleal, III

(10) Patent No.: US 12,176,102 B2
(45) Date of Patent: *Dec. 24, 2024

(54) PERSONALIZED AVATAR RESPONSIVE TO USER PHYSICAL STATE AND CONTEXT

(71) Applicant: KC HOLDINGS I, Mayfield Village, OH (US)

(72) Inventor: Robert Louis Kaleal, III, Mayfield Village, OH (US)

(73) Assignee: KC HOLDINGS I, Mayfield Village, OH (US)

( * ) Notice: Subject to any disclaimer, the term of this patent is extended or adjusted under 35 U.S.C. 154(b) by 49 days.

This patent is subject to a terminal disclaimer.

(21) Appl. No.: 17/806,124

(22) Filed: Jun. 9, 2022

(65) Prior Publication Data

US 2022/0319692 A1 Oct. 6, 2022

Related U.S. Application Data

(63) Continuation of application No. 17/389,047, filed on Jul. 29, 2021, now Pat. No. 11,990,233, which is a
(Continued)

(51) Int. Cl.
*A61B 5/20* (2006.01)
*A61B 5/00* (2006.01)
(Continued)

(52) U.S. Cl.
CPC ......... *G16H 40/63* (2018.01); *A61B 5/0205* (2013.01); *A61B 5/02055* (2013.01); *A61B 5/11* (2013.01);
(Continued)

(58) Field of Classification Search
CPC ....... A61B 5/0002; A61B 5/0022; A61B 5/01; A61B 5/0205; A61B 5/08; A61B 5/1116;
(Continued)

(56) References Cited

U.S. PATENT DOCUMENTS 8,612,363 B2 12/2013 Karkanias et al.
9,199,122 B2 12/2015 Kaleal et al.
(Continued)

OTHER PUBLICATIONS

Non-Final Office Action received for U.S. Appl. No. 17/389,047 dated Apr. 6, 2023, 52 pages.
(Continued)

*Primary Examiner* — Rex R Holmes
(74) *Attorney, Agent, or Firm* — Amin, Turocy & Watson, LLP

(57) ABSTRACT

Systems and methods are disclosed that facilitate providing guidance to a user during performance of a program or routine using a personalized avatar. In an aspect, a system includes a reception component configured to receive biochemical information about a physiological state or condition of a user, including information identifying a presence or a status of one or more biomarkers. The system further includes an analysis component configured to determine or infer one or more characteristics of the physiological state or condition of the user based on the information identifying the presence or the status of the one or more biomarkers, and a visualization component configured to adapt an appearance of an avatar presented to the user based on the one or more characteristics to reflect the one or more characteristics.

20 Claims, 21 Drawing Sheets

Related U.S. Application Data continuation of application No. 15/978,625, filed on May 14, 2018, now Pat. No. 11,107,579, which is a continuation of application No. 15/474,111, filed on Mar. 30, 2017, now Pat. No. 9,997,082, which is a continuation of application No. 14/945,600, filed on Nov. 19, 2015, now Pat. No. 9,652,992, which is a continuation-in-part of application No. 14/518,844, filed on Oct. 20, 2014, now Pat. No. 9,501,942, which is a continuation-in-part of application No. 14/049,981, filed on Oct. 9, 2013, now Pat. No. 9,198,622.

(60) Provisional application No. 61/711,510, filed on Oct. 9, 2012.

(51) Int. Cl.

| | | |
|---|---|---|
| *A61B 5/0205* | (2006.01) | |
| *A61B 5/11* | (2006.01) | |
| *A61B 5/16* | (2006.01) | |
| *G06F 1/16* | (2006.01) | |
| *G06Q 10/0639* | (2023.01) | |
| *G06Q 10/10* | (2023.01) | |
| *G06Q 50/00* | (2012.01) | |
| *G06T 13/40* | (2011.01) | |
| *G06T 19/00* | (2011.01) | |
| *G09B 5/02* | (2006.01) | |
| *G09B 5/06* | (2006.01) | |
| *G09B 19/00* | (2006.01) | |
| *G16H 20/40* | (2018.01) | |
| *G16H 20/70* | (2018.01) | |
| *G16H 40/63* | (2018.01) | |
| *A61B 5/08* | (2006.01) | |

(52) U.S. Cl.
CPC ................ *A61B 5/165* (2013.01); *A61B 5/20* (2013.01); *A61B 5/40* (2013.01); *A61B 5/41* (2013.01); *A61B 5/42* (2013.01); *A61B 5/43* (2013.01); *A61B 5/45* (2013.01); *A61B 5/486* (2013.01); *A61B 5/7264* (2013.01); *A61B 5/744* (2013.01); *A61B 5/7445* (2013.01); *G06F 1/1626* (2013.01); *G06Q 10/0639* (2013.01); *G06Q 10/10* (2013.01); *G06Q 50/01* (2013.01); *G06T 13/40* (2013.01); *G06T 19/00* (2013.01); *G09B 5/02* (2013.01); *G09B 5/06* (2013.01); *G09B 19/00* (2013.01); *G09B 19/0092* (2013.01); *G16H 20/40* (2018.01); *G16H 20/70* (2018.01); *A61B 5/08* (2013.01); *A61B 5/44* (2013.01); *A61B 5/7246* (2013.01); *G06T 2219/2012* (2013.01)

(58) Field of Classification Search
CPC ....... A61B 5/1118; A61B 5/743; A61B 5/744; A61B 5/7475
See application file for complete search history.

(56) References Cited

U.S. PATENT DOCUMENTS

| | | | |
|---|---|---|---|
| 9,409,051 B2* | 8/2016 | Kaleal, III | ............ A61B 5/4866 |
| 9,913,618 B2* | 3/2018 | Kaleal, III | ............ A61B 5/0816 |
| 9,997,082 B2* | 6/2018 | Kaleal | ...................... A61B 5/20 |
| 10,390,769 B2* | 8/2019 | Kaleal, III | ............. A61B 5/021 |
| 11,107,579 B2 | 8/2021 | Kaleal, III | |
| 2004/0002634 A1 | 1/2004 | Nihtila | |
| 2004/0131227 A1 | 7/2004 | Bravomalo et al. | |
| 2009/0047644 A1 | 2/2009 | Mensah et al. | |
| 2010/0207877 A1 | 8/2010 | Woodard | |
| 2010/0240458 A1 | 9/2010 | Gaiba et al. | |
| 2011/0021317 A1 | 1/2011 | Lanfermann | |
| 2011/0082010 A1 | 4/2011 | Dyer et al. | |
| 2011/0212782 A1 | 9/2011 | Thompson et al. | |
| 2012/0071771 A1 | 3/2012 | Behar | |
| 2012/0095863 A1 | 4/2012 | Schiff et al. | |
| 2012/0127157 A1 | 5/2012 | Adler et al. | |
| 2012/0182431 A1 | 7/2012 | Asanov | |
| 2012/0183940 A1 | 7/2012 | Aragones et al. | |
| 2012/0271143 A1* | 10/2012 | Aragones | ................. G09B 5/02 600/595 |
| 2012/0290950 A1 | 11/2012 | Rapaport et al. | |
| 2013/0178960 A1 | 7/2013 | Sheehan et al. | |
| 2013/0252731 A1 | 9/2013 | Dugan et al. | |
| 2014/0188009 A1 | 7/2014 | Lange | |
| 2018/0344215 A1 | 12/2018 | Ohnemus et al. | |
| 2020/0211409 A1 | 7/2020 | Latorre et al. | |
| 2021/0248594 A1 | 8/2021 | Yantis et al. | |

OTHER PUBLICATIONS

Non-Final Office Action received for U.S. Appl. No. 17/806,117 dated Oct. 25, 2023, 110 pages.
Final Office Action received for U.S. Appl. No. 17/389,047 dated Sep. 15, 2023, 54 pages.
Non-Final Office Action received for U.S. Appl. No. 17/806,120 dated Nov. 8, 2023, 35 pages.
Parisi, Anthony, "EA Sports Active Review", http://www.1up.com/reviews/ea-sports-active, May 20, 2009, 3 pages.
Office Action for U.S. Appl. No. 14/049,981, dated Mar. 10, 2015, 17 pages.
Office Action for U.S. Appl. No. 14/518,808, dated Apr. 7, 2015, 22 pages.
Final Office Action for U.S. Appl. No. 14/049,981, dated Jun. 23, 2015, 18 pages.
Notice of Allowance for U.S. Appl. No. 14/049,981, dated Jul. 24, 2015, 18 pages.
Notice of Allowance for U.S. Appl. No. 14/518,808, dated Jul. 24, 2015, 20 pages.
Office Action for U.S. Appl. No. 14/593,603, dated Oct. 20, 2015, 27 pages.
Office Action for U.S. Appl. No. 14/593,603, dated Dec. 24, 2015, 15 pages.
Notice of Allowance for U.S. Appl. No. 14/593,603, dated Apr. 11, 2016, 19 pages.
Office Action for U.S. Appl. No. 14/945,600, dated May 4, 2016, 18 pages.
Office Action for U.S. Appl. No. 14/518,844, dated Oct. 19, 2015, 24 pages.
Office Action for U.S. Appl. No. 14/518,844, dated Dec. 22, 2015, 16 pages.
Office Action for U.S. Appl. No. 14/518,844, dated Apr. 4, 2016, 16 pages.
Office Action for U.S. Appl. No. 14/945,600, dated Oct. 14, 2016, 15 pages.
Office Action for U.S. Appl. No. 15/208,455, dated Oct. 18, 2016, 20 pages.
Notice of Allowance for U.S. Appl. No. 14/945,600, dated Jan. 11, 2017, 16 pages.
Final Office Action for U.S. Appl. No. 15/208,455, dated Mar. 15, 2017, 16 Pages.
Non-Final Office Action for U.S. Appl. No. 15/290,994, dated Feb. 6, 2017, 23 pages.
Final Office Action for U.S. Appl. No. 15/290,994 dated Jun. 1, 2017, 18 Pages.
Non-Final Office Action for U.S. Appl. No. 15/474,111, dated Jun. 13, 2017, 16 pages.
Non-Final Office Actionfor U.S. Appl. No. 15/208,455, dated Jun. 27, 2017, 18 pages.
Notice of Allowance for U.S. Appl. No. 15/208,455, dated Oct. 27, 2017, 32 pages.
Notice of Allowance for U.S. Appl. No. 15/290,994, dated Sep. 27, 2017, 15 pages.
Notice of Allowance for U.S. Appl. No. 15/474,111, dated Feb. 14, 2018, 19 pages.

(56) References Cited

OTHER PUBLICATIONS

Final Office Action for U.S. Appl. No. 15/474,111, dated Oct. 27, 2017, 19 pages.
Non-Final Office Action for U.S. Appl. No. 15/888,796, dated May 15, 2018, 26 pages.
Final Office Action for U.S. Appl. No. 15/888,796, dated Dec. 14, 2018, 10 pages.
Non-Final Office Action received for U.S. Appl. No. 15/978,625 dated Oct. 1, 2019, 29 pages.
Final Office Action received for U.S. Appl. No. 15/978,625 dated Jan. 30, 2020, 12 pages.
Non-Final Office Action received for U.S. Appl. No. 15/858,215 dated Nov. 25, 2019, 28 pages.
Non-Final Office Action received for U.S. Appl. No. 15/858,215 dated Jun. 5, 2020, 18 pages.
Non-Final Office Action received for U.S. Appl. No. 15/978,625 dated Apr. 9, 2020, 16 pages.
Final Office Action received for U.S. Appl. No. 15/858,215 dated Oct. 26, 2020, 16 pages.
Final Office Action received for U.S. Appl. No. 15/978,625 dated Aug. 25, 2020, 19 pages.
Non-Final Office Action received for U.S. Appl. No. 15/978,625 dated Jan. 4, 2021, 14 pages.
Non-Final Office Action received for U.S. Appl. No. 16/854,206 dated Dec. 8, 2021, 29 pages.
Final Office Action received for U.S. Appl. No. 16/854,206 dated Apr. 18, 2022, 33 pages.
Non-Final Office Action received for U.S. Appl. No. 17/938,595, dated Feb. 27, 2024, 40 pages.
Notice of Allowance received for U.S. Appl. No. 17/389,047, dated Jan. 17, 2024, 81 pages.
International Search Report and Written Opinion received for PCT Application Serial No. PCT/US22/42473 dated Jan. 25, 2023, 13 pages.
Final Office Action received for U.S. Appl. No. 17/806,117 dated Apr. 2, 2024, 193 pages.
Final Office Action received for U.S. Appl. No. 17/806,120 dated Apr. 16, 2024, 40 pages.
Notice of Allowance received for U.S. Appl. No. 17/806,117 dated Jul. 10, 2024, 26 pages.
Notice of Allowance received for U.S. Appl. No. 17/806,120 dated Aug. 2, 2024, 66 pages.
Notice of Allowance received for U.S. Appl. No. 17/938,595 dated Aug. 2, 2024, 47 pages.

\* cited by examiner

MY PROFILE
← 502

PERSONAL INFORMATION
Name         Primary care
Address      Emergency Contact
Contact info.

PHYSICAL PROFILE   LIMITATIONS
Age:     Resting BP:    ☐ Lower back  ☐ Neck    ☐ Weight
Height:  Resting HR:    ☐ Shoulders   ☐ Wrist   ☐ BP
Weight:  MBI:           ☐ Knees       ☐ Ankles  ☐ Other
List other injuries or conditions here

DIETARY RESTRICTIONS
☐ No Fat      ☐ High Chol.   ☐ No Dairy       ☐ No Carb     ☐ Weight
☐ Low Fat     ☐ Kosher       ☐ Lactose Int.   ☐ Low Carb
☐ Calorie R   ☐ Low Sodium   ☐ Vegan          ☐ Low Protein
☐ Low Chol.   ☐ No Sodium    ☐ Vegetarian     ☐ High Protein
List other dietary restrictions here

← 504

Lower back
wrist

Your next Health Risk Assessment is due by: January 22, 2015

FIG. 5

PERSONALIZED AVATAR RESPONSIVE TO USER PHYSICAL STATE AND CONTEXT

CROSS-REFERENCE TO RELATED APPLICATIONS

This application is a continuation of and claims priority to each of, U.S. patent application Ser. No. 17/389,047 filed on Jul. 29, 2021 and entitled "PERSONALIZED AVATAR RESPONSIVE TO USER PHYSICAL STATE AND CONTEXT," which is a continuation of U.S. patent application Ser. No. 15/978,625 filed on May 14, 2018 (now U.S. Pat. No. 11,107,579) and entitled "PERSONALIZED AVATAR RESPONSIVE TO USER PHYSICAL STATE AND CONTEXT," which is a continuation of U.S. patent application Ser. No. 15/474,111 filed on Mar. 30, 2017 (now U.S. Pat. No. 9,997,082) and entitled "PERSONALIZED AVATAR RESPONSIVE TO USER PHYSICAL STATE AND CONTEXT," which is a continuation of U.S. patent application Ser. No. 14/945,600, filed on Nov. 19, 2015 (now U.S. Pat. No. 9,652,992) and entitled "PERSONALIZED AVATAR RESPONSIVE TO USER PHYSICAL STATE AND CONTEXT," which is a continuation in-part of U.S. patent application Ser. No. 14/518,844, filed Oct. 20, 2014 (now U.S. Pat. No. 9,501,942) and entitled, "PERSONALIZED AVATAR RESPONSIVE TO USER PHYSICAL STATE AND CONTEXT," which is a continuation in part of U.S. patent application Ser. No. 14/049,981, filed on Oct. 9, 2013 (now U.S. Pat. No. 9,198,622) and entitled "VIRTUAL AVATAR USING BIOMETRIC FEEDBACK," which claims priority to U.S. Provisional Patent Application Ser. No. 61/711,510 filed on Oct. 9, 2012, and entitled "VIRTUAL AVATAR USING BIOMETRIC FEEDBACK." The entireties of the aforementioned applications are incorporated by reference herein.

TECHNICAL FIELD

This application generally relates to systems and methods for generating a personalized avatar that is responsive to a user's physical state and context.

BACKGROUND

The use of personal biometric monitoring equipment has increased the ability of individuals to more easily and more accurately collect, track and analyze data relating to the body's response to various triggers. For example, wearable sensors can monitor heart rate during an exercise program and collect and record the heart rate data for further analysis. In addition, wearable movement sensors including fine tuned accelerometers and gyroscopes combined with pattern analysis have enabled the detection and analysis of user motion. The symbiosis of user motion and biometric analysis facilitates an acute understanding of an individual's physiological responses to various types of events and triggers. As a result, various tools can be established that help to control, improve or accommodate an individual's physical and physiological activity.

BRIEF DESCRIPTION OF THE DRAWINGS

Numerous aspects, embodiments, objects and advantages of the present invention will be apparent upon consideration of the following detailed description, taken in conjunction with the accompanying drawings, in which like reference characters refer to like parts throughout, and in which:

FIG. 5 illustrates an example user interface that facilitates receiving user profile information in association with employment of an avatar guidance system for physical fitness purposes in accordance with various aspects and embodiments described herein;

DETAILED DESCRIPTION

I—Overview

Figure 1:
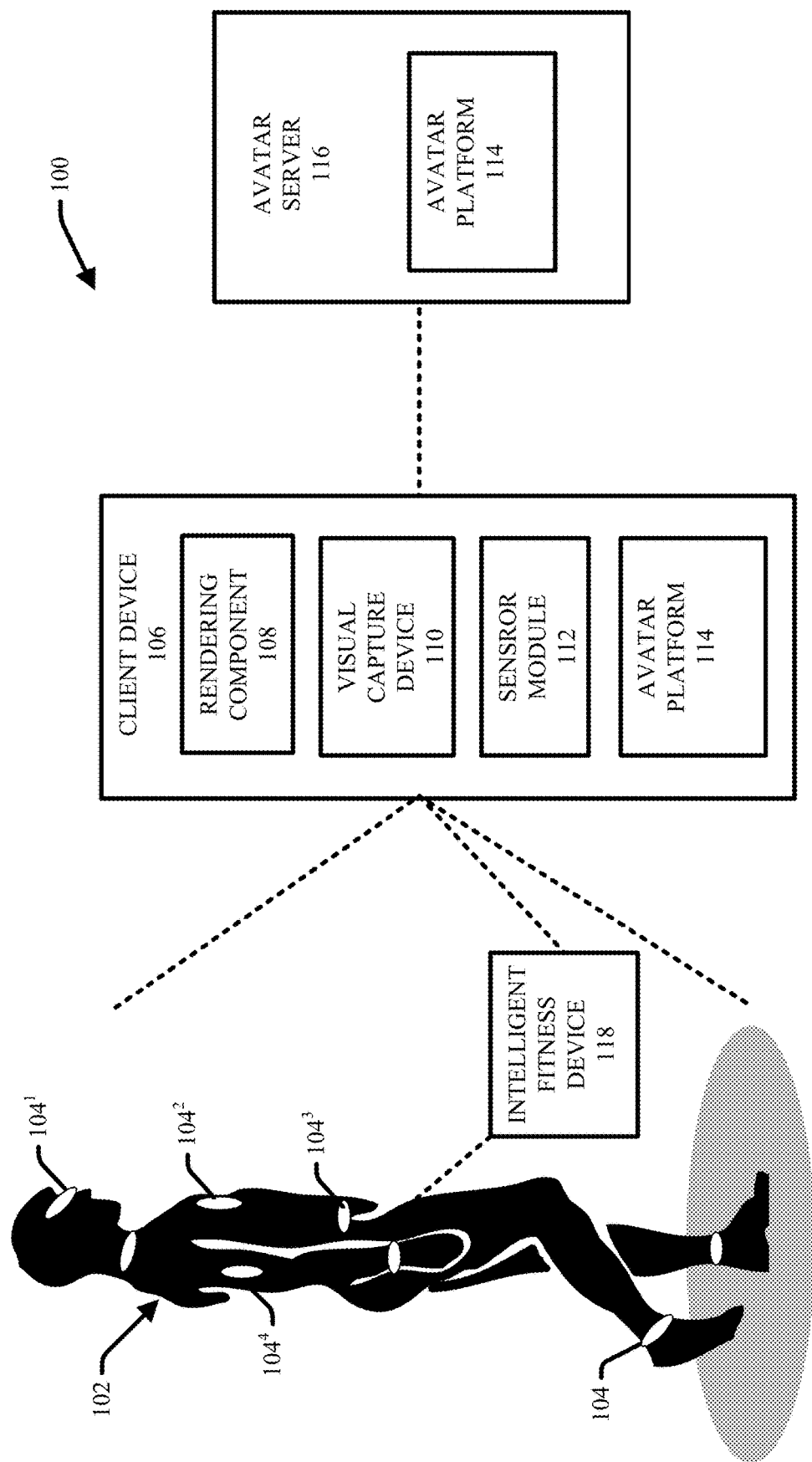
FIG. 1 illustrates an example system architecture for manifesting responses to physical and physiological activity information and image data about a user using a virtual avatar in accordance with various aspects and embodiments described herein.

The innovation is described with reference to the drawings, wherein like reference numerals are used to refer to like elements throughout. In the following description, for purposes of explanation, numerous specific details are set forth in order to provide a thorough understanding of this innovation. It may be evident, however, that the innovation can be practiced without these specific details. In other instances, well-known structures and components are shown in block diagram form in order to facilitate describing the innovation.

By way of introduction, the subject matter described in this disclosure relates to manifesting responses to physical and physiological activity information and image data about a user using a virtual avatar presented to the user. In computing technology, an avatar is a graphical representation of a character or personality provided to convey information to a viewer. An avatar can take a two or three-dimensional human form and be configured to speak and move as would a real person. The disclosed subject matter relates generally to using an avatar whose behavior and/or appearance changes based in part on received physical and physiological information and image data about a user.

In various embodiments, the physical and physiological information can include sensed physiological or biometric information about the user, motion data regarding movement of the user and image data corresponding to two or three dimensional image captures of the user. In an aspect, the physical and physiological information is captured via one or more biometric or motion sensors attached to the user. In another aspect, the physical and physiological activity data is captured via an image capture device (e.g., a camera, a video camera, a three-dimensional image capture device, a three-dimensional scanner, etc.). In another aspect, the physical and physiological activity data is captured via a remote sensing device employed by the user (e.g., an external medical monitoring device, a handheld sensing device, a remote, a balance pad, fitness device employed by the user, etc.).

For example depending on the types of biometric sensors employed, collected physiological data about a user can include but is not limited to information regarding the user's: heart rate, body temperature, respiration, perspiration, blood pressure, calories burned, body fat, and body weight. When biosensors are employed, other physiological data based on chemical body reactions can be determined, such as glucose levels, cortisol levels, blood alcohol levels, presence of drug residues, presence of pathogens, presence of bacteria, etc. In addition, depending on the number and sophistication of motion sensors employed, collected movement data can range from the detection of general movement pattern based motions such as walking, running, sitting, jumping, climbing, etc., to even minute bodily motions such as strokes of a finger or the blinking of an eye. Further, image data can be captured of a user to facilitate generation on two or three-dimensional representations of the user.

In various additional embodiments, the physiological information can also include biochemical information regarding a biochemical state of a user, including information identifying presence and/or status of one or more biomarkers. As used herein the term biomarker refers to a measurable substance that serves as an indicator of a biological state or condition of a living organism. Biomarkers are often measured and evaluated to examine normal biological processes, pathogenic processes, or pharmacologic responses to a therapeutic intervention. In accordance with various aspects of the subject disclosure, biomarker information is employed to identify characteristics about a user's physiological state that can facilitate developing a health and fitness program for a user as well as, monitoring the user's adherence to the health and fitness program, evaluating a user's response to the health and fitness program, and guiding or coaching the user throughout performance of the health and fitness program.

For example, biomarker information can be used to determine a user's ability to perform various physical exercises, to evaluate a user's response to dietary and physical stimulus, and to determine physical and dietary actions for the user to perform in order to achieve the goals of the health and fitness program. For instance, biomarkers that can facilitate the various health and fitness related agendas above can include but are not limited to: folic acid, glucose, calcium, magnesium, creatine kinase, vitamin B12, vitamin D, ferritin, total cholesterol, hemoglobin, high density lipoprotein (HDL), low density lipoprotein (LDL), and triglycerides.

The biochemical information can be determined and received from various sources. In an aspect, the biochemical information is determined via testing analytes present in a user's blood, saliva, urine, tear fluid, sweat, or other suitable biological substance. In other aspects, the biochemical information is determined via sensors configured to detect electrical responses (e.g., a defibrillator) of the body or via spectroscopic analysis devices. The biochemical information can be received as input from a user, a medical professional, directly from laboratory systems, or directly from a biosensing device. In some aspects, the biosensing device is worn by the user (e.g., externally or an as implanted device) and be configured to regularly provide biochemical information about the user (e.g., in real time).

In accordance with an embodiment, an avatar guidance system is provided that analyzes received physical and physiological data about a user to evaluate adherence of the user to predefined routine or program. In response to analysis of received physical and physiological data for a user, visual changes and/or verbal commands for manifestation by an avatar presented to the user are determined and effectuated. In particular, an avatar presented to the user is configured to exhibit visual and/or audible behavioral reactions based on comparison of monitored data representing a metric of a user's physiology and/or physical movement with respect to one or more reference metrics associated with a routine or program the user has selected to follow. For example, in response to user physical and physiological activity data falling outside a predefined range for a specific user behavior associated with performance of an action, task or routine, in order to correct the behavior of the user, the avatar can react in a way designed to reflect model techniques and behavior.

Visual and verbal avatar reactions can embody those which a real human may perform and can include but are not limited to changes in: motion or movement, speech, tone of voice, level of sound/loudness, facial expressions, body language, color, speed of movement, and range of motion. In an aspect, responses to user physical and physiological activity data manifested by a virtual avatar as described herein are determined and effectuated in real-time (e.g., in response to receipt of the physical and physiological activity data). For example, a graphical user interface can be presented to the user that dynamically generates the avatar performing or exhibiting the determined responses. In another aspect, the avatar is rendered and presented to the user in the form of a three dimensional hologram.

Existing systems, such as various gaming programs, have employed avatars to mimic user motion data. For example, in response to a sensed jumping motion by a user, an avatar presented to the user may perform the jumping motion. However, rather than simply mimicking user motion, in accordance with various aspect of the disclosed avatar guidance system, an avatar is configured to respond to a user based on evaluation of the user's physical and physiological activity data with respect to a personalized program developed for the user that the user strives to follow. In particular, the avatar is configured to function as an intelligent being that has been specifically trained to observe, analyze and respond to a user's physical and physiological activity data based on a set of parameters defining at least one of: how the user should and shouldn't move, how the user's physiology should and shouldn't function, what actions or activities the user should and shouldn't perform, when the user should and shouldn't perform certain actions or activities, or how the user should and shouldn't appear. This set of parameters can be specifically tailored to govern user behavior with respect to a predetermined action, task or program.

For example, when performing a fitness routine that is associated with known or model/reference movement and physiological parameters for performance of the fitness routine by a model user, information can be collected about the user regarding the user's movement and physiology. The user's collected information is then compared to the known movement and physiological parameters to determine whether the user is adhering to the routine from an anatomical physical movement perspective and a physiological perspective. In response to a determination that the user's physical and physiological activity data deviates or does not deviate from the known movement and physiological parameters, a response is determined that is capable of being manifested by an avatar presented to the user. This response can provide the user with guidance to facilitate adherence to the fitness routine.

For instance, a response can include a determined physical action for the user to perform to correct the deviation and this physical action can be demonstrated by the avatar. As one example, if a monitored user on a treadmill is slowing down when a routine followed by the user does not call for slowing down, an avatar configured to guide or coach the user can change behavior to demonstrate a faster pace, thereby encouraging the user to speed up. The avatar can also provide verbal instructions regarding performance of the physical action.

In another example, in response to a determination that the user's physical and physiological activity data deviates or does not deviate from the model or reference movement and physical parameters for the fitness routine, a response can be determined for manifestation by the avatar that provides criticism, motivation, praise, comparison, or further instruction. This response can encompass movement by the avatar, speech, facial expression, tone of voice, or any other real life physical human reaction that could be envisioned to facilitate expression of criticism, motivation, praise, etc. In this way, as a user performs a fitness routine, program, action or task, the user can feel as though a real person was observing the user in real-time and responding in the form of personal intelligent coach that is an expert in evaluating and guiding performance of the specific routine, program, action or task.

In addition to comparison of received user physical and physiological activity data to reference physical metrics for a specific routine, program, action or task, various aspects of the disclosed avatar guidance system provide for personalized analysis of user physical and physiological activity data and personalized responses based on the analysis for manifested by an avatar. In one aspect, the reference physical and physiological activity metrics for the specific routine, program, action or task that is monitored for a user can be tailored or calibrated to fit the user's personal physical capabilities, functions and goals. For example, in furtherance to the physical fitness routine example, metrics for a user's range of motion, motion speed, heart rate, blood pressure, etc., can be tailored and calibrated to fit the user's personal goals and account for the user's physical capabilities.

Further, responses to adherence or deviation from a routine, program, task or action (e.g., based on comparison to reference metrics or personally calibrated reference metrics) for manifestation by an avatar can be tailored based on user preferences, demographics, mood, language, location, or context. For example, with respect to an avatar that functions as a user's fitness trainer, an individual may provide preferences that note what type of exercises the user likes and doesn't like to perform or what type of coaching motivates the user (e.g., soft encouraging technique over a more pushy demeaning approach). A response determined for the avatar to perform can then be tailored to account for the user's preferences. For instance, when the user is not achieving a particular exercise included in the fitness routine, the avatar can provide assurances that the user is "doing his best and that is all that matters," as opposed to harping at the user and pushing the user "to get it right or get ten more minutes of abdominal work at the end of the session." In another example, an avatar that is configured to provide instruction to a child can use different language and instructional techniques than an avatar configured to provide instruction to an adult. In yet another example, an avatar that is configured to provide guidance to a user throughout the day to adhere to a diet plan can suggest food options based on the user's context including the user's location, schedule and time of day.

Moreover, responses determined for manifestation by an avatar (based on received user physical and physiological activity data) to provide a user with guidance, instruction or support with respect to performing an action, program, task or routine can be based on learned user behavior. For example, historical data regarding past reactions/responses performed by the user to avatar responses in association with same or similar routines, tasks or actions can be collected and analyzed using various machine learning techniques to determine what types of avatar responses work and don't work for the user. In another example, traits, habits and abilities of the user can be learned over time and employed to tailor avatar responses. For instance, when suggesting a new exercise to transition to when a user is not achieving a previously suggested exercise, the avatar can select an exercise that the user is known to perform well to boost the user's spirit. In another example, when a user is known to stop at a fast food restaurant on Elm street when experiencing high stress levels on the way home from work, an avatar designed to help the user adhere to a diet program can warn the user that the user is likely to perform this mistake and suggest an alternate route and food option for the user.

The subject techniques for providing a user with guidance, instruction or support with respect to performing an action, program, task or routine via a virtual avatar based in part on monitored user physical and physiological activity data can have a variety of applications. In one aspect, the disclosed techniques are tailored to facilitate guiding a user through a physical fitness routine or program, such as a personal training session, a physical therapy program or any other physical activity that may require an instructor, coach, teacher, therapist, trainer, etc. Some examples are ergonometrics, dancing, yoga, zumba, and martial arts. For fitness applications, an avatar can play the role of a virtual instructor, coach, teacher, physical therapist, or personal trainer. During performance of a fitness routine, a user's physiological and movement data is collected and compared to reference physical and physiological activity metrics know for the specific fitness routine in view of personal information for the user (e.g., health restrictions, preferences, goals, etc.) to determine whether an avatar response is warranted and if so, what the avatar response should be (e.g., a specific verbal and/or visual command). After an avatar response is determined, the avatar displayed to the user performs the response.

In another aspect, the disclosed techniques can facilitate guiding a user with adherence to a diet program, a health program, a stress reduction program, a schedule and virtually any type of program that can be monitored and adapted based at least in part on physiological characteristics/changes of the user and/or movement/motion of the user. Regardless of the application of the disclosed avatar guidance system, by employing a virtual avatar, instruction and information provided to guide or coach a user through a task or program is presented to the user by virtual human exhibiting real life human visual and audible responses in the manner in which a personalized coach, therapist, assistant, friend, expert, doctor, etc. with particular insight about the user would respond. Accordingly, the user will feel as though a real person was by his or her side every step of the way throughout the program or activity the user is striving to perform. In addition, this 'real person' embodied via an avatar will be an expert at evaluating not only adherence to a specific program at hand, but a personalized guide that knows just how to tailor evaluation of adherence to the specific program for the user and how to tailor responses based on the evaluation to facilitate the user's adherence to the specific program at hand.

In accordance with another embodiment, systems and techniques are disclosed that provide for visualizing physical changes in a user based on performance or predicted performance of a fitness or diet program. In particular, an avatar visualization system is provided that is configured to receive or generate a visual replica of a user as the user currently appears. This visual replica can be embodied as an avatar presented to the user. As the user's appearance changes over the course of performance of a health and fitness program, the appearance of the avatar can also change to provide a mirrored visualization of the changes in the user. For example, each new day of the program, the appearance of the user can be evaluated, captured and imparted to the avatar. Thus in essence, the user's avatar can resemble a mirror image of himself over the course of a program.

The avatar visualization system is further configured to generate a visual representation of the user that is a prediction of how the user will appear at a future point in time based on performance of a health and fitness program by the user. In particular, the avatar visualization system can generate a visual representation or replica (e.g., an avatar) of a user based on currently received appearance information for the user, currently received physical and physiological activity data for the user (e.g., physiological data and/or movement data), and known health information for the user (e.g., physical measurements, physical conditions, physical capabilities, etc.). For example, the user can select, (and/or design, or otherwise be assigned) a specific health and fitness program for performance. The user can further be provided with a visual representation that demonstrates how the user will predicatively look after performance/completion of the program if the user adheres to the requirements of the program. In addition, the user can select various time points in the program (e.g., after week 1, after week 2, after week 3, etc.) and the avatar visualization system can generate a visual representation of the user that demonstrates how the user will predicatively look at the respective time points if the user adheres to the requirements of the program.

This avatar visualization system allows a user to dynamically pick and choose different health and fitness programs and/or change different variables of a health and fitness program and see how the user would appear in the future based on the selected health and fitness program and/or the different variables. Accordingly, a user can select a health and fitness program that will cause the user to achieve an optimally desired appearance. For example, as the user selects different health and fitness programs and/or can changes variables of a selected health and fitness program, the avatar visualization system can dynamically adapt the appearance of an avatar presented to the user that corresponds to a predicted visualization of how the user will appear based on completion and adherence to the different health and fitness or the health and fitness program with the respectively chosen variables. As a result, the user can select a specific health and fitness program based on how it will affect the user's appearance.

II—System Architecture

Referring now to the drawings, with reference initially to FIG. 1, presented is a diagram of an example architecture 100 for systems that facilitates manifesting responses to physical and physiological activity data about a user using a virtual avatar in accordance with various aspects and embodiments described herein. System architecture 100 can be employed in association with the disclosed avatar guidance system 200 discussed in Section III and the disclosed avatar visualization systems 1300 and 1400 discussed in section IV. Aspects of systems, apparatuses or processes explained in this disclosure can constitute machine-executable components embodied within machine(s), e.g., embodied in one or more computer readable mediums (or media) associated with one or more machines. Such components, when executed by the one or more machines, e.g., computer(s), computing device(s), virtual machine(s), etc. can cause the machine(s) to perform the operations described.

System 100 includes a person/user 102 and a client device 106 configured to receive and/or capture physical and physiological activity data (e.g., physiological/biometric data, motion data, image data, etc.) about the user 102. In an aspect, one or more sensor devices 104 can be worn or otherwise attached to the user 102 to capture the physical and physiological data and transmit the captured physical and physiological activity data to client device 106 (e.g., in real-time or substantially real-time). For example, the one or more sensor devices 104 can include biometric sensors configured to detect information regarding at least one of: heart rate (e.g., via a heart monitor device), body temperature (e.g., via a thermometer), respiration, perspiration, blood pressure, electrical activity of the heart or brain, calories burned, or body fat and body weight. In another example, the one or more sensor devices 104 can include biosensors configured to detect an array of additional biomarkers for a user, including but not limited information regarding: folic acid, calcium, magnesium, creatine kinase, vitamin B12, vitamin D, ferritin, total cholesterol, hemoglobin, HDL, LDL, triglycerides, fatty acids, insulin, hemoglobin, hormones (e.g., thyroid hormones (thyroid-stimulating hormone (TSH), metabolic hormones, reproductive hormones, etc.), liver enzymes, electrolytes (e.g., sodium, potassium, chloride, etc.), platelets, white blood cells, red blood cells, iron, etc.

In an aspect, the one or more sensor devices 104 can include wearable and implanted medical devices/sensors configured to detect and wirelessly communicate a wide array of biometric information about the user 102 to client device 106. Such biosensing devices can provide for real-time diagnostic testing and reporting. For instance, the one or more sensor devices 104 can include blood-sampling sensors (e.g., as glucose meters), tissue-embedded sensors (e.g., pacemakers and defibrillators), ingestibles embedded in pills that dissolve, epidermal sensors (e.g., patches and digital tattoos), wearables embedded in clothing or accessories, and external sensors (e.g., blood-pressure cuffs and pulse oximeters).

For example, biosensor device $104^1$ can include a biosensing contact lens configured to be worn in the user's eye and sense/detect various biomarkers in tear fluid. The contact lens can further be configured to wirelessly transmit information regarding presence and/or concentration of the detected biomarkers to an external device (e.g., client device 106 and/or avatar server 116). In another example, biosensor device $104^2$ can include an implantable cardioverter-defibrillator (ICD) configured to perform conventional functions of an ICD as well as additional sensing of biomarkers in bodily fluids. In yet another example, biosensor device $104^3$ can include a urinary catheter configured to be worn by the user to facilitate urinary functions while also being configured to detect biomarkers in urine and wirelessly transmit information regarding the biomarkers to an external device.

In yet another example, biosensor device $104^4$ can include a blood-testing device that is implanted into the body (e.g., under the skin) or worn in the form of a patch and configured to detect biochemical information regarding at least one of: glucose level, cortisol level, potassium level, blood oxygen level, blood alcohol level, inflammation, nitric oxide level, drug levels/residues present in the body, pathogens present in the body, or bacteria present in the body. In another example, the biosensors can be configured to detect an array of additional biomarkers for the user, including but not limited information regarding: folic acid, calcium, magnesium, creatine kinase, vitamin B12, vitamin D, ferritin, total cholesterol, hemoglobin, HDL, LDL, triglycerides, fatty acids, insulin, hemoglobin, hormones (e.g., thyroid hormones (thyroid-stimulating hormone (TSH), metabolic hormones, reproductive hormones, etc.), liver enzymes, electrolytes (e.g., sodium, potassium, chloride, etc.), platelets, white blood cells, red blood cells, iron, etc. For example, the biosensor device $104^4$ can be implanted under the skin and analyze concentrations of substances in the blood. The implantable blood-testing device can further wirelessly transmit information regarding the tested substances to an external device (e.g., client device 106).

I should be appreciated that the above described biosensing devices are merely exemplary and that other existing and future implantable/wearable devices capable of detecting biometric (e.g., biochemical information) about a user and wirelessly transmitting the biometric to an external device (e.g., client device 106) are within the scope of the subject disclosure.

In addition to physiological/biometric data, sensor devices 104 can facilitate capture and reporting of user movement or motion corresponding to speed, direction, and orientation of the user a whole and/or individual body parts of the user. For example, the one or more sensor devices 104 can include motion sensors such as an accelerometer, a gyroscope or an inertial measurement unit (IMU). Thus captured motion data can include information identifying acceleration, rotation/orientation, and/or velocity of the motion sensor device 104 itself, facilitating determination of motion and movement data of the body and/or body parts to which the motion sensor are attached. For example, processing of raw motion data (e.g., by the senor itself or the device to which the raw motion data is communicated, such as client device 106 and/or avatar server 116) can include pattern analysis to determine or infer types of motion represented by the motion data and/or characteristics associated with the types of motion (e.g., intensity, duration, range, speed, etc.). For example, using pattern recognition, patterns in the motion data can be correlated to know patterns for different types of motion, such as walking, running, climbing, jumping, falling, cycling, turning, etc. Motions sensors such as accelerometers can also be used in detection for Parkinson's disease. Patients of Parkinson's disease are known to have involuntary shaking. For those having mild symptom, shaking might not be significant. Since an accelerometer is sensitive enough to detect even mild shaking, when it is placed on a patient's arm while he/she is intended to hold the arm in still, the accelerometer could report involuntary shaking.

In another aspect, physical and physiological activity data regarding movements/motions performed by user 102 can include information captured by an intelligent fitness device 118 employed by the user in association with performance of a fitness routine or exercise. For example, some fitness exercises can involve usage of fitness equipment, such as exercise machines (e.g., a treadmill, a bicycle, a rowing machine, a weight machine, a balance board, etc.) or accessories (e.g., free weights, weighted balls, hula hoops, yoga blocks, bands, etc.). In an aspect, this fitness equipment can include a sensor device(s) configured to track and record user movements and motions and report (e.g., via wireless or wired connections) these movements and motions to client device 106 (and/or avatar server 116). For example, sensors and monitoring devices included in a treadmill can track user speed and incline. In another example, sensors included in various weight machines or free weights can detect and report number of reps, intensity, weight used, range of motion etc. Still in yet another example, a balance board or pressure sensitive mat can detect user movement performed while standing on the matt based on pressure and weight distribution.

In some implementations, intelligent fitness device 118 can include an external biometric sensing device configured to capture biochemical information for a user. For example, intelligent fitness device 118 can include a pressure cuff or pulse oximeter device. In another example, intelligent fitness device 118 can include a handled spectroscopic device configured to employ spectroscopic techniques to detect various biomarkers when externally applied to a user's skin, including but not limited to, antioxidant biomarkers, cortisol, cytochrome c-Oxidase, cholesterol and blood alcohol.

In additional implementations, physical data about a user corresponding to movement/motion and appearance of the user 102 can be captured by client device 106. For example, client device 106 can include a visual capture device 110 such as a still image camera, a video camera, or a three dimensional camera/scanner configured to capture image and/or video data of the user 102. According to this example, client device 106 can collect video and still images of the user 102 as the user performs an activity, task, or routine (e.g., a workout routine). The image data can be analyzed using pattern recognition to determine whether the user's movement corresponds to model movement metrics for the activity, task or routine. For instance, while performing a fitness routine such as a yoga or dance routine, image data captured by visual capture device 110 can be processed and analyzed (e.g., in real-time) to determine whether the user is executing the correct movements/poses and using proper form.

In another aspect, image data for a user captured by visual capture device 110 can be analyzed to determine physical measurements metrics for the users, such as height, weight, body fat, dimension of the user's waist, hips, shoulders, biceps, etc. As a user's body changes over time (e.g., in response to performance of an exercise or diet program), changes to physical measurement parameters of the user can be tracked, recorded, and monitored. In addition, a visual replica (e.g., a two dimensional image or three dimensional image where a three dimensional imaging device is employed) of the user as the user actually appears (e.g., standing still or during performance of a fitness routine), should appear (e.g., based on a model) or may predicatively appear in response to advancement in a fitness/diet program, can also be generated. In an aspect, an avatar that is generated and presented to the user (e.g., via rendering component 108 and/or avatar platform 114) can be modeled to replicate the user's physical appearance based on the captured image data.

In another aspect, client device 106 can include a sensor module 112 that can aid with detection of user motion and motion data using infrared or visible light detection devices. In yet another aspect, client device 106 can include a wearable device and sensor module 112 can include biometric and/or motion sensors configured to capture the various physical and physiological activity metrics described with respect to sensor devices 104.

Client device 106 also includes rendering component 108 to generate and present an avatar to the user 102. For example, rendering component 108 can be configured to generate a graphical user interface that includes the avatar and rendered via a display screen of the client device 106. In another example, rendering component 108 can be configured to generate an avatar as a hologram that is presented to the user 102. In an aspect, an avatar generated/presented via rendering component 108 perform various visual and/or audible actions based at least in part on analysis of the physical and physiological activity data as described herein. In another aspect, an avatar generate/presented to the user via rendering component is configured to provide a visual replica of the user.

In an aspect, client device 106 can include avatar platform 114 to provide for processing and analyzing of user's physical and physiological activity data to facilitate determination and manifestation of avatar reactions and appearances to the data in accordance with aspects described herein. In another aspect, some or all of the processing and analysis of the physical and physiological activity data is performed by a remote avatar server 116. According to this aspect, avatar server 116 can include an avatar platform 114 and client device 106 can communicate received and/or captured physical and physiological activity data to the avatar server 116 for processing thereof. The avatar server 116 can further communicate control commands, determined based on the processed physical and physiological activity data, that control the various visual and/or audible actions of the avatar generated and displayed at client device 106 by rendering component 108. In another aspect, various processing and analysis functions associated with avatar platform 114 can be divided between client device 106 and avatar server 116. The various features and functions of avatar platform 114 are described in greater detail infra with respect to FIGS. 2, 13 and 14.

System 100 can include one or more networks to facilitate connection/communication between the one or more sensor devices 104, intelligent fitness device 118, client device 106, and/or avatar server 114. These networks can include wired and wireless networks, including but not limited to, a personal area network (PAN), a local area network (LAN) a cellular network, or a wide area network (WAD, e.g., the Internet). For example, a sensor device 104 can communicate with client device 106 using a PAN (e.g., via short range radio communications such as Bluetooth™ near field communication (NFC), etc.). In another example, a sensor device 104 and/or client device 106 can communicate with avatar server 114 (and vice versa) using virtually any desired wired or wireless technology, including, for example, cellular, WAN, wireless fidelity (Wi-Fi), Wi-Max, WLAN, and etc. In addition, the one or more sensor devices 104, client device 106, and/or avatar server 114 can include memory that stores computer executable components and a processor that executes the computer executable components stored in the memory, examples of which can be found with reference to FIG. 20.

Client device 106 can include any suitable computing device that can facilitate generating and presenting an avatar to a user 102 that is reactive to user input including physical and physiological activity data generated or provided by the user 102. For example, client device 106 can include a desktop computer, a laptop computer, a television, an Internet enabled television, a mobile phone, a smartphone, a tablet personal computer (PC), a personal digital assistant PDA, or a wearable device. It should be appreciated that the size of client device 106 with respect to user 102 as drawn in FIG. 1 is not intended to provide a scaled relationship between one another. For instance, in an aspect, client device 106 can include a small device configured to be worn on the user's wrist, a device configured to be worn as a headband or glasses, or an 80 inch television. As used in this disclosure, the terms "content consumer" or "user" refer to a person, entity, system, or combination thereof that employs system 100 (or additional systems described in this disclosure) using a client device 118.

III—Example Avatar Guidance System

In one or more aspects, an avatar guidance system is provided that includes a reception component configured to receive physical and physiological activity information about a user during performance of a routine or program, and an analysis component configured to analyze the physical and physiological activity information based on reference physical and physiological activity metrics for the routine or the program to determine whether, how and to what degree the user deviates from requirements of the routine or the program. The system further includes a reaction component configured to determine a response for an avatar displayed to the user based on a determination regarding whether, how and to what degree the user deviates from the requirements of the routine or the program, and an avatar control component configured to initiate manifestation of the response by the avatar as displayed to the user during the performance of the routine or the program.

In another aspect, a method is disclosed that includes receiving information about a user during performance of a physical routine, wherein the physical information includes physiological information and anatomical movement information. The method further includes determining whether and how the user deviates from requirements of the physical routine based on comparison of the information to reference physical and physiological activity metrics for the physical routine, and determining a response for a performance by avatar displayed to the user based on and in response to a determination regarding whether and how the user deviates from the requirements of the physical routine, wherein the response is configured to facilitate adherence to the requirements of the physical routine. The method further includes initiating manifestation of the response, in response to the determination thereof, by the avatar as displayed to the user during the performance of the physical routine.

Still in yet another aspect, a system is provided that includes an interface component configured to generate a graphical user interface comprising an avatar configured to react to a user during performance of a physical routine by the user in response to a determination that the user deviates from a physical requirement of the routine based on analysis of physical and physiological activity data about the user generated during performance of the physical routine. The system further includes an avatar generation component configured to cause the avatar to perform a reaction that provides instruction to correct the manner in which the user deviates from the physical routine in response to reception of control commands defining the reaction, wherein the reaction comprises at least one of speech or movement; and a rendering component configured display the graphical user interface with the avatar performing the reaction.

Figure 2:
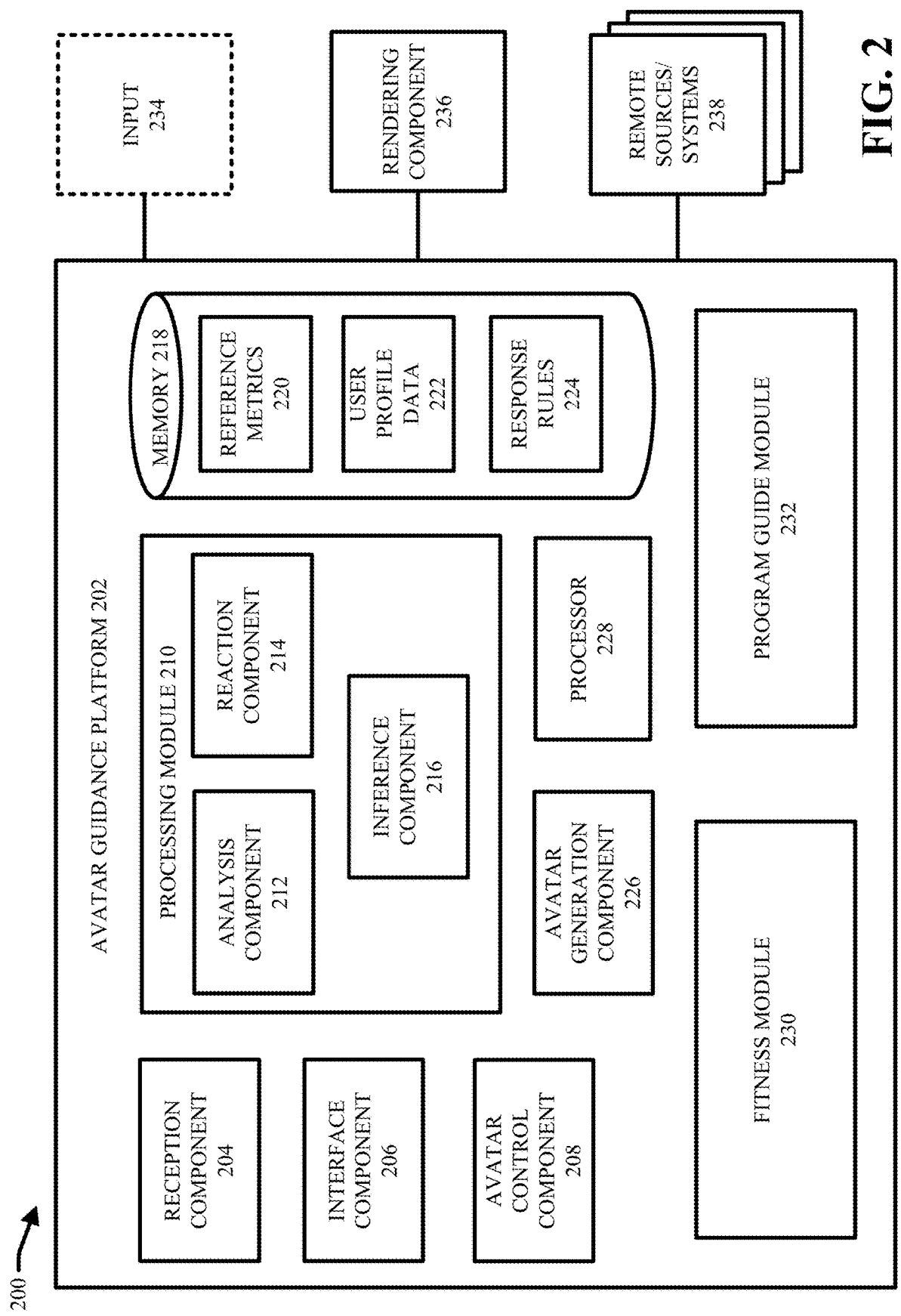
FIG. 2 provides an example avatar guidance system in accordance with various aspects and embodiments described herein.

FIG. 2 presents an example avatar guidance system 200 that facilitates guiding or assisting a user with adhering to a program, routine or activity using an avatar in accordance with various aspects and embodiments described herein. System 200 can include same or similar features and functionalities as system 100. In an aspect, system 200 employs the architecture of system 100, including one or more of the various components/devices of system 100, wherein avatar guidance platform 202 corresponds to avatar platform 114. Avatar guidance platform 202 can thus include same or similar features and functionalities as avatar platform 114. Repetitive description of like elements employed in respective embodiments of systems and interfaces described herein are omitted for sake of brevity.

Figure 20:
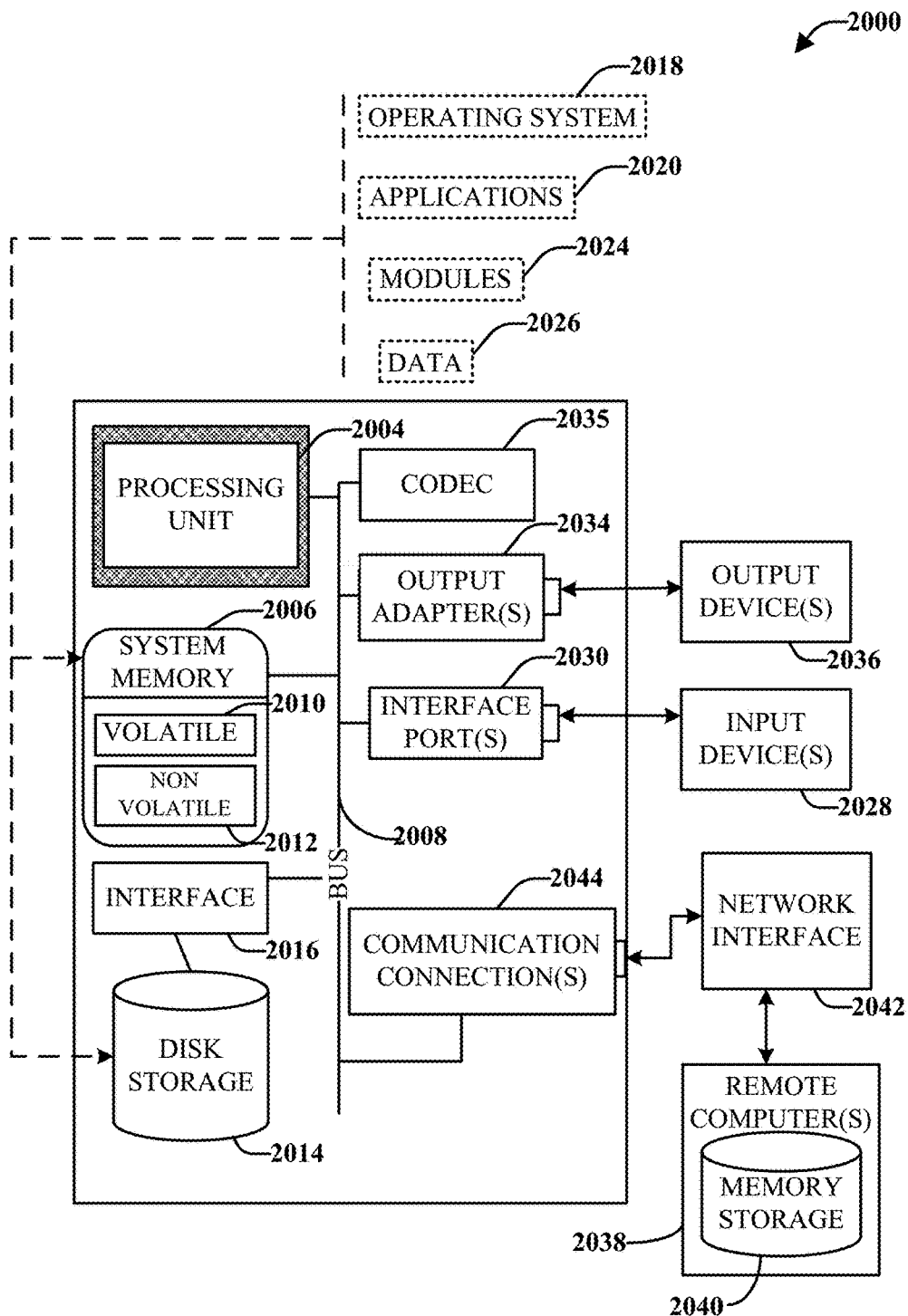
FIG. 20 is a schematic block diagram illustrating a suitable operating environment in accordance with various aspects and embodiments.

Generally, avatar guidance platform 202 can include memory 218 that stores computer executable components and processor 228 that executes the computer executable components stored in the memory, examples of which can be found with reference to FIG. 20. It is to be appreciated that although avatar guidance platform 202 is illustrated as being a standalone component, such implementation is not so limited. For example, avatar guidance platform 202 can be located at a client device (e.g., client device 106), a remote server (e.g., avatar server 116) or the cloud. In another aspect, one or more components of avatar guidance platform 202 can be located at both the client device and the remote server. Still in yet another aspect, the components of avatar guidance platform can be distributed between the client and the server.

Avatar guidance system 200 can include avatar guidance platform 202, input 234, rendering component 236 and one or more remote sources/systems 238. Avatar guidance platform 202 is configured to facilitate guiding or assisting a user in association with performing a routine, activity or program using an avatar that is responsive to various input 234 associated with performance of the program, routine or activity. The specific routine, activity or program can vary.

For example, avatar guidance system 200 can be used to facilitate guiding a user in association with performance of a specific fitness activity or routine (e.g., a single one hour workout, a yoga class, a running race, etc.). In another example, the activity could include performance of a surgical procedure, performance of a musical instrument, driving a car, or other suitable human activities requiring physical and/or mental aptitude for which guidance could be provided.

Many suitable routines, activities and programs capable of being monitored by avatar guidance platform 202 can involve those in which a physical trainer, teacher or demonstrator could potentially provide the user assistance/guidance with performing the routine or activity. For example, the routine or activity can include a physical exercise or routine where a coach or trainer may provide instruction and/or evaluation, such as performance of a physical therapy session, a planned workout, an aerobics routine, a dance routine, a yoga routine, track and field training, or a sports activity (e.g., football, baseball, soccer, basketball, tennis, golf, fencing, gymnastics, skiing, karate, horseback riding, juggling, rock climbing, diving, etc.). In another example, the routine or activity can include any activity that involves some form of physical movement that could be demonstrated and evaluated by another person, such as cooking a dish, building something, creating a piece of artwork (e.g., painting, sculpting), performing a medical operation, playing an instrument, etc.

Avatar guidance platform 202 is also configured to evaluate programs that involve user performance of various physical or physiological actions over a period of time to achieve a goal. For example, the program can include a health and/or fitness program, a dietary program, a drug rehabilitation program, a stress reduction program, or an addiction recovery program. Avatar guidance platform 202 can provide monitoring and guidance in association with adherence to the program over the course of the program while tracking the user's progress throughout the program based in part on physical, physiological, image, motion, context and user profile data. The term program is used herein to differentiate from a routine or activity with respect to the duration in that a program is generally longer in duration than a single routine or activity. The period of time can vary. For example, the period of time can include a course of a few hours, a few days, a few weeks, a few months, etc.

In an aspect, an avatar configured to guide a user through a program can function as the user's personal coach, trainer, conscience, doctor, therapist, advisor, friend, family member etc., or any other suitable persona, that can function to guide or coach the user through the program. In an aspect, this avatar can essentially know what the user is doing at all times with respect to the program (e.g., throughout the day, week, month, etc., or whenever system 200 is activated and accessible to the user).

For example, with respect to a diet/fitness program, as user physical and physiological input and/or image data is received, an avatar can respond to physical and physiological states of the user, monitor what the user eats and when, monitor how many calories the user consumes/burns, instruct the user what to eat and when, monitor when the user exercises, determine and instruct what exercises the user should perform, and assist the user with making intelligent choices in line with the diet/exercise program throughout the day. In another example, an avatar can function as a health guide for a user to facilitate improving the improving the user's overall health. For instance, the avatar can improve a user's health condition (e.g., a user suffering from an illness or ailment) by determining when the user should and shouldn't perform certain physical activities, when the user should take certain medications, when the user should eat certain foods, when the user should seek emergency health services, when the user is becoming fatigued or sick, when the user's health is improving, etc., and responding accordingly with visual and/or audible reactions. In another example, an avatar can assist a user with overcoming an addiction, such as a drug addiction or alcohol addiction, by monitoring the user's physical/physiological state throughout the day and providing the user with guidance and reactions in line with adhering to a rehab program. Still in yet another example, a user can set up a personal schedule that can involve activities the user should perform and when and avatar guidance platform 202 can monitor and facilitate adherence to the schedule.

Based on received input 234 for a user, (e.g., physiological data, motion data, image data, profile data, and/or context data) determinations and inferences can be made regarding adherence of the user to the program, routine or activity and mechanisms to facilitate adherence of the program, routine or activity. These mechanisms can be manifested by an avatar presented to the user at the time of need. For example, avatar guidance platform 202 can determine, based on received input 234 and predefined requirements/rules for a program, routine or activity, whether, how and to what degree a user is deviating from the requirements/rules of the program. In response to a determination that the user is and/or is likely to deviate from the requirements of the program, routine or activity, avatar guidance platform 202 can determine a mechanism for correcting the user's behavior and this mechanism can be communicated to the user via an avatar presented to the user. For example, when a user is becoming unproductive at his work desk and fatigued based on input indicating the user's location, the user's motion activity, the user's brain activity, the user's glucose levels, and the user's cortisol level, the avatar can notify the user and suggest that the user get up and take a walk and eat a snack.

In various implementations, the input 234 includes physical data (e.g., motion and/or image data) and physiological data (e.g., biometric/biochemical information) about the user. The physical/physiological input can be received before, during, and/or after performance of the program, routine or activity by the user. In some aspects, the input 234 is received in real-time during performance of the routine, program or activity by the user. For example, biometric/biochemical information can be received about a user in real-time during performance of a routine or activity from one or more worn or implanted biosensor devices (e.g., devices 104) or an external biometric detection device (e.g., intelligent fitness device 118). Motion data can be received about a user in real-time during performance of a routine or activity via one or more motion sensors device (e.g., devices 104) worn by the user and/or remote motion sensing devices (e.g., intelligent fitness device 118).

In addition to physical and physiological data about a user, input 234 can also include profile information for the user that defines various known characteristics of the user, including but not limited to, health information, preferences, demographics, user schedule, and historical information gathered about the user over the course of a monitored program, routine or activity. Input 234 can also include contextual information associated performance of the program, routine or activity, such as a location of the user, information about the location (e.g., a map of the location, physical structures at the location, events occurring at the location, etc.), weather information, information about other persons the user is located near and/or interacting with, and other information provided by the user during performance of the program, routine or activity (e.g., information about the user's current mood or information about what the user is currently thinking/feeling).

In various embodiments, reception component 204 is configured to receive input 234 including physical and physiological input (e.g., biometric data, biochemical data, motion data, and other physical information such as height, weight, body fat percentage, etc.) about a user automatically from various sources including but not limited to: one or more sensors attached to the user (e.g., sensors 104), an intelligent fitness device employed by the user (e.g., intelligent fitness device 118), and/or an external device employed by the user, such as a visual capture device (e.g., visual capture device 110), a sensor module (e.g., sensor module 112), or other physical data capture devices. In an aspect, raw physical and physiological data and/or image data is received by reception component as it is captured. For example, sensors (e.g., sensors 104) worn by the user can send physical and physiological activity data directed to reception component 204 in response to sensing thereby. Accordingly, physical and physiological activity data about the user can be received and processed in real-time or substantially real-time.

In addition to physical and physiological input captured by various worn, implanted and/or external devices, (e.g., devices 104 and 118), reception component 204 can receive physical and physiological information about a user from the user or another user associated with the user (e.g., the user's physical therapist, the user's dietician, the user's mom, etc.). For example, prior to beginning a particular program, routine, or activity, the user or the other user can provide avatar guidance platform 202 (e.g., via text or speech input) with profile information describing the user's health history as well as information regarding the user's height, weight, body fat index, dietary habits, medications, supplements, etc. The user can also provide other types of profile information regarding the user's preferences, the user's demographics, etc.

In some embodiments, a user's profile information can include laboratory results (e.g., provided by the user or directly from a laboratory reporting service) identifying presence and/or status of various biomarkers. For example, the laboratory results can include results from a blood test, urine test, tear fluid test, saliva text, sweat test, breath text, or other suitable biological test, performed by the user or at a medical testing laboratory. The biomarker information can include for example, biochemical information regarding at least one of: glucose level, cortisol level, blood oxygen level, blood alcohol level, inflammation, nitric oxide level, drug levels/residues present in the body, pathogens present in the body, or bacteria present in the body, folic acid, calcium, magnesium, creatine kinase, vitamin B12, vitamin D, ferritin, total cholesterol, hemoglobin, HDL, LDL, triglycerides, fatty acids, insulin, hemoglobin, hormones (e.g., thyroid hormones (thyroid-stimulating hormone (TSH), metabolic hormones, reproductive hormones, etc.), liver enzymes, electrolytes (e.g., sodium, potassium, chloride, etc.), platelets, white blood cells, red blood cells, iron, etc.

During performance of the program, routine or activity, a user can also provide avatar guidance platform 202 with feedback and/or update his or her profile information. For example, the user can regularly, (e.g., prior to beginning a workout, prior to eating, twice a day, once a day, once a week, etc.) perform biometric tests (e.g., using at home testing kits, mail in kits, home testing devices, etc.) to provide the avatar guidance platform 202 with updated profile information. The user can also update his or her profile information with respect to health history, preferences, demographics, etc.

In another aspect, reception component 204 can extract some input 234 regarding a user's physical and physiological status, demographics/preferences, and current context from one or more remote sources 238 accessible to avatar guidance platform 202 via a network (e.g., the Internet) before, during and/or after performance of a routine or program. For example, reception component 204 can access and import health information for the user from the user's health care provider or from a network based laboratory service. In another example, reception component 204 can gather a variety of information about the user's preferences, demographics, social affiliations, media preferences, etc. from various network sources the user accesses or employs (e.g., social networking sources, websites visited by the user, applications downloaded and employed by the user, articles and media accessed by the user, etc.).

In addition, reception component 204 can receive information regarding a user's location using various known location determination techniques. For example, the user can wear a locating device (e.g., a location tracking device, a global positioning system device, etc.) or a mobile client device employed by the user can include systems for determining a location of the mobile client. Location information can further be reported by these devices to reception component 204. Information regarding positions of other known persons relative to the user can be gathered in a similar manner (e.g., when such persons have authorized and enabled tracking of their location). In an aspect, reception component can receive information related to a user's location and/or environment, (e.g., physical structures, information about the physical structures, activities in the environment, weather information, etc.), from various remote sources and/systems accessible to reception component 204 (e.g., map services, new services, merchant websites, etc.).

Avatar guidance platform 202 is configured to receive and process these various inputs 234 about a user's physical/physiological state and along with various other personal and contextual information about the user to facilitate guiding and assisting the user with performance of a specific program, routine or task via manifestation of responses based on the input to the user through an avatar. In particular, the avatar is configured to function as an intelligent being that has been specifically trained to observe, analyze and respond to a user's physical and physiological data, profile information and context information in association with performance of a specific program, routine or task, based on various rule based classification schemes for the program, routine, or task, defining at least one of but not limited to: what actions or activities the user should and shouldn't perform, how the user should and shouldn't move during performance of the actions or activities, how the user's physiology should and shouldn't function during performance of the actions or activities, when the user should and shouldn't perform certain actions or activities, where the user should and shouldn't perform certain actions or activities, or how the user should and shouldn't appear. In some aspects, avatar guidance platform 202 can even monitor interaction and association of the user with other people with respect to performance of actions and activities of defined in a program, routine or task. For example, avatar guidance platform 202 can receive information indicating the user is located within X feet of an identified person and determine whether the user is authorized to interact with the identified person (e.g., at all or under the current context) based on a defined program the user is following.

Based on analysis of received input 234 with respect to a defined program, routine or task the user is performing, reactions are determined for manifestation by an avatar presented to the user. These reactions can include visual and/or audible (e.g., speech responses) responses that provide instruction, guidance, motivation, and evaluation for the user with respect to the user's performance (or non-performance) of the program, routine or task. The visual and verbal avatar reactions can embody those which a real human may perform to provide the instruction, guidance, motivation, etc. and can include but are not limited to changes in: motion or movement, speech, tone of voice, level of sound/loudness, facial expressions, body language, color, speed of movement, and range of motion.

In an aspect, the avatar is generated and presented to the user via a rendering component 236 located at a client device (e.g., client device 106). Rendering component 236 can include same or similar features and functionality as rendering component 108. Rendering component 236 can include suitable hardware (e.g., a display screen, a hologram generation device, etc.) and software (e.g., software for generating a GUI and/or software for accessing and rendering network based interface, such a browser) to accomplish generating and presenting an avatar that performs the responses determined by avatar guidance platform 202 to facilitate guiding the user with adhering to the program, routine or activity being monitored.

In various embodiments, the potential reactions for performance by an avatar in association with a specific program, routine or activity are predefined and stored in memory 218. In other aspects, reactions for performance by an avatar can be dynamically determined based on a set of response rules for the specific program, routine or activity. These response rules can account for user physical and physiological activity data as well as user profile information and user context information. Avatar guidance platform 202 can employ various machine based learning techniques to infer a suitable reaction for an avatar based on the various inputs and information accessible to avatar guidance platform 202.

Processing module 210 is configured to process various input data 234 received to facilitate guiding and assisting the user with performance of a specific program, routine or task via manifestation of responses based on the input to the user through an avatar. Based on analysis of received input 234 with respect to a defined program, routine or task the user is performing, processing module 210 determines or infers reactions for manifestation by an avatar presented to the user. In an aspect, processing module 204 process user physical and physiological information and context information as it is received and in view of user profile information to determine real-time responses to user actions (or non-actions) during a program, routine, or activity.

Processing module 210 can include analysis component 212, reaction component 214 and inference component 216. In an aspect, analysis component 212 is configured to analyze raw physical and physiological data for a user to determine or infer feature values corresponding to what the raw physical and physiological data represents. This analysis can occur in real-time or substantially real-time (e.g., as the physical and physiological activity data is generated and received, such as by client device 106 and/or avatar server 116). As described above, this raw physical and physiological data can include biometric data, biochemical data, motion or movement data, and image data.

For example, biometric data could include information corresponding to a user's heart rate, blood pressure, blood oxygen level, and temperature. In another example, biochemical information can include information regarding presence and/or concentration of various biomarkers such as but not limited to: glucose, cortisol level, blood alcohol, biochemical information regarding at least one of: glucose level, cortisol level, blood oxygen level, blood alcohol level, inflammation, nitric oxide level, drug levels/residues present in the body, pathogens present in the body, or bacteria present in the body. In another example, the biosensors can be configured to detect an array of additional biomarkers for the user, including but not limited information regarding: folic acid, calcium, magnesium, creatine kinase, vitamin B12, vitamin D, ferritin, total cholesterol, hemoglobin, HDL, LDL, triglycerides, fatty acids, insulin, hemoglobin, hormones (e.g., thyroid hormones (TSH), metabolic hormones, reproductive hormones, etc.), liver enzymes, electrolytes (e.g., sodium, potassium, chloride, etc.), platelets, white blood cells, red blood cells, iron, etc.

In an aspect, received biometric data is received in a processed form to indicate the feature value it represents (e.g., heart rate, blood pressure, blood oxygen level, temperature, glucose level, cortisol level, blood alcohol level, etc.). For example, analysis component can receive processed data identifying a user's blood oxygen level based on received results from a pulse oximeter. In some aspects however, analysis component 212 can interpret raw signals from various sensors to determine feature values for the biometric data.

In various embodiments, analysis component 212 is configured to determine or infer one or more characteristics of a physiological state or condition of a user based on received biochemical information about a biochemical state of the user, including information identifying a presence or a status of one or more biomarkers. For example, based on detected presence of a particular biomarker, analysis component 212 can determine a known medical condition or disease exhibited by the user. In another example, analysis component 212 can determine whether and to what degree levels of the respective biomarkers are abnormal (e.g., with respect to predefined values or ranges for normal vs. abnormal levels). Analysis component 212 can further determine or infer known conditions or diseases of the body that are attributed to the abnormal levels of the respective biomarkers.

In another embodiment, based on the information identifying the presence and/or status/level of various biomarkers, analysis component 212 can determine one or more characteristics associated with a state of a human body system of the user, such as whether the body system is in a healthy state or an unhealthy state (and varying degrees between severely unhealthy or extremely healthy) and why, whether the system is functioning properly or improperly and why, whether the system is functioning at a desired performance level (e.g., in association with a particular physical activity), etc. These human body systems include at least one of: the integumentary system, the skeletal system, the nervous system, the cardiovascular system, the endocrine system, the muscular system, the lymphatic system, the respiratory system, the urinary system, the excretory system, the reproductive system, the digestive system, and the immune system.

For example, the cardiovascular system includes the heart and blood vessels, and is responsible for transporting oxygen, nutrients, hormones, and waste products throughout the body. A healthy cardiovascular system ensures a good balance of nutrients and optimal brain and body function. In an aspect, analysis component 212 can determine levels of respective biomarkers related to a user's lipid panel (e.g., HDL, LDL, triglycerides, non-HDL cholesterol, etc.). Analysis component 212 can further determine whether the levels are within an acceptable range and/or whether the levels are indicative of a particular disease of physiological condition.

Analysis component 212 can also determine a general health status of the user's cardiovascular system based on the user's lipid panel. For example, analysis component 212 can determine a degree of risk the user has for cardiovascular disease based on detected levels of HDL, LDL, triglycerides, non-HDL cholesterol, etc. Higher levels of LDL cholesterol can result in increased amounts of plaque in the blood vessels, which can obstruct blood and oxygen flow to vital organs. By reducing those deeper LDL numbers, one can reduce the risk of a heart attack and stroke. Similarly, by increasing ones HDL, one can reduce the risk of developing cardiovascular disease. Analysis component 212 can also determine the status of a user's heart health based on levels of fatty acid biomarkers (e.g., omega-3 fatty acids and omega-6 fatty acids).

In another example, based on biomarker levels for C-reactive protein (hs-CRP), Lipoprotein-associated phospholipase (Lp-PLA2), homocysteine, and fibrinogep, analysis component 212 can determine a degree of inflammation experienced by a user. Inflammation is a natural reaction to stress or injury. In addition to facilitating injury recovery/prevention in the short term, by regularly monitoring a degree of inflammation experienced by a user, one can regulate development of chronic diseases such as cardiovascular disease, cancer, diabetes, dementia, and osteoporosis.

Analysis component 212 can further determine characteristics about a user's metabolic health/state based on various known biomarkers. Metabolic monitoring is the periodic recording of metabolic markers that give information on specific metabolic pathways. Diabetes mellitus, obesity and intense physical activity are a few examples where close metabolic monitoring is necessary and beneficial. Metabolism is the body's way of chemically processing sugar and fat for use throughout the body as energy. An optimal metabolism supports healthy weight control and energy levels, while a dysfunctional metabolism can lead to undesired fluctuations in weight and fatigue or hyperactivity.

In an aspect, analysis component 212 can also determine characteristics about a user's metabolic health (e.g., how well the user's body is metabolizing the user's diet, whether a user's metabolism is functioning at an optimal state or a dysfunctional state and varying degrees there between, etc.) based on levels of biomarkers including but not limited to: insulin, hemoglobin, glucose, lactate and triglycerides. For example, biomarkers identifying high levels of blood sugar (e.g., glucose) can serve as an indicator of cardiovascular disease, kidney disease, susceptibility to blindness and ulcers. Insulin, a hormone created in the pancreas, helps the body use or store blood glucose from food. High levels of insulin and blood sugar can indicate type-2 diabetes. Optimal levels of triglycerides play a role in providing energy and ensuring healthy metabolism.

Analysis component 212 can further determine characteristics about a user's metabolism based on levels of thyroid biomarkers. The thyroid gland is the body's regulator of metabolism. An underactive thyroid, or hypothyroid, can result in low energy, weight gain, and cold intolerance, while an overactive thyroid, or hyperthyroid, can cause hyperactivity, undesired weight loss, and heat intolerance. In an aspect, analysis component 212 can to determine the degree of over-activity or under-activity of a user's thyroid based on biomarkers including but not limited to: thyroid-stimulating hormone (TSH), free T3, T-update, T4, thyroid peroxidase, thyroxine, free thyroxine, reverse and T3. In another example, based on metabolic hormone biomarkers, including cortisol, insulin, insulin-like growth hormone, analysis component 212 can determine whether and to what degree a user's metabolic hormones are imbalanced. The manner in which a user's hormones are balanced influences the way the user metabolizes, fat, sugar, and protein to produce and store energy and build tissues such as fat or muscle.

In an exemplary embodiment, based on detection of various metabolic biomarker levels, analysis component 212 can determine a level of exhaustion experienced by a user (e.g., throughout the day, prior to exercise, during exercise, after exercise, etc.). Exhaustion, also known as fatigue, is the inability of muscle to continue an ongoing physical activity. Exhaustion has been linked to several metabolic pathways and therefore a close examination of the metabolic processes involved in physical activity could facilitate a more accurate prediction of exhaustion. Depletion of fuel stored in the muscle (i.e., creatine and glycogen, that are readily accessible as an energy source), as well as accumulation of metabolic byproducts (e.g., chloride and potassium ions and lactic acid) are considered the causes of exhaustion. Therefore, analysis component 212 can determine a user's level of exhaustion based on biomarkers including creatine, glycogen, chloride, potassium, and lactic acid. Analysis component 212, can further determine a level of user exhaustion and/or likelihood of exhaustion based on periodic changes in a user's glucose and lactate levels. Glucose is the primary energy source of muscle cells, and lactate is the main by-product of anaerobic metabolism during intense activity.

In another aspect, analysis component 212 can determine whether a user's reproductive hormones are present at proper levels, including but not limited to: estradiol, progesterone, follicle-stimulating hormone, luteinizing hormone, free testosterone, testosterone, DHEA-S and SHBG. These reproductive hormones are produced by a complex interaction of the brain, adrenal glands, and reproductive organs. In some aspects, analysis component 212 can determine the effects different levels of these hormone have on a user's overall growth and muscle gain, metabolism, mood, libido, and reproductive health.

Analysis component 212 can also analyze liver enzyme biomarkers including but not limited to: alanine aminotransferase (ALT), alkaline phosphatase (ALP), aspartate transaminase (AST/SGOT), bilirubin, albumin, and globulin to determine whether and to what degree a user's liver is functioning in a proper and healthy state. For example, a marked elevation in liver enzymes can signify liver dysfunction. Liver enzyme levels provide an indication of liver inflammation, most commonly from medications, infections, or excess body fat. The liver's main function is to filter blood coming through the digestive tract. The liver is also responsible for detoxifying chemicals, metabolizing drugs, producing proteins, and more. Liver dysfunction can have a negative impact on your immune system and energy levels and can lead to liver disease and cancer.

Analysis component 212 can also determine characteristics of a user's kidney functioning based on various kidney related biomarkers including creatinine serum, eGFR, blood urea nitrogen (BUN), and albumin. Proper kidney function reflects how well the kidneys are filtering blood. Abnormal kidney function can result in the accumulation of waste products in the body which can cause fatigue, headaches, nausea, and more.

Analysis component 212 can further analyze levels of biomarkers including sodium, potassium, chloride, carbon dioxide and calcium to determine a state of a user's electrolytes. For example, analysis component 212 can determine whether a user's electrolytes are balanced or imbalanced and to what degree of imbalance. An electrolyte imbalance can lead to an imbalance in the body's acid-base status, hydration, or conduction of charges across cells, all of which are essential, especially with increased activity. In another example, analysis component 212 can determine a level of a user's electrolytes and whether the level is considered low/high (e.g., relative to an optimal level).

In addition, analysis component 212 can determine characteristics of a user's bone health (e.g., whether they are healthy/unhealthy, diseased, inflamed, etc.,) based on biochemical information regarding levels of vitamin D (and its precursors), calcium and alkaline phosphate (ALP). Bone biomarkers are indicators of how well bone tissue is being removed and replaced, aka "bone remodeling." When bones remodel excessively or become inflamed, there may be large elevations in ALP. Significantly abnormal marker levels suggest possible bone disorders.

Analysis component 212 can also determine characteristics of a user's blood health based on levels of a user's platelets, white blood cells, red blood cells, and iron. Blood consists of two main components: the cellular components (red blood cells, white blood cells, and the cell fragments known as platelets); and the liquid component, called plasma. Together, these two parts of the blood are responsible for many functions, including oxygen transport, temperature regulation, blood clotting, and immune defense. Platelets help form blood clots at the site of an injured blood vessel. By knowing a user's platelet count as well as how large the platelets are, analysis component 212 can determine whether a user has any bleeding or clotting problems. White blood cells are responsible for protecting the body from disease and foreign materials. A low white blood cell count provides an indication of a user's ability to fight disease, while an overproduction of white blood cells could indicate the presence of diseases like leukemia. Red blood cells are the most numerous cell types in the blood and have one main role: to carry oxygen to tissues in the body and transport carbon dioxide back to the lungs to be exhaled. A low red blood cell count can indicate that a user is anemic. In association with analyzing a user's blood health, analysis component 212 can determine a user's iron levels. Iron is an essential mineral needed to form hemoglobin, the main protein found in red blood cells. Iron deficiency can lead to anemia, while excess iron can be toxic to the liver or other organs.

In some implementations, analysis component 212 can determine levels of a user's vitamins and minerals to determine whether a user has a vitamin and/or mineral deficiency. For example, analysis component 212 can identify a user's folate levels, vitamin D (and its precursors) levels, vitamin B12 levels, RBC folate, RBC magnesium, and calcium. Vitamins are organic substances required for normal health and function. For example, vitamin B12 is essential for cellular development, including the development of red and white blood cells. Deficiency in B12 can indicate and lead to anemia and immune dysfunction. Minerals are inorganic substances needed for many of the body's processes such as cellular development, carrying oxygen to tissues, and bone growth. Mineral deficiencies result in weak bones, organ malfunction, and poor cellular development, which can cause conditions such as anemia.

Analysis component 212 can also determine a user's antioxidant levels (e.g., levels of beta-carotene, lutein, lycopene, selenium, vitamin A, vitamin C, vitamin E, etc.). Antioxidants are substances the body uses to defend against a whole range of health worries. By preventing the emergence of free radicals, antioxidants keep people feeling and looking more youthful. Antioxidants also help to protect against diseases and the detrimental aging effects of smoking, alcohol, dietary choices, sleep deprivation, and the ravages of stress.

In addition to characteristics about a user's physiological state, analysis component 212 can analyze raw motion data to determine a type of movement performed (e.g., walking, squatting, jumping, etc.) by the user and various characteristics of the movement, (e.g., range of motion, balance, weight/pressure, and even specific two or three dimensional coordinate positions of respective parts of the user's body as they move as a function of time). For example, based on the motion data for the user as a whole and/or individual body parts of the user (e.g., corresponding to velocity, direction, orientation, position or pressure, etc.), analysis component 212 can determine a movement a user is performing including the precise position of the user's body parts with respect to one another and the ground or an apparatus over a period of time. In another example, analysis component 212 can determine feature values based on image data corresponding to the user's appearance, including two and three dimensional measurements of the user's body and individual parts (e.g., while moving over time or at a still position), color data, characteristics of facial expressions, etc.

In addition to processing of received physical/physiological data (e.g., biometric/biochemical data and motion data), analysis component 212 can further determine a user's current context at a time during receipt (or non-receipt) of the physical and physiological data. For example, based on received context information, analysis component 212 can determine a location of the user at respective times throughout the day (e.g., using an internal clock). Analysis component 212 can further determine information about the location by parsing various remote sources/systems 238 that provide information related to the location and/or the current time. For example, analysis component 212 can extract a map of the location, determine what physical structures are at the location (e.g., houses, places of business, landmarks, etc.), information about the physical structures (e.g., hours of operation), events occurring at the location (e.g., traffic, sports match, etc.), current and prospected weather conditions of the location, etc. Other context data that can be provided to analysis component 212 and/or determined by analysis component 212 can include but is not limited to: information regarding other persons the user is located near and/or interacting with, what mood the user is in, or what the user is currently thinking/feeling. The various features that make up a user's context are referred to herein as context parameters.

Accordingly, analysis component 212 can essentially determine at any point in real-time at which input 234 is received, feature values corresponding to at least one of: a physiological state of the user, a biochemical state of the user, a movement of the user or characteristic of the movement, an appearance of the user, and a context of the user. Therefore, analysis component 212 can determine or infer what actions or activities the user is performing, how the is moving during performance of the actions or activities, how the user's physiology is functioning during performance of the actions or activities, when the user is performing the actions or activities, where the user is performing the actions or activities, how the user appears when performing the actions or activities, who is near the user during performance of the actions or activities, and what the user is thinking or feeling (e.g. based on information provided by the user and/or various inferences based on the other information and determinations) during performance of the actions or activities.

In various embodiments, after analysis component 212 has determined feature values and/or context parameters based on received physical and physiological activity data and/or context data, respectively, analysis component 212 then analyzes and/or evaluates a user's performance of the routine, activity or program. In an aspect, in order to evaluate the user's performance of the routine/activity/program, analysis component 212 evaluates whether, how and to what degree the user is deviating and/or is likely to deviate from the routine/activity/program, based on these feature values and/or context parameters and known/predefined requirements physical/physiological and/or context metrics for a program, routine or activity being monitored. As discussed above, the specific program, routine or activity that avatar guidance platform 202 is monitoring can vary.

In one embodiment, avatar guidance platform 202 can be used to assist a user in association with performance of a physical fitness routine or activity. According to this embodiment, avatar guidance platform 202 can receive physical and physiological activity data for a user during performance of the fitness routine/activity and compare this physical and physiological data to reference physical and physiological metrics for the health/fitness routine to determine whether the user's physical and physiological performance deviates from the reference physical and physiological metrics. For example, in response to a determination that the user is moving too fast or too slow, has a heart rate to high or too low, is incorrectly or correctly performing a fitness movement, etc., avatar guidance platform 202 can determine a response to manifest via an avatar to respond to the deviation or non-deviation. For example, avatar guidance platform 202 can determine an appropriate verbal command or remark for the avatar to speak (e.g., "your heart rate is too low, lets speed it up") and/or a physical appearance/motion for the avatar to effectuate (e.g., the avatar can demonstrate the correct motion, the avatar can express an emotion of gratitude via a facial expressions and body movements, etc.). Avatar guidance platform 202 can then cause an avatar generated and presented to the user via a GUI (or as a hologram) to carry out the response (e.g., speak the command, perform the motion and appearance change, etc.).

In an aspect, the program, routine, or activity that is monitored by avatar guidance platform 202 is selected by the user (or another entity) from a list of predefined programs, routines, or activities that avatar guidance platform 202 is configured to monitor. In another aspect, avatar guidance platform 202 can allow the user or another entity to design a custom program, routine or activity for the user. In an aspect, custom programs, routines or activities can be saved and made available to other users of avatar guidance platform 202 for selection and performance.

For example, a user can select a specific activity or program (e.g., a fitness routine, a sports activity, a diet program, a stress reduction program, etc.) to be monitored by avatar guidance platform 202 or another user can elect the activity or program for the user (e.g., the user's real life supervisor, doctor, coach etc.). For instance, the user can select a yoga routine, a golf lesson, a diet program, or a stress management program to follow and have monitored by avatar guidance platform 202. In another example, a user or supervisor of the user can create a custom program for a user that defines a schedule the user should adhere to, what actions the user should and shouldn't do and when/where, what physiological and/or biochemical status the user should have and when, etc. In another aspect, a user can employ avatar guidance platform 202 to monitor several different programs, routines or activities for the user concurrently. For example, the user can employ the avatar guidance system 200 to set up a personal training avatar to monitor an exercise and fitness program for the user as well as a personal assistant avatar configured to monitor the user's adherence to a personal weekly schedule designed by the user.

In an aspect, based on known/predefined requirements for a program, routine or activity being monitored, analysis component 212 can determine or infer whether, how and to what degree the user is deviating from the program, routine or activity. For example, based on a user's physical and physiological feature values and/or context parameters and known requirements for these values/parameters for the particular program, routine or activity, analysis component 212 can determine or infer information including but not limited to, whether, how and to what degree: the user's physical actions or activities deviate from the action/activity requirements of the program, routine or activity; the user's movements deviate from the program; the user's physiological state (e.g., based on biometric/biochemical information) deviates from the physiological state requirements of the program, routine or activity; and the user's appearance deviates from the appearance requirements of the program, routine, or activity.

In another aspect, based on known requirements for a program, routine or activity (and user profile information), analysis component 212 can determine or infer whether, how and to what degree a user is likely to deviate from the requirements of a monitored program, routine or activity in the foreseeable future. For example, analysis component 212 can determine or infer when one or more physical and physiological activity feature values and/or context parameters are near or approaching (e.g., within a threshold degree of deviation) a limit value for the physical and physiological activity feature values and context metrics required by the program, routine, or activity (e.g., when your blood pressure is close to exceeding the limit, when your location is near a forbidden location and you are moving in the direction to the forbidden location, etc.).

In an aspect, known requirements for a specific program, routine, or activity can include predetermined reference metrics for the specific program, routine or activity defining values or value ranges for what the user's physical/physiological input feature values and/or context parameters should be. For example, each specific routine, program or activity monitored by avatar guidance platform can be associated with a set of predefined reference metrics identifying physical and physiological feature values that are to be exhibited by the user during performance of the routine, program or activity in association with specific time points, events, or circumstances defined for the routine, program or activity. In an aspect, these reference metrics 220 are stored in memory 218. These reference metrics can be applied to various algorithms and classification schemes that relate the reference metrics to determined feature values and/or context parameters with respect adherence to of the user to a specific program, routine, or activity. Accordingly, analysis of physical and physiological feature values and/or context parameters with respect to reference metrics can involve various ruled based classification schemes wherein the feature values are analyzed based in part on the reference metrics for the program, routine or activity to determine whether the user's physical and physiological feature values and/or context parameters indicate the user is deviating from and/or likely to deviate from, the program, routine, or activity, how the user is deviating and/or is likely to deviate, and or to what degree the user is deviating and/or likely to deviate, (wherein likely can be measured in terms of probability).

In an aspect, evaluation of adherence to a specific program, routine or task includes a simple comparison of physical and physiological activity feature values and/or context parameters to known reference metrics for the specific program, routine or activity. In another aspect, the set of predefined reference metrics for a program, routine, or activity can include model/reference value ranges for the physical and physiological activity feature values and/or the context parameters. According to this, aspect, adherence and/or non-adherence to an aspect of a program, routine or activity can be based on deviation outside of a threshold range. A set of reference metrics for a program, routine, or activity can also include model/reference values or model/reference value ranges for different combinations of physical and physiological activity feature values and/or context parameters.

For example, based on a comparison of a physical and physiological feature values or set of physical and physiological feature values to a reference physical and physiological feature value or set of reference physical and physiological feature values, analysis component 212 can determine, whether the user's blood pressure is too high or too low, whether the user's inflammation level is acceptable, whether the user's cardiovascular system is functioning at a desired level of performance, whether a user is becoming fatigued, or whether a user is exhibiting a desired level of physical exertion. In an another example, based on such a comparison, analysis component 212 can determine, whether the user's stress levels are appropriate, whether the user's blood sugar is high or low, whether the user has consumed enough calories, whether the user has burned enough calories, or whether the user lost the desired amount of weight or inches of her waist, etc. Still in yet another example, in association with performance of a fitness routine and received biochemical information for the user regarding a user's current electrolyte levels (e.g., sodium, potassium, chloride, carbon dioxide in blood, and calcium), analysis component 212 can determine whether the user's biochemical state indicates an imbalance in body acid-base, hydration, or conduction of charges across cells (i.e., all of which are essential, especially with increased activity).

In another example, in association with performance of a physical fitness routine and reference metrics that define what the user's body movement and position should correspond to over the course of the fitness routine, analysis component 212 can determine when the user's body position and movement deviates from the requirements of the fitness routine, whether the user's body position is correct, or whether the user's performing an exercise correctly with the proper intensity and form. In another example related to analysis of physical and physiological activity feature values, based on comparison of biometric data for a user indicating a user's heart rate is 180 beats per minute (bpm) to reference metric data that defines the target heart rate for the exercise to be 150 bpm, analysis at step 210 can output a determination that the user's heart rate is too high, specifically 30 bmp too high. In yet another example, based on comparison of motion data indicating a user's motion pattern corresponds to X when is should correspond to Y, analysis at step 210 can output a determination that the user's motion is incorrect and even more specifically how the motion is incorrect (e.g., the user's legs should be bent another 10°).

In addition to physical and physiological activity feature based reference metrics, programs, routines and be associated with context reference parameters that define requirements such as location, time of day, environmental characteristics, user mood, and other people within proximity to or interacting with the user. For example, a particular monitored activity or program, such as program designed to restrict an adolescent's social behavior (e.g., by the adolescent's parents), can be associated with various predetermined metrics and rule based classification schemes regarding what the adolescent should be doing, when the adolescent should be doing it, where the adolescent should be located, and/or who the adolescent should or shouldn't be with. Accordingly, received contextual information regarding where a user is located and when, combined with external accessible information about the user's environment (e.g., physical structures, events, etc.) and received physical and physiological activity data for the user (e.g., movement patterns, the user's stress levels, the user's activity levels, user fatigue levels), can facilitate determining or inferring adherence to the activity or program.

For example, based on a user's location and time of day determinations can be made regarding the physical environment of the user, such as the terrain, what places of business are around, and what events are occurring at the location, (e.g., a football game). Depending on the user activity or program being monitored, this information can facilitate determinations regarding adherence to the activity or program. For example, an alcohol addiction recover program can include context metrics that define triggering locations for the user at specific, such as areas within X meters from a bar between the hours of 5 pm and 7 pm. According to this example, analysis component can determine or infer that the user is deviating from the program or is likely (e.g., has a determined probability of deviated over a threshold probability) when headed into an area with a bar a at happy hour time. In another example, with respect to a stress reduction program, reference metrics can define what the user's heart rate, cortisol level, glucose levels, prescription drug levels (e.g., when the user is directed to take a particular drug according to the program), activity levels and sleep patterns should correspond to throughout the day, when at various locations, when interacting with certain people, and/or with respect to certain activities, (e.g., working, driving, operating a certain machine, reading a book, going for a walk, etc.).

It should be appreciated that the above example comparison based evaluations of physical, physiological, and/or context parameters to reference metrics are merely exemplary. In particular, a variety of more complex rule based classification schemes can be defined that relate a plurality of concurrently received or applicable physical and physiological activity feature values and/or context parameters to one another and their respective reference values for the particular activity or program to determine whether, how, and to what degree, a user is deviating from a program, routine or activity.

In addition to comparison of determined physical and physiological activity feature values and/or context parameters to the reference metrics for the program, routine or activity, analysis component 212 can employ user profile data 222 to personalize evaluation of the user's performance and adherence to the program, routine or activity. As a result, the various aspects and applications of avatar guidance platform 202 can be highly personalized.

For example, in one an aspect, the set of predefined reference metrics for a specific program, routine, or activity can generically suited for a model user. In another aspect, the reference metrics can be provided or adapted by the user performing the activity or program or a supervisor of the user (e.g., an entity or person who instructed the user to perform the activity or program using the subject avatar response system 114, such as the user's coach, health advisor, rehab program administrator, mother, etc.). Still in yet another aspect, analysis component 212 can adjust or calibrate evaluation (e.g., using rule based classification schemes and other intrinsic calculations) of physical and physiological activity feature values and/or context parameters using respective reference metrics for the program, routine or activity, based on user profile data.

User profile information can include but is not limited to, health information, user preferences, user demographics, user schedule and historical information about the user's behavior in association with performance of various activities and programs monitored by the avatar response system 114. Health information can include any information related to the user's health and physical state, including known physical metrics for the user (e.g., height, weight, body fat, etc.), physical conditions or ailments of the user, physical capabilities of the user, and any medications taken by the user. As noted above, in some embodiments, user profile information can also include biochemical information about a user determined from various biological tests (e.g., blood test, urine test, saliva test, etc.). In other aspects, biochemical information can be received for a user during performance of a monitored routine or program.

User preference information can vary depending on the application of the avatar guidance platform 202 for the user. Some examples of user preference information can include features and aspects of a fitness, health or other type of an activity or program that the user prefers/likes and/or does not prefer (e.g., foods the users likes/dislikes, dietary restrictions, places the user likes to go/not go, exercises the user likes/dislikes to perform, when the user liked to perform or not perform various activities, etc.). In another example, preference information can relate to what types of character traits that the user desires in an avatar designed to respond to, coach or instruct the user. Still in yet another example, user preference information can include information defining goals of the user (e.g., fitness goals, weight loss/weight gain goals, what the user desires to look like, milestones in a recovery program, and targets for performance of various other activities).

User demographic information can define various demographic features of the user, including but not limited to: gender, age, nationality, language, education level, or profession. User schedule information can provide information regarding what the user should and shouldn't be doing and when based on the user's work, extracurricular activities and personal relationships and responsibilities. For example, user schedule information can be provided to determine when a user should be at work and where, what meetings the user has, when the user has set up events or social activities, when the user has vacations scheduled, doctors appointment scheduled, physical therapy or fitness session scheduled, etc. In an aspect, user schedule information can be extracted from a personal calendar of the user (e.g., from an application employed by the user on the user's client device 106 and/or at remote source/system 238).

Profile information can be received from various sources. In an aspect profile information can be provided by the user in association with registration with avatar response system 114, provided by another entity or source (e.g., medical professional, coach, fitness trainer, therapist, rehab program director), automatically imported by the avatar response system from various external sources (e.g., heath records, the user's calendar, social networking profiles, etc.), and/or automatically inferred or determined by the avatar response system.

In an aspect, analysis component 212 can employ user profile information to facilitate determining or inferring a probability at which a user is likely to deviate from a monitored program, routine or activity within the near future (e.g., within the next 10 seconds, within the next minute, within the next 10 minutes, within the next 30 minutes, within the next hour, etc.) based on physical and physiological activity features values and/or context metrics received/determined for the user. For example, analysis component 212 can analyze user patterns with respect to past deviations for program requirements similar to a current program requirement to determine the probability that the user will deviate from the current program requirement when physical and physiological activity feature values and/or context parameters for the user are x, y, and z, (where x, y and z correspond to variable values). In another example, analysis component 212 can analyze user preferences (e.g., what the user prefers to eat/drink, where the user prefers to go, what the user prefers to do, who the user prefers to associated with, etc.), to determine or infer how a degree of likelihood that the user will deviate from requirements of a monitored program given known information for the user's physical state (e.g., appearance, physiology), the user's body movement/position, and the user's context.

Reaction component 214 is configured to determine or infer a reaction (or non-reaction) for manifestation by an avatar presented to the user based on a determination by analysis component 212 identifying whether, how and to what degree a user is violating or is likely to violate a monitored program, routine or activity. In particular, a reaction component 214 can determine an action for performance by the user based on an identified deviation or likely deviation from a program/routine/activity requirement that will or is likely to correct/avoid the deviation. In some embodiments, reaction component 214 can further determine the action based in part on biochemical information received for a user prior and/or during performance of the routine/activity/program (e.g., information regarding a physiological state or condition of a user based on detection of the one or more biomarkers discussed herein), profile information for the user, and/or received contextual information. Reaction component 214 can further determine, based on the action, a reaction for manifestation by an avatar presented to the user that guides or motivates the user to perform the action.

The reaction is designed to keep the user's physical/physiological performance and behavior in line with the requirements or goals of a monitored program, routine or activity. For example, when a user deviation is determined, reaction component 214 can determine a reaction for manifestation via an avatar that will instruct the user how to correct the deviation and/or encourage the user to correct the deviation or improve upon the deviation (e.g., where the deviation reflects positive behavior). In another example, when analysis component 212 determines that a user is complying with a program, routine, or activity, reaction component 214 can determine a reaction for manifestation via an avatar that provides praise to the user. In another example, when analysis component 212 determines that a user is likely to deviate from a program, routine or activity, reactions component 214 can determine a reaction for manifestation by an avatar that is designed to deter or prevent the user from deviating from the program, routine or activity.

In an aspect, a reaction determined by reaction component 214 for manifestation by an avatar can involve visual or spoken instruction by the avatar providing a mechanism to correct a deviation to a program, routine, or activity, an action taken by the avatar to deter or prevent the user from deviating from the program, etc., a tactic to motivate the user to adhere to the program, etc., a tactic to praise the user for adhering to the program, etc., or a tactic to criticize the user for not adhering to the program, etc. These reactions can involve visual and verbal actions which a real human may perform and can include but are not limited to changes in: motion or movement, speech, tone of voice, level of sound/loudness, facial expressions, body language, color, speed of movement, and range of motion. For example, the avatar can speak to the user and demonstrate body movement and facial expressions that a real human would in order to convey a reaction. In another aspect, an avatar reaction can include sending an electronic message (e.g., email, text message, etc.), or initiating a phone call to another entity via the client device (e.g., client device 106) employed to render the avatar.

For example, based on a determination by analysis component 212 that a user's heart rate is too high while performing a fitness routine, reaction component 214 can determine that the user should slow his or her heart rate down by decreasing the pace. Reaction component can further determine a response for manifestation by the avatar that directs the user to slow down. For example, the determined reaction to be manifested by the avatar can include a verbal spoken command to "slow down the pace" as well as a physical demonstration by the avatar of the exercise at the correct pace.

In another example, based on a determination by analysis component 212 that a user's physiological state indicates the user is experiencing high amounts of inflammation and an imbalance of electrolytes, reaction component 214 can determine a response for manifestation by an avatar that guides or motivates the user to perform an action to correct or improve the user's physiological state. For instance, the action (as determined by analysis component 212) can include an action that is known or determined to improve the user's physiological state, such as but not limited to: performing a particular physical exercise, performing a particular, stretch, eating a particular food or beverage, ingesting a particular drug or dietary supplement, performing a therapeutic treatment (e.g., massage, icing, or heat treatment), resting, or seeking emergency medical treatment. In an aspect, the reaction by the avatar can include a verbal command to perform the action spoken with a specific tone or with a specific facial expression, determined based on the action. In another aspect, the reaction by the avatar can include a behavior to be performed by the avatar with a specific facial expression determined based on the action.

In another example, in response to a determination by analysis component 212 that a user participating in an alcohol addiction recovery program has a blood alcohol level of X and/or is located at or near a bar, a response can be determined by reaction component 214 for manifestation by an avatar that includes verbal instruction criticizing the user for the bad behavior with corresponding facial expression and body language that showing an expression of disappointment. In addition, reaction component 212 can initiate calling of the user's alcohol anonymous (AA) sponsor and the avatar presented to the user can inform the user that a phone call is being initiated. In another example, in response to a determination that a user is likely to deviate from a diet program based on information indicating the user is stressed, the user is hungry, and the user is near another person that the user usually makes deviating food choices with on Monday afternoons (when the time is Monday 3 pm), reaction component 214 can determine a reaction for manifestation by an avatar that calls the user's attention to the scenario, and provides the user with breathing exercises to perform with the avatar as a guide to reduce the user's stress before the user's makes any poor decisions.

In another aspect, an avatar reaction can include provision of external data to the user at the client device (e.g., client device 106) employed to render the avatar. The external data can include but is not limited to: documents, articles, media, multimedia (e.g., video, animations, sounds, music, etc.), or hyperlinks to these data objects, that are accessible to avatar guidance platform (e.g., in memory 212, or at a remote source/system 238). For example, in association with an avatar reaction to facilitate encouraging a user to stick to an anti-smoking program, the avatar can provide the user with an article about the effects of smoking. In another example, to encourage a user to adhere to a fitness program, the avatar can provide a user with an image of herself when she used to weight 25$lbs$ more and an image of what she will look like at her goal weight.

In another example, in response to a determination by analysis component 212 that a user on a diet program is becoming stressed (e.g., based on cortisol levels) and has taken a walk to the vending machine (e.g., based on location and movement data), reaction component 214 can determine or infer a reaction for manifestation by an avatar that deters the user from making bad food choices. For example, reaction component 214 can determine a response that includes providing the user with motivation to stick to the diet program by playing a video of the user's past fitness dedication. The avatar can further speak to the user to encourage the user not to select the candy bar from the vending machine and rather go to the cafeteria to get a banana (e.g., a preferred snack option determined based on the user's food preferences and dietary restrictions).

In an aspect, reaction component 214 can determine or infer what action or inaction the user should do to correct an identified deviation and then determine or infer a proper reaction for manifestation by the avatar to direct the user to perform the action. For example, in response to a determination by analysis component 212 that a user has not mastered a particular golf swing (e.g., based on a determination that the user's physical motion indicates improper performance of the golf swing), reaction component 214 can determine that the user should switch to practicing a different swing and associated club. Thus reaction component 214 can determine a response for manifestation by an avatar that includes verbal instruction telling the user to switch to the other club along with physical simulation of the new golf swing with the new club.

The particular response determined by reaction component 214 for manifestation by an avatar can be based on a plurality of factors and information. In an aspect, known deviations, deviation types and degrees of the deviations for a specific program, routine or activity can be defined and correlated to fixed avatar reactions. For example, for a fitness routine, if blood pressure is too high, the associated avatar response can include a slowing down movement. In addition, reaction component 214 analyzes user profile information to tailor response to the particular user, (e.g., based on user preferences, user demographics, user health information, user behavioral history, etc.). Further, reaction component 214 can consider context information when determining a reaction for manifestation via an avatar to counterbalance a deviation (or adherence) to a program, routine or activity. For example, when reaction component 214 determines that a user should perform an action to reduce stress (e.g., based on a determination that the user's stress level is too high in association with a stress reduction program), reaction component 214 can determine the action based on the user's location, weather conditions, time of day, etc. For instance when it is raining, the action can include performing yoga indoors, yet when it is not raining, the action can include taking a walk outside.

In an aspect, reaction component 214 can employ various defined response rules 224 that relate known deviations and degrees of the deviations for a specific program, routine or activity, with user profile information and context information to a plurality of possible pre-defined avatar reactions. For example, the response rules 224 can include a set of prefixed avatar responses that are mapped to potential determinations of deterrence and/or adherence to a particular activity or program. These prefixed responses are specific to the program, routine, or activity being monitored. In an aspect, prefixed responses are defined by an administrator that created the activity or program guidelines.

In other aspects, reaction component 214 can modify/adapt prefixed avatar reactions and/or develop new avatar reactions based on the specific program, routine or activity, the determined deviation (or adherence), user profile information (e.g., user preferences, historical user behavior, user health information, etc.), user context information, and known capabilities of the avatar, using various classification (explicitly and/or implicitly trained) schemes and/or systems (e.g., rule based classification schemes, support vector machines, neural networks, expert systems, Bayesian belief networks, fuzzy logic, data fusion engines, etc.).

Processing module 210 can include inference component 216 to provide for or aid in various inferences or determinations associated with aspects of avatar guidance platform 202. In an aspect, all or portions of avatar guidance platform 202 can be operatively coupled to inference component 216. Moreover, inference component 216 can be granted access to all or portions of media provider, remote sources/systems 238, client device 106 and other sources accessible via a network 112.

In an aspect, analysis component 212 can employ inference component 216 to infer whether, how and to what degree a user deviates from a specific program, routine or activity. In association with such inferences, inference component 216 can examine determined physical and physiological activity feature values and reference physical and physiological activity feature values, determined context parameters and reference context parameters, user profile information, and other context information. In addition, reaction component 212 can employ inference component 216 to infer a response for manifestation via an avatar that facilitates adherence to a program, routine or activity. Reaction component 214 can also employ inference component 216 to infer an action a user should perform to correct a deviation from a program, routine or activity as well as a reaction for manifestation via an avatar the directs and/or motivates the user to perform the action. In association with such inferences, inference component 216 can examine deviations that have been determined/inferred by analysis component 212, information relating such deviations to predetermined avatar responses, user profile information, and user context information.

In another aspect, analysis component 212 can employ inference component 216 to infer foreseeable violations/deviations to a program, routine, or activity which the user is following. For example, where a user on alcohol addiction recover program is headed into an area with several triggers for the user (e.g., bars at happy hour time) and the user has high cortisol levels, inference component 216 can infer that the user is likely to be inclined to fall off his program and stop at a bar. Based on inferences identifying foreseeable violation/deviations, reaction component 214 can employ inference component 216 to infer mechanisms to circumvent the occurrence of the foreseeable violations/deviations and infer reactions for manifestation via an avatar to facilitate relaying these mechanisms to the user. In furtherance to the subject example, reaction component 214 can infer that a call to the user's AA sponsor and warning message would help deter the user from violating his program. Thus reaction component 214 can initiate a response for manifestation by the avatar that includes a call to the AA sponsor and a message delivered with a suitable tone of voice and facial expression warning the user not to violate his program.

In order to provide for or aid in the numerous inferences described herein, inference component 216 can examine the entirety or a subset of the data to which it is granted access and can provide for reasoning about or infer states of the system, environment, etc. from a set of observations as captured via events and/or data. An inference can be employed to identify a specific context or action, or can generate a probability distribution over states, for example. The inference can be probabilistic—that is, the computation of a probability distribution over states of interest based on a consideration of data and events. An inference can also refer to techniques employed for composing higher-level events from a set of events and/or data.

Such an inference can result in the construction of new events or actions from a set of observed events and/or stored event data, whether or not the events are correlated in close temporal proximity, and whether the events and data come from one or several event and data sources. Various classification (explicitly and/or implicitly trained) schemes and/or systems (e.g., support vector machines, neural networks, expert systems, Bayesian belief networks, fuzzy logic, data fusion engines, etc.) can be employed in connection with performing automatic and/or inferred action in connection with the claimed subject matter.

A classifier can map an input attribute vector, $x=(x1, x2, x3, x4, xn)$, to a confidence that the input belongs to a class, such as by $f(x)=confidence(class)$. Such classification can employ a probabilistic and/or statistical-based analysis (e.g., factoring into the analysis utilities and costs) to prognose or infer an action that a user desires to be automatically performed. A support vector machine (SVM) is an example of a classifier that can be employed. The SVM operates by finding a hyper-surface in the space of possible inputs, where the hyper-surface attempts to split the triggering criteria from the non-triggering events. Intuitively, this makes the classification correct for testing data that is near, but not identical to training data. Other directed and undirected model classification approaches include, e.g., naïve Bayes, Bayesian networks, decision trees, neural networks, fuzzy logic models, and probabilistic classification models providing different patterns of independence can be employed. Classification as used herein also is inclusive of statistical regression that is utilized to develop models of priority.

Avatar guidance platform 202 can further include interface component 206, avatar control component 208 and avatar generation component 226. Interface component 206 configures a graphical user interface(s) that facilitates user interaction with system 200. In particular, interface component is configured to generate a graphical user interface that includes an avatar that performs the various reactions discussed herein. The graphical user interface is presented to the user via rendering component 236 located at a client device (e.g., client device 106) employed by the user. In some aspects, the interface can provide mechanisms to select or create a program, routine or activity that a user would like to perform and have monitored via avatar guidance platform 202. The interface can further provide mechanisms for receiving input from a user related to a profile of the user and allowing the user to access and view his or her profile information. Some exemplary interfaces configured by interface component 206 in association with application of avatar guidance platform 202 to facilitate guiding a user though a fitness routine or activity are presented in FIGS. 5-7.

Avatar control component 208 is configured to evaluate a response or reaction that was determined by reaction component 214 for manifestation by an avatar presented to a user, to determine control commands to provide to avatar generation component 226 to effectuate the response by the avatar. Avatar generation component 226 is configured to generate an avatar that performs the response/reaction based on the control commands. In particular, avatar generation component 226 is configured apply the control commands to an avatar displayed to a user and generate an avatar performing the response/reaction. In essence, avatar generation component 226 is configured to generate an animation with an avatar moving, speaking, and/or appearing based on control commands received from avatar control component 208.

As previously described, in an aspect, avatar guidance platform 202 is located at the client device (e.g., client device 106) that includes rendering component 236. In another aspect, one or more components of avatar guidance platform 202 are located at a remote server (e.g., avatar server 116). For example, interface component 206, avatar control component 208, and avatar generation component 226 can be located at a remote server. According to this aspect, a user can access an interface, (e.g., using client device 106 for display at the client device) including the avatar performing various responses based on the user's input 234 via a network (e.g., at a website or other networked platform). The animation including the avatar can be provided to the client device for rendering as streaming video streamed thereto from the server. In another aspect, one or more components of avatar guidance platform 202 can be distributed between the server and the client. For example, a remote server can include the avatar control component 208 while the client device can include the avatar generation component 226. According to this example, avatar control component 208 can send the control commands to the client device via a network. Upon receipt of the control commands, the avatar generation component 226 at the client device can generate the avatar animation based on the control commands.

In an aspect, an avatar generated in association with providing guidance and instruction to a user with respect to performance of a program, routine, or activity can inform the user via visual and/or audible (e.g., speech) responses how to perform the selected activity or program prior to beginning the program/activity and/or over the course of the program/activity. For example, when the selected activity is a fitness routine, an avatar can be generated and presented to that performs at least part of the fitness routine so that the user can copy or follow the avatar. In another example, the user can have knowledge of what an activity or program requires (e.g., a diet program, a daily routine, an addiction recovery program) and an avatar generated to guide adherence to the activity or program can simply respond to the user's adherence or non-adherence to the requirements of the activity or program.

As previously noted, avatar guidance platform 202 can be employed to guide a user in association with performance of a variety of different programs, routines and activities. In one exemplary embodiment, avatar guidance platform 202 is employed to facilitate guiding a user through a fitness routine or activity. Avatar guidance platform 202 can include fitness module 230 to provide various features specific to this application. In another exemplary embodiment, avatar guidance platform 202 is employed to provide a user with a personal guide or assistant to facilitate adherence to a program or schedule. According to this embodiment, avatar guidance platform 202 can include program guide module 232 to provide various features specific to this application. Fitness module 230 and program guide module 232 are discussed in greater detail infra.

Figure 3:
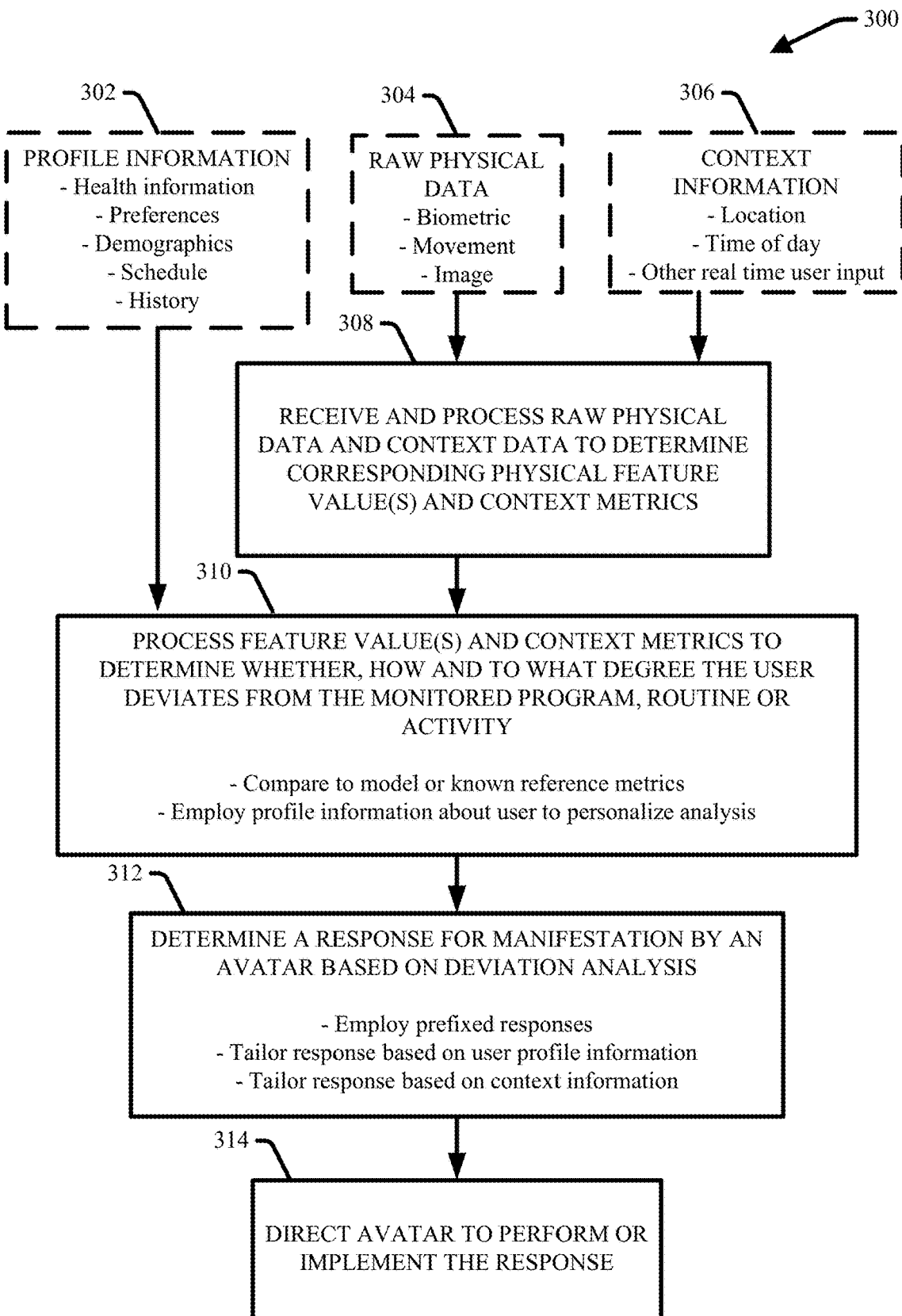
FIG. 3 illustrates a flow diagram of a process for guiding or assisting a user with adhering to a program, routine or activity using an avatar in accordance with various aspects and embodiments described herein.

FIG. 3 provides a high level flow diagram 300 of a process for guiding or assisting a user with adhering to a program, routine or activity using an avatar in accordance with various aspects and embodiments described herein. Repetitive description of like elements included in respective embodiments of systems and methods described herein is omitted for sake of brevity.

Process 300 involves receiving and processing various input data about a user's physical state and activity along with various other personal and contextual information to facilitate guiding and assisting the user with performance of a particular program, routine or activity via manifestation of responses via an avatar based on the input. In particular, at 308, raw physical data 304 and context information 306 for a user is received and processed to determine corresponding physical and physiological activity feature values and context metrics/parameters, respectively. The raw physical data 304 can include biometric data, biochemical data movement data, and/or image data captured for the user via various sensor devices attached to the user (e.g., sensor device 104) and/or various auxiliary devices (e.g. intelligent fitness device(s) 118, visual capture device 110, sensor module 112, etc.) as the user performs a specific program, routine or activity. The context information 306 can include location information (including information about the location, such as weather, events, physical structures, etc.), time of day, and other real-time user input (e.g., input provided by the user regarding the user's thoughts, feelings, desires, etc.).

For example, based on received physical and physiological data 304, at 308 various information about a user's physiological state can be determined (e.g., heart rate, blood pressure, temperature, calories burned, blood alcohol level, cortisol level, glucose level, blood oxygen level, ferritin level, LDL level, creatine kinase level, folate level, vitamin B12 level, hemoglobin level, etc.). In addition, based on received motion/movement data and/or image data over a period of time, pattern analysis can be employed to determine what physical movements the user is performing (e.g., jumping, running, performing a specific yoga pose, performing a chest press, etc.) as well as characteristic about the movements (e.g., body position, speed, pressure, intensity, etc.).

At 310, the physical and physiological activity feature values and context metrics are processed to determine whether, how and to what degree the user deviates from the monitored program, routine or activity. This processing can involve evaluation of the physical and physiological activity feature values and context metrics in view of model or reference physical and physiological activity feature metrics and/or reference context metrics for the monitored program, routine or activity. For example, this processing can include comparison of determined physical and physiological activity feature values and/or context metrics to corresponding reference metrics for the monitored program, routine or activity to determine whether, how and to what degree the user's performance and behavior deviates there from. In an aspect, this processing can involve various classification schemes and that relate different combinations of physical and physiological activity feature values to one another based on the corresponding reference metrics to determine or infer whether, how and to what degree the user deviates from the monitored program, routine or activity.

In addition to reference metrics, processing at step 310 can also involve analysis of received physical and physiological activity feature values and/or context information in view of requirements for these values in association with performance of the monitored program, routine or activity, and based on user profile information 302. This profile information can include but is not limited to: user health information, user preferences, user demographics, user schedule, and user performance history in association with the monitored program, routine or activity, and/or other monitored programs, routines or activities for the user. In some embodiments, this profile information can also include biochemical information for a user determined via one or more biological tests (e.g., a blood test, a urine test, a saliva test, a tear fluid test, etc.). According to this aspect, the physical and physiological activity and contextual requirements for a program, routine, or activity can be tailored to account for a user's physical capabilities, preferences and goals, demographics, schedule, or history. Accordingly, where two different user's perform the same routine and exhibit the same physical and physiological activity feature values, one user can be determined to deviate the program while another could be determined to adhere to the program.

At 312, based on a determination of whether, how, and to what degree a user deviates from a monitored program, routine or activity, a response is determined for manifestation by an avatar. The response is specific to the deviation (or determination of no deviation), the degree of the deviation, the program, routine or activity being monitored, the user, and potentially the context of the user. In aspect, an avatar response/reaction is determined or inferred based in part on various prefixed responses for the monitored program, routine, or activity and the particular deviation, user profile information 302 and context information 306. The response is specifically designed to provide the user with guidance in association with adhering to the monitored program, routine or activity. For example, where a user deviates from a monitored program, the response can include verbal and/or visual instruction by the avatar to command and/or motivate the user to perform an action to correct or accommodate the deviation. In another example, where it is determined that the user is properly adhering to a monitored program or activity, a response could include a showing of praise and encouragement by the avatar. In another example, where it is determined at step 310 that the user is likely to deviate from a program in the foreseeable future (e.g., by likely eating bad food based on a determination the user is located at a fast food restaurant), the response can include a mechanism to prevent the user from deviating. For example, such a mechanism could include provision of motivational coaching, alternative options, or imagery and/or external source data by the avatar that is selected to persuade the user to stick to the program.

After a response is determined at step 312, an avatar presented to the user is directed to perform or implement the response. For example, avatar generation component 226 can generate and avatar that performs the response based on control commands provided by avatar control component 208. These control commands are specifically designed by avatar control component 208 to cause the avatar to perform the determined response. For example, when the avatar response includes speaking a phrase while performing a specific movement and smiling, the control commands can direct avatar generation component 226 to generate an avatar that speaks the phrase while performing the specific movement and smiling.

Figure 4:
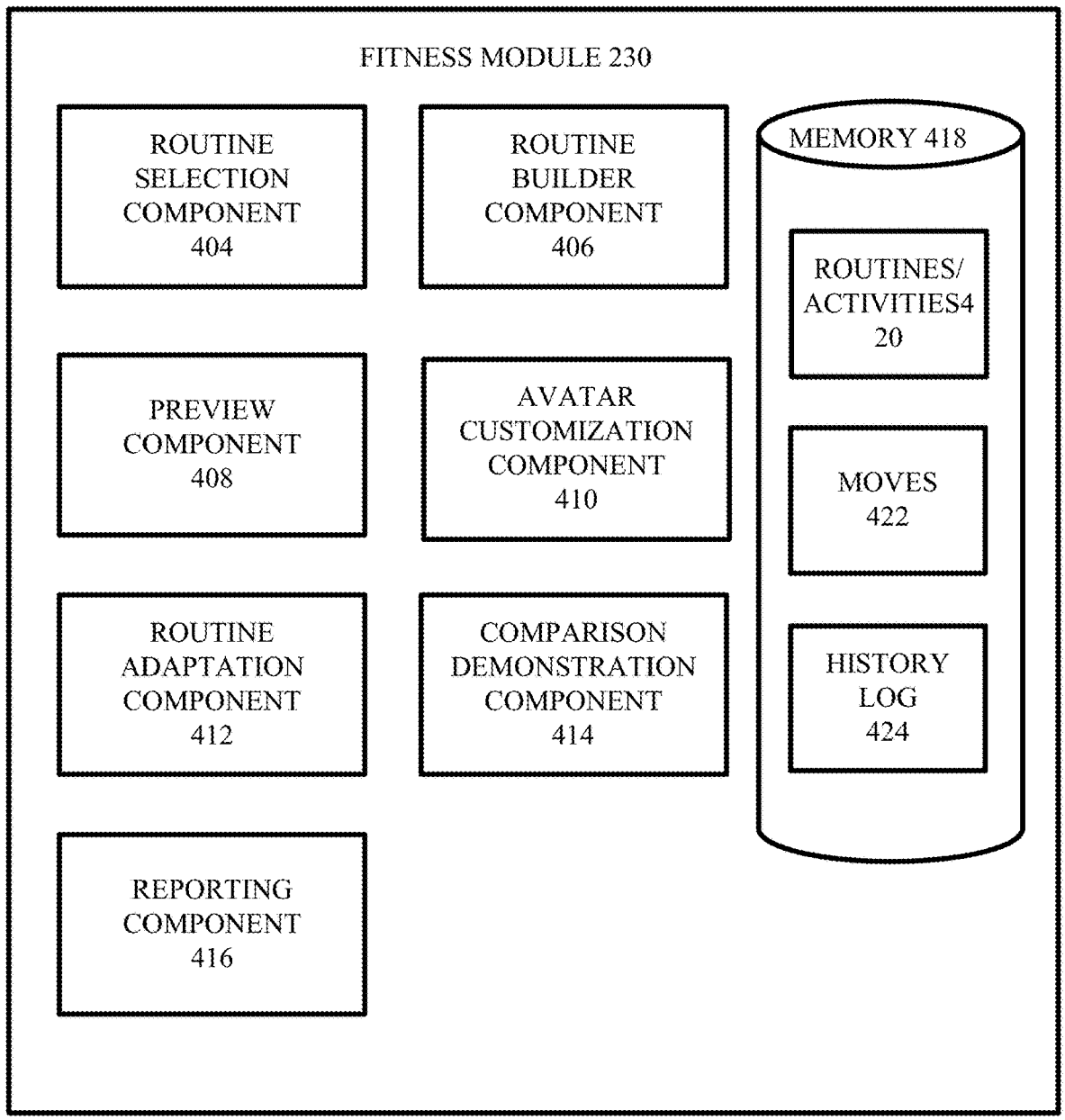
FIG. 4 illustrates an example fitness module for employment with an avatar guidance system in accordance with various aspects and embodiments described herein.

FIG. 4 provides an example embodiment of fitness module 230 in accordance with various aspects described herein. Repetitive description of like elements included in respective embodiments of systems and methods described herein is omitted for sake of brevity.

Fitness module 230 is specifically configured to facilitate guiding or assisting a user with adhering to a physical fitness routine or activity using an avatar in association with various aspects of avatar guidance platform 202. For fitness applications such as physical therapy, personal training, aerobics, performing a sports activity (e.g., gymnastics, golf, etc.), etc., the avatar plays the role of a virtual physical therapist, personal trainer or teacher. During the routine or activity, the user's physical inputs (e.g., physiological, motion, and/or image input) will automatically control the behavior of the avatar. The behavior of the avatar is designed to guide or assist the user with performance of fitness routine or activity. For example, the avatar's behavior can resemble that which a real trainer would exhibit to provide instruction, demonstration, motivation, praise, coaching, etc. throughout performance of the fitness routine/activity.

In particular, prior to, during, and after performance of a specific fitness routine or activity, a user's physical/physiological input is received by reception component 204 in accordance with aspects described herein. The user's physical and physiological activity input is further processed by analysis component 212 as it is received (in real-time or near-real) to evaluate the user's adherence to physical/physiological performance requirements of the specific fitness routine or activity, in accordance with aspects described herein. Based on this evaluation, responses/reactions are determined for manifestation by an avatar (e.g., by avatar reaction component 214), in accordance with aspects described herein. Avatar control component 208 and avatar generation component 226 then cause an avatar presented to the user to perform the response/reactions.

For example, in accordance with various aspects of avatar guidance system 200 and fitness module 230, a user can begin performance of a selected or assigned fitness routine/activity. An avatar is presented to the user (via a graphical user interface or as a hologram) to help guide the user through the routine/activity and serve as the user's coach or trainer. Depending on the selected fitness activity or routine, the avatar can be configured to perform some or all of the fitness routine with the user so that the user can mimic the movements of the avatar. In another aspect, the avatar can be configured to direct the user to perform various actions in accordance with the routine and provide demonstration of physical movements of the routine movements when necessary.

As the user performs the routine, avatar guidance platform 202 receives physical and physiological input data for the user in accordance with aspects described herein. This information, along with context data in some implementations, is evaluated as it is received to determine whether, how, and to what degree the user's performance deviates from the physical and physiological requirements of the fitness routine (e.g., as defined by physical/physiological performance metrics). For example, the user's physical and physiological data can be compared to reference information for the routine defining requirements for the physical and physiological activity data in association with performance of the physical routine (e.g., physiological metrics associated with respective movements and/or times throughout the routine, actions the user should perform to accomplish the routine, when to perform them and how to perform them with respect to range or motion, body position, intensity, etc.). Analysis of these reference metrics is further adapted based on user profile information (e.g., user physical restrictions, user physical capabilities, user demographics, preferences etc.). Analysis component 212 can also determine whether, how and to what degree the user is likely to deviate from a requirement of the fitness routine based on received physical/physiological data for the user and context data as well as profile information for the user.

For example, during performance of a physical fitness activity, information regarding a user's heart rate can be received from a heart rate monitor worn by the user. For instance, analysis component 212 can determine that the user's heart rate is 100 beats per minute. The analysis component 212 can further determine that the user deviates from the requirements of the routine based on having a heart rate below the optimal heart rate (e.g., where the routine requires a person having the height, weight and age of the user to have a heart rate of 125 beats per minute). In another example, during performance of the physical fitness activity, analysis component 212 can receive movement data identifying a form and speed of a motion being performed by the user. Analysis component 212 can further determine that the user is deviating from a physical form and speed requirement for the activity based on comparison of the received movement data to reference metrics for the routine.

In some embodiments, analysis component 212 is configured to determine or infer one or more characteristics of a physiological state or condition of the user based on received biochemical information identifying the presence or the status of the one or more biomarkers. For example, analysis component 212 can determine a level of a biomarker, a degree of severity of a physiological condition associated with a detected biomarker, or health or performance status of a particular human body system of the user. The analysis component 212 can further compare the one or more characteristics of the physiological state or condition of the user during performance of the fitness routine to reference metrics for the one or more characteristics in association with performance of the fitness routine to determine whether how and to what degree the user deviates from the requirements. For example, the reference metrics can identify a proper level for the biomarker, an acceptable range of severity of the physiological condition associated with the biomarker, or an acceptable health or performance status of the particular human body system.

For example, based on biometric and biochemical data regarding a user's muscle energy output received prior to and during performance of a fitness activity, analysis component 212 can quantify how warmed-up the user is, how much energy the user is exerting, and how fatigued the user is. Analysis component 212 can further determine whether the user's level of warm-up, energy exertion, and/or fatigue is within acceptable ranges of requirements of the fitness routine based on comparison to reference metrics for the fitness routine. In other examples, analysis component 212 can determine based on received biochemical data, whether a user's electrolytes are too high or too low, whether a user is experience inflammation above a desired level, whether a user is becoming exhausted, whether the user's hydration level is too high or too low, whether the user's V02 max is at a desired level, etc.

After analysis component determines whether, how, and to what degree a user deviates and/or is likely to deviate from a physical/physiological and/or contextual requirement of a physical fitness routine or activity, reaction component 214 determines a reaction for an avatar presented to the user that is designed to either correct the deviation, praise the user for not deviating, and/or encourage the used to avoid a possible deviation before it occurs. The reaction will vary based on the particular physical fitness routine/activity being performed, the predefined physical/physiological and/contextual requirements of the routine/activity, and the personal capabilities, preferences, goals, and health status/history of the user. In general, the reaction is intended to guide or encourage optimal performance of the physical fitness routine by the user.

In some embodiments, reaction component 214 can determine an action for performance by the user that has been previously determined to correct or prevent a particular deviation to a physical fitness routine. For example, the action can be previously determined to correct or prevent the particular deviation to the physical fitness routine based on proven scientific research or learned user behavior (e.g., via machine learning or otherwise). In an aspect, reaction component 214 can determine the action based the specific physical routine, the type of deviation and degree of the deviation, prefixed responses for the routine and deviation, user profile information and potentially context information.

Suitable reactions to deviations in physical movement and/or motion requirements (e.g., form, range of motion, speed, reaction time, etc.) of a fitness routine/activity can include specific physical changes to the user's form, range, of motion, speed, reaction time, etc., that correct the physical movement/motion deviation. For example, in response to a determination that a user is performing push up with improper form, analysis component 212 can determine that the user should either be instructed to correct the form or perform a modified push up with his or her knees on the floor.

Suitable actions that can correct observed deviations based on physiological data (e.g., biometric/biochemical) can include but are not limited to: a modification to a manner of a physical movement, intensity of the movement, or speed of the movement, a direction to perform a specific physical exercise at a specific intensity, speed, range of motion, etc., repetition of particular exercise, stopping of a particular exercise, resting, stretching, drinking water, ingesting a food or dietary supplement, ingesting a particular drug, or applying a therapeutic treatment such as an ice treatment or a heat treatment. For example, in response to a determination that a user's hear rate is below a desired level during performance of a plyometric routine, analysis component 212 can determine that the user should increase the duration of a specific movement of the plyometric routine by 15 seconds. In another example, in response to a determination that a user's quadriceps are becoming fatigued beyond an acceptable level during a squat press exercise, analysis component 212 can determine that the user should reduce a weight load employed during performance of the exercise. In yet another example, in response to a determination that a user is becoming dehydrated or his or her electrolytes re lowering beyond a desired level during performance of a marathon, analysis component 212 can determine that the user should ingest a high electrolyte fluid supplement.

According to these embodiments, the action can be standardized for all users or personalized based on specific physical/physiological characteristics and demographics of the user (e.g., age, weight, height, BMI, etc.). The action can also be tailored based on a user's personal preferences, capabilities and physiological/physical status or condition. According to this aspect, reaction component 214 can personalize an action for performance by a user that is designed to prevent or correct a physical/physiological deviation to a fitness routine based on biochemical information received for the user before or during performance of the fitness routine. For example, based on received biochemical information for a user indicting the user is experiencing muscle soreness/fatigue in his quadriceps prior to beginning a fitness routine, reaction component 214 can determine physical modifications to enhance the user's performance of the fitness routine that do not involve heavy exertion of the quadriceps.

Further, the action can be tailored based on a user's current context. For example, reaction component 214 can take into consideration a user's, location, services and equipment available at the location, food/water and dietary supplies available, weather at the location (e.g., when the location is outdoors), time of day, etc. For example, during performance of fitness routine outdoors at a facility that involves a pool, in response a determination that a user is becoming overheated, reaction component 214 can determine that a suitable response includes performance of recovery exercise in the pool.

Reaction component 214 is further configured to determine a reaction or response for performance by an avatar presented to the user based on a determination of whether, how and to what degree a user has violated or is likely to violate a physical/physiological and/or contextual requirement of a monitored fitness routine/activity. For example, in response to a determination that a user has not and is not likely to deviate from a requirement of the fitness routine/activity, reaction component 214 can select a praise or encouragement avatar reaction. Likewise, in response to a determination that a user is likely to deviate, reaction component 214 can select an avatar reaction that prevents the user from performing the deviation. Similarly, in response to a determination that a user is deviating from a requirement of the routine, reaction component 214 can determine a reaction for an avatar that helps the user to correct the deviation and/or minimize the impact of the deviation.

Avatar control component 208 and avatar generation component 226 can then cause the avatar to perform the reaction. For example, the avatar reaction can include visual and/or audible reactions in the avatar, including but not limited to: a vocal command, a behavior, a physical movement or demonstration. When providing vocal commands and/or gestures/movements, the avatar can react with a specific tone of voice, inflection, facial expression, body language, etc., that a real human would in order to convey the information intended by the reaction. In some aspects, the reaction can include initiation of electronic communication (e.g., sending a notification, initiating an emergency call), and provision of external media (e.g., images, articles, a map, videos, songs, etc.) to the user to facilitate guiding the user with adherence to the program.

In some implementations, the avatar reaction can be selected by reaction component 214 from a set of predefined avatar reactions. The predefined avatar reactions can be respectively associated with a specific type and/or degree of deviation, and/or a specific action, (determined by reaction component 214) for performance by a user based on a determination regarding whether, how, and to what degree the user is or is likely to deviate from the physical fitness routine/activity. Characteristics about the avatar reaction (e.g., tone of voice, facial expression, body language, volume of voice, sources of external data employed for motivation, etc.) can also be tailed or personalized for a particular user (e.g., based on the user's profile, preferences, learned behavior of the user, goals of the user, etc.).

For example, in order to encourage the user to increase his heart rate, an avatar presented to the user can visually increase the pace of the motion being performed by the user, provide verbal instruction to increase speed, or a provide a visual or audible indicator that increases the rhythm of the motion to encourage the user to match the pace. For instance, when performing alternating lateral lunges (mimicking the motion of speed skating as they are also known) when moving side to side, one's heart rate should increase. If the target heart rate is not met, the speed at which an avatar demonstrating the exercise is lunging side to side will increase until the targeted heat rate is met. Conversely, if the user's heart rate exceeds the target zone, the avatar will slow down until the user's heart rate also drops. In another example, the avatar can change aspects (e.g., the rhythm, the song, the volume, etc.) of music playing to motivate the user to increase his pace.

In addition to improving or optimizing a user's physical performance of a physical fitness routine/activity, by customizing and automatically responding to changes in the user's physical/physiological data, the avatar guidance system 200 promotes user safety during physical exercise and prevents injury. In particular, the avatar guidance system 200 is configured to respond to user input automatically and in real-time, thereby providing indication of a potentially dangerous activity in advance of an unsafe result. For instance, if the system recognizes certain metrics as leading to bodily harm, the system can instruct the avatar to stop the workout session and contact a health professional or automatically send a notification (e.g., a call, electronic message, etc.) to the health professional. If necessary, the system can additionally or alternatively be configured to contact emergency services, thus saving precious time in the event of a severe or potentiality life threatening injury.

To provide for various aspects of avatar guidance system 200 when applied to facilitate a fitness routine or activity, fitness module 230 can include routine selection component 404, routine builder component 406, preview component 408, avatar customization component 410, routine adaptation component 412, comparison demonstration component 414 and reporting component 416. Fitness module 230 can also include various data objects stored in memory 418 (which can be inclusive of memory 218) that are specific to aspects of fitness module. These data objects can include information defining various fitness routines/activities 420 and activities capable of being monitored by fitness module 230, information defining various fitness movements or moves 422 capable of being performed by an avatar in association with a fitness routine or activity, and historical information for respective users logging their performance of fitness routines or activities using fitness module 230.

Routine selection component 404 is configured to allow a user of fitness module 230 to select a preconfigured fitness routine or activity to perform from a database of routines/activities 420. Each of these routines or activities has a defined set of physical moves and requirements for the user to perform. For example, the routine or activity can include an aerobics routine, a physical therapy session, a strength training exercise, a yoga routine, a dance routine, a golf exercise, a running workout, a biking workout, kickboxing workout, etc. The routine or activity can be designed for performance in a fixed space indoors or outdoors, over changing indoor or outdoor terrain, and/or using various equipment or apparatuses.

In another aspect, rather the selecting a stock fitness routine or activity to perform, routine builder component 406 can facilitate designing a custom routine for the user to perform. In an aspect, routine builder component 406 can allow the user (or a supervisor of the user), to build a custom fitness routine or activity by selecting various fitness moves to include in the routine or activity and selecting physical and physiological activity parameters associated with performance of the fitness moves. For example, using a database of a plurality of known physical movements capable of being performed by a human in association with a wide variety of fitness activities (e.g., moves database 422), the user can pick and chose various moves and/or combinations of moves to include in a fitness routine. For instance, when designing an aerobics routine, the user can select different aerobics moves can combinations of moves from a database of possible moves. In association with selecting moves, the user can also select characteristics associated with performance of the moves, such as intensity, duration, frequency, range of motion, speed, etc. For example, when designing a strength training routine, the user can select what weight lifting movements to perform, weight to employ for each movement, number of repetitions, number of sets, range of motion, etc.

Still in yet another aspect, routine builder component 406 can be configured to design a custom fitness routine or activity for a user based on the user's needs, desires, physical abilities and context. In particular, routine builder component 406 can design a customized fitness routine or activity for a user to perform based on user profile information including but not limited to: information describing the user's demographics, physical profile (e.g., height, weight, physical abilities, physical injuries or restrictions, etc.), physiological profile (e.g., biochemical/biometric information about a physiological state/status of the user, including presence and levels of various biomarkers), preferences (e.g., what types of activities the user prefers or dislikes), goals (e.g., fitness activity performance goals, weight loss/gain goals, muscle building goals, etc.), and a monitored physical performance history, (e.g., history of fitness routines/activities the user has completed and summary of the user's performance). For example, based on user profile information, routine builder component 406 can design a customized routine for the user to perform that includes moves the user is capable of safely performing, moves the user prefers, moves that will challenge the user and facilitate achieving the user's goals, moves that the user did not perform yesterday, etc.

In addition, avatar customization component 410 can analyze context information when designing or selecting a customized routine or activity for a user to perform. For example, avatar customization component 406 can consider the user's location, the time of day, the amount of time available to the user, the current weather associated with the location, and fitness equipment/apparatuses available to the user. In an aspect, in association with designing a customized routine for a user, routine builder component 406 can receive user input providing some desired characteristics for the routine. For example, the user can provide information regarding a type of activity the user would like to perform that day, (e.g., cardio, weight training, yoga, kickboxing, running/biking outside, etc.), one or more muscle groups the user would like to work on, the desired duration of the activity.

In an aspect, an avatar generated and presented to a user in association with performance of a fitness routine or activity can perform the movements of the fitness routine or activity. While designing a fitness routine or activity and/or prior to performing a fitness routine or activity, the user may desire to see a demonstration of one or more of the physical moves required by the activity. Preview component 408 is configured to generate an avatar that demonstrates one or more moves selected for inclusion in a fitness routine or activity prior to beginning performance of the routine or activity. For example, a user can select a stock routine or activity and/or select a custom routine that has been designed for the user (e.g., automatically by routine builder component 406) and then select preview component 408 to be presented with an avatar that demonstrates one or more of the moves included in the selected routine or activity. Based on the preview, the user can decide whether or not to proceed with performance of the selected routine or activity.

In another aspect, while designing a custom fitness routine or activity, the user can view an avatar demonstrating a chosen move or combination of moves based on the requirements selected for the move or combination of the moves (e.g., speed, intensity, range of motion, etc.). For example, the user can select a series of yoga poses to include in a yoga routine and the select preview component 408 to view the series of yoga poses being performed by an avatar. If the user is unsatisfied with the manner in which the poses flow based on the preview, the user can change aspects of the selected pose series. In an aspect, when viewing the previewed demonstration of a fitness move or moves, preview component 408 can allow the user to change the perspective of view of the avatar. For example, the user can rotate a virtual camera pointed at the avatar to various viewpoints (e.g., 360° with respect one or more axis) of the avatar so that the user can view the avatar's body position during performance of the fitness move from various points of view.

Avatar customization component 410 allows a user to customize the avatar presented to the user to facilitate a fitness routine or activity. In an aspect, avatar customization component 410 can allow the user to manipulate variables to create an avatar that reflects the needs and tastes of the user. In particular, using avatar customization component 410, a user can select the avatar's appearance, demographics, voice and personality. For example, the age, gender, language or accent, dress, or other visual and/or audio characteristic of the avatar may be selected to motivate and/or comfort the user. In another aspect, avatar customization component 410 can provide predetermined character personas for the user to select and apply to his or her avatar. For example, the avatar can be selected from a familiar character set that includes known cartoon characters or people (e.g., famous actors, musicians, politicians, athletes, etc.) where such characters creators or persons have authorized usage of their persona. For example, a cartoon avatar may be suitable to lead a child user through an exercise regime, or a popular athlete or fitness trainer may motivate an adult user to adhere to a fitness program.

In another aspect, avatar customization component 410 can automatically design an avatar to facilitate a user with a fitness routine or activity. According to this aspect, avatar customization component 410 can select the avatar's appearance, demographics, voice and personality based on one or more of: the fitness routine or activity selected for performance, profile information for the user regarding the user's preferences, the user's demographics, and the user's performance history with respect to monitored fitness routines or activities. For example, based on analysis of the user's preferences and demographics, avatar customization component 410 can determine or infer what type of avatar in terms of appearance and personality would best facilitate/motivate the user in association with performance of a selected fitness activity or routine (e.g., based on data relating avatar appearance and character traits to various aspects of user profile information).

In an aspect, an avatar configured to facilitate performance of a fitness routine or activity is configured to perform the fitness routine or activity so that the user can mimic the avatar. For example, a selected fitness routine or activity has known movements and requirements that can automatically control the movements of the avatar. In another aspect, avatar customization component 410 can allow a user to select the manner and degree to which the avatar performs the moves of a fitness routine or activity. For example, using avatar customization component 410, the user can select the degree of physical demonstration and instruction the user would like his or her avatar to provide. According to this example, the user could select full performance mode wherein the avatar is configured to perform the fitness routine or activity in full, or partial performance mode wherein the avatar is configured to perform parts of the routine or activity (e.g., provide a short demonstration of each new movement of a fitness routine or activity, provide demonstration of a move during a fitness routine or activity only upon request of the user during the course of the routine or activity, etc.). In another example, the user could select instruct mode wherein the avatar is configured to provide only verbal instruction regarding performance of a fitness routine or activity with the exception of a physical movement demonstration reaction determined by reaction component 214. In another example, avatar customization component 410 can allow the user to select correction mode wherein the avatar is configured to only demonstrate a move when the user performs it improperly.

Routine adaptation component 412 is configured to dynamically adapt aspects of a fitness routine or activity being performed by a user based on received physical and physiological activity for the user (prior to, during, or following performance of the fitness routine/activity), user profile information (e.g., including in some aspects, information regarding a physiological state or condition of the user based on biochemical information), and potentially user context information. For instance, in some aspects an avatar's reaction to user performance deviating from a fitness routine or activity includes a visual or verbal cue to help or motivate the user correct the deviation. For example, when a user is moving too fast or too slow, the avatar's reaction is designed to cause the user to slow down or speed up, respectively. In other aspects, an avatar's reaction to user performance adhering to the fitness routine or activity (e.g., the user is performing the routine correctly with respect to physical and physiological activity requirements of the routine) is designed to simply provide praise to the user and encourage the user to keep up the good work.

However, in various additional aspects, an avatar's response to a user's performance deviating from or adhering to a fitness routine or activity can involve adaptation of requirements of the routine or activity, changing of the fitness routine or activity, and/or stopping of the fitness routine or activity. For example, in some situations where a user's physical and physiological activity performance is below standard, rather than pushing the user to improve his or her performance, it may be more appropriate to have the user to take a break and rest, stop performance altogether (e.g., where physical and/or physiological input indicates the user is at risk for physical injury), have the user perform an easier version of the fitness routine, or have the user perform an different routine or physical activity. In another example, in situations where a user's physical and physiological performance is above standard and/or consistently on point, rather than merely praising the user for the good performance and encouraging the user to keep it up, it may be more appropriate to increase the intensity or difficulty level of the fitness activity or have the user advance to a new fitness activity that focuses on a new muscle group or skill set.

According to this aspect, fitness module 230 can include routine adaptation component 412. Routine adaptation component 412 is configured to dynamically determine whether and how to adapt or change the physical and physiological activity requirements of a fitness routine or activity during performance of the fitness routine or activity by a user, and/or whether and how to change the fitness routine or activity being performed by the user during performance of the fitness routine or activity be the user. In response to a determination to adapt a fitness routine or activity during performance of the fitness routine or activity by the user, routine adaptation component 412 can direct processing module to evaluate the user's performance based on the adaptation (e.g., new physiological and/or motion or pressure reference metrics). In addition, routine adaptation component 412 and/or reaction component 214 can determine a reaction for manifestation via the avatar to inform the user regarding the adaptation and facilitate performance of the routine by the user with the adaptation. This determined reaction can be then be automatically effectuated by avatar control component 208 and avatar generation component 226 during performance of the fitness routine or activity by the user.

In an aspect, routine adaptation component 412 is configured to make determinations regarding whether and how to adapt a fitness routine or activity based on analysis of a degree, consistency and frequency of a deviation or non-deviation during performance of the routine (e.g., with respect to degree, consistency and frequency thresholds for the deviation in association with performance of the routine), user profile information and/or context information. For example, routine adaptation component 412 can be configured to adjust the requirements of a fitness routine or activity based on consistent performance of the fitness routine or activity below standard performance, above standard performance, or at standard performance, wherein consistency is evaluated based on reference metric thresholds for frequency and duration of the deviation or non-deviation and/or degree of the deviation. For example, where a user consistently performs below the required amount of reps on a weight machine, routine adaptation component 412 can determine that the amount of reps and/or weight should be lowered. In another example, where a user continually throws farther than a required distance, routine adaptation component 412 can determine that the required distance should be increased. In yet another example, where a user consistently performs a fitness move at a required intensity yet does not have an increase in heart rate, routine adaptation component 412 can determine that the required intensity of the fitness move should be increased.

In another example, routine adaptation component 412 can determine whether and how to adapt various aspects of a physical routine or activity being performed by a user based on biochemical information regarding a physiological state or condition of the user prior to and/or during performance of the physical routine or activity. For example, prior to beginning a fitness routine or activity, a user can provide biochemical information (e.g., via an implanted biosensing device, a worn biosensing device, an external biosensing device, user input following an at home biosensing testing result, etc.) regarding a biochemical state of the user. As discussed supra, this information can include for example, information regarding the presence and/or concentration of various biomarkers, physiological conditions/diseases associated with the presence and/or concentrations of the respective biomarkers, quality of health/functional status of various human body systems and organs, and susceptibility to various diseases or physiological/physical conditions. For example, based on received biochemical information for a user, analysis component 212 can determine information regarding a user's energy level, fatigue level, inflammation level, dehydration level, hunger level, electrolyte level, or metabolic state.

Based on biochemical information received for a user prior to beginning a workout, routine adaptation component can be configured to adapt various aspect of the workout to account of the user's physiological state/condition as determined based on the biochemical information. For example, routine adaptation component 412 can adjust the intensity of the workout, the particular exercises to be included in the workout, the range of motion of the exercises, the number or reps or amount of weight for the respective exercises, a speed of the workout a duration of the workout, etc. Routine adaptation component 412 can similarly adapt physical fitness routine or activity during performance of the routine/activity to account for similar biochemical feedback received for the user during the workout (e.g., via the implanted, worn, or external biosensing devices employed herein).

Routine adaptation component 412 can also base a determination regarding adjustment of requirements of a fitness routine or activity based on user profile information, including but not limited to: historical performance of the user in association with performance of monitored fitness routines or activities, goals of the user, current physical state of the user, preferences of the user, and/or physical capabilities and limitations of the user. For example, where it is determined that a user is consistently completing reps on a weight machine at a required weight and the user has previously been able to lift more weight (in a past workout), routine adaptation component 412 can adapt the requirements of the routine to increase the number of reps and/or weight. In another example, where a user is continually nailing performance of a certain yoga pose during performance of a selected yoga routine, routine adaptation component 412 can change the selected yoga routine to include a more advanced pose. When selecting the more advanced pose, routine adaptation component 412 can consider poses that are safe for the user to perform in light of a known back injury and certain yoga poses that the user prefers or does not prefer. In yet another example, when a user is becoming extremely fatigued during a cardio aerobics routine based on consistent performance below the physical and physiological activity requirements of the routine, routine adaptation component 412 can adjust the intensity requirements of the aerobics routine by including easier moves the user prefers or change a muscle group focused on (e.g., from legs to abdominals) based on knowledge that the user has not worked the new muscle group in over a week.

Routine adaptation component 412 can also consider contextual information when determining whether and how to adjust requirements of a fitness routine or activity during performance of the fitness routine or activity. For example, when a user is running outside and the temperature increases by N degrees, routine adaptation component 412 can adjust the required speed or duration of the run to accommodate for the intensity increase associated with the rise in temperature. In another example, during performance of a fitness activity, the user may provide feedback stating 'this is too hard,' or 'this is too easy.' Based on such feedback and information regarding whether and to what degree the user is deviating from the requirements of the fitness activity, routine adaptation component 412 can determine whether and how to adjust the requirements of the fitness activity.

In response to a determination by routine adaptation component 412 to change the requirements of a fitness routine or activity (e.g., change the speed, intensity, exercise move, range of motion, difficulty level, muscle group worked, etc.) and/or change the fitness routine or activity all together (e.g., stop performance or select a new routine or activity for performance by the user), routine adaptation component 412 can adapt the requirements of the routine accordingly. As a result, adherence to the fitness routine or activity will be evaluated (e.g., by analysis component 212) based on the adapted requirements. In addition, the avatar presented to user can provide a visual and/or audible response that informs the user regarding the adaptation. In particular, based on a change to a fitness routine or activity determined by avatar adaptation component 412, routine adaptation component 412 and/or reaction component 214 can determine a reaction/response for manifestation by the avatar that informs the user regarding the change and/or facilitates performance of the routine with the change. This reaction can involve a verbal cue informing the user about the change and/or a physical demonstration by the avatar of the routine or activity with the change.

For example, the avatar can demonstrate a new move or demonstrate a move at a different intensity while informing the user how to perform the new move or the move at the different intensity level. In some aspects, when an avatar is configured to perform the fitness routine for the user to mimic (e.g., an aerobics routine), the avatar can perform the fitness routine as adapted by routine adaptation component 412. For example, while performing a selected fitness dance routine, the avatar can dynamically change the moves, intensity of the moves, music associated with the routine, etc. over the duration of the routine based on determinations by routine adaptation component 412.

In an aspect, fitness module 230 can include reporting component 416 to provide real-time feedback regarding a user's performance of a fitness routine or activity to a remote entity, such as the user's human physical trainer or therapist at a remote location. For example, reporting component 416 can communicate any information received and/or processed by avatar guidance system to a remote entity via network as it is received and/or determined (e.g., in real-time). This information can include input 234 (e.g., raw physical and physiological activity data, user profile information, context information) received by avatar guidance platform, determinations regarding adherence or deviation from a fitness routine or activity performed by a user, and determined/manifested avatar responses.

The remote entity can also communicate with avatar guidance platform 202 during performance of the fitness routine or activity by the user. Therefore, in an aspect, rather than having routine adaptation component 412 automatically determine and effectuate changes to a fitness routine or activity as the user performs it, a remote entity can determine such changes based on received information. The remote entity can further communicate the changes to routine adaptation component 412 and routine adaptation component 412 can effectuate the changes determined/requested by the remote entity. In particular, based on the changes to a fitness routine determined and communicated to fitness module 230 by the remote entity, adherence to the fitness routine or activity will be evaluated (e.g., by analysis component 212) based on the changes. In addition, the avatar presented to user can provide a visual and/or audible response that informs the user regarding the adaptation. In particular, based on a change to a fitness routine or activity determined by the remote entity, routine adaptation component 412 and/or reaction component 214 can determine a reaction/response for manifestation by the avatar that informs the user regarding the change and/or facilitates performance of the routine with the change.

Comparison demonstration component 414 is configured to generate a comparison visualization between an avatar performing a correct demonstration of a fitness move and a representation of the user (e.g., in an avatar form or a video replay of the user) as the user performed the move incorrectly. For example, if the user repeatedly performs a move incorrectly, avatar comparison component 414 can generate a second avatar configured to perform the move in the manner in which the user performed it incorrectly (e.g., based on motion data and/or image data collected for the user). In another aspect, the avatar comparison component 414 can collect video footage of the user as the user performed the move incorrectly. Comparison demonstration component 414 can then generate a side by side comparison visualization of an avatar performing the move correctly and another avatar representing the user (e.g. or the video footage of the user) performing the move incorrectly. Thus, a side by side comparison of the user's own actions and the virtual personal trainer model technique can be displayed.

FIG. 5 presents an example user interface 500 that facilitates receiving user profile information in association with employment of avatar guidance system 200 for physical fitness purposes in accordance with various aspects and embodiments described herein. Repetitive description of like elements included in respective embodiments of systems, methods and interfaces described herein is omitted for sake of brevity.

In an aspect, a user can establish a profile with avatar guidance system 200 that includes a variety of personal information related to the user and the user's usage of avatar guidance system 200. For example, when employing avatar guidance system 200 for fitness and health related purposes, a user can be presented with interface 500 to facilitate establishing a user profile and entering personal information related to the user's health and fitness profile. For instance, interface 500 include can information section 502 that facilitates receiving user input regarding the user's physical profile, the user's physical limitations, and the user's dietary restrictions. Interface 500 can also include section 504 that presents an interactive pictorial representation of a human with the various muscle groups displayed. In an aspect, using this section the user can select body parts and/or muscle groups to indicate where the user has injuries and/or physical limitations.

Figure 6:
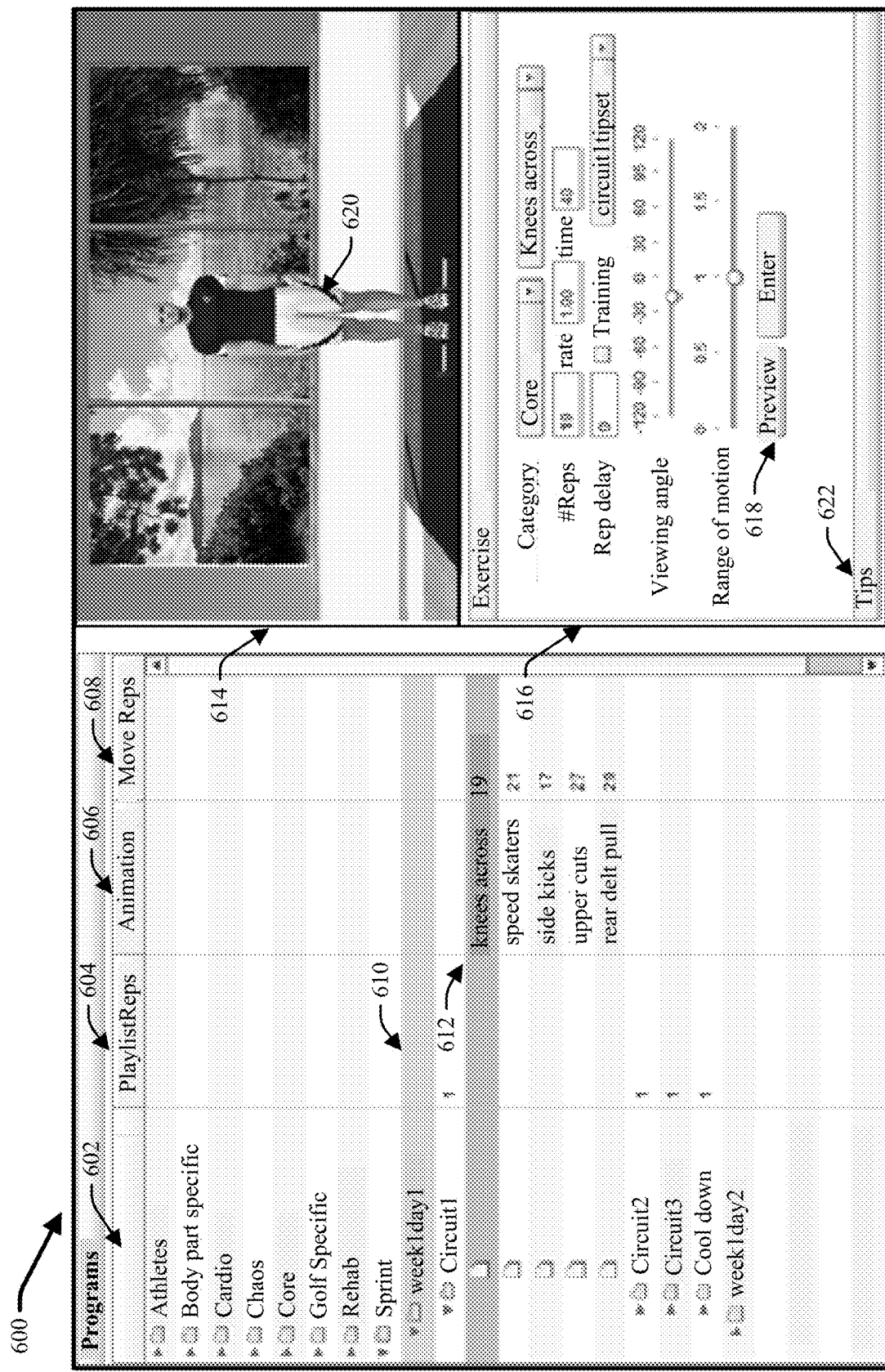
FIG. 6 presents an example user interface that facilitates designing a custom fitness routine in association with employment of an avatar guidance system for physical fitness purposes in accordance with various aspects and embodiments described herein.

FIG. 6 presents an example user interface 600 that facilitates designing a custom fitness routine in association with employment of avatar guidance system 200 for physical fitness purposes in accordance with various aspects and embodiments described herein. Repetitive description of like elements included in respective embodiments of systems, methods and interfaces described herein is omitted for sake of brevity.

In various aspects, a user or an authorized supervisor of the user (e.g., the user's fitness trainer, physical therapist, doctor, parent, etc.), can design a custom workout to perform and have guided by an avatar presented to the user. For example, the user can design an exercise routine with various selected moves and characteristics and requirements for the moves, such as number of repetitions, time between repetitions, duration, frequency, range of motion, intensity, etc. Accordingly, the user can select/manipulate various variables to create a workout program specifically designed to match a user's needs, preferences, physical limitations, and goals.

Interface 600 provides an example tool for designing a fitness routine in accordance with aspects described herein. The left side of the interface includes column 602 which includes a plurality of different menu categories to select in association with designing a custom workout. In an aspect, column 602 provides the capability to choose a type of workout desired from a plurality of different menu options that correspond to categories of workout types, such as body part specific, cardio, chaos, core, golf specific, rehab, etc. For example, the 'sprint' workout category is selected in example interface 600. The user can further customize various aspects of a selected workout using various potential sub-category options available via a drop down menu from a selected menu category of column 602. These sub-categories can vary depending on the workout category selected. For example, these sub-categories can correspond to different parts of a workout (e.g., warm up, cool down, high intensity portion, cardio portion, etc.), different machines/tools or weights used in association with the workout, different rounds or circuits of a workout, etc. In another example, these sub-categories can correspond to information regarding when the workout is to be performed in association with a workout program. In other aspect, the user can define sub-categories of a workout type menu category.

As exemplified in interface 600 the user has selected the 'sprint' workout for week 1 day 1 and week 1 day 2 of a workout program. The sub-category week 1 day 1 is currently selected (as indicated by highlighted column 610). This sub-category includes additional drop-down sub-categories corresponding to different parts of the workout, including circuit 1, circuit 2, circuit 3 and cool down. The user can select each of the part of the workout and define exercise moves (and characteristics of the exercise moves) to include therein. For example, with respect to circuit 1, the user has selected the following exercise moves: knees across, speed skaters, side kicks, upper cuts and rear delt pult. In column 604, the user can select the number of repetitions to complete for the respective parts of the workout. For example, each of circuit 1, circuit 2, circuit 3 and cool down are selected for repeating once (as indicated by the number 1 next to each part of the workout under column 604.

Column 606 corresponds to animation. In particular, a description of the selected exercise move appears in column 606 to indicate what the move is at it will be demonstrated by an avatar presented to the user. Additional information describing how the animated avatar will appear when demonstrating the move in accordance with the defined characteristics of the move (e.g., speed, range of motion, etc.) can also be included in column 606. Column 608 corresponds to the number of exercise moves reps selected for completion. For example, the user has selected to perform 19 repetitions of 'knees across.'

In an aspect, section 616 of interface 600 facilitates defining various characteristics of a selected exercise move and section 614 provides a video animation demonstration of an avatar 620 performing the selected exercise move in accordance with the selected characteristics. For example, on the left side of the interface, the 'move knees across' exercise is currently selected (as indicated by highlighted row 612). Using section 616, the user define the various requirements for the exercise 'knees across,' such as number of repetitions, rate of the repetitions, time to complete the repetition, amount of time delay between repetitions, whether the exercise is a training exercise, range of motion, speed of the exercise, etc. It should be appreciated that a variety of different feature requirement selections can be provided in section 616 (e.g., heart rate, blood pressure, speed, etc.) which can also vary depending on the selected exercise.

After a user has selected specific requirements for an exercise in section 616, the user can select the preview button 618 to see a preview demonstration of the avatar 620 displayed in section/window 614 performing the exercise in accordance with the specified requirements. In an aspect, as the user previews the avatar 620 performing the exercise, the user can change the viewing angle at which the avatar is displayed (e.g., of a virtual camera pointed at the avatar 620) to see how the movements are demonstrated from different views of the avatar. For example, depending on the demonstrated exercise, a side or front view may provide a more helpful perspective of the avatar model. In addition, section 616 includes a tips category 622, wherein the user can provide personalized tips, instruction, or messages to be provided to the user (e.g., in an audible format, spoken by the avatar, etc.) when the user performs the exercise. For example, the user can provide a description of what the move is, how to perform the move correctly, what not to do when performing the move, a motivational quote, etc.). These tips can be configured for rendering to the user (e.g., in an audible format, spoken by the avatar, etc.) when the user performs the specific exercise move during the workout.

Figure 7:
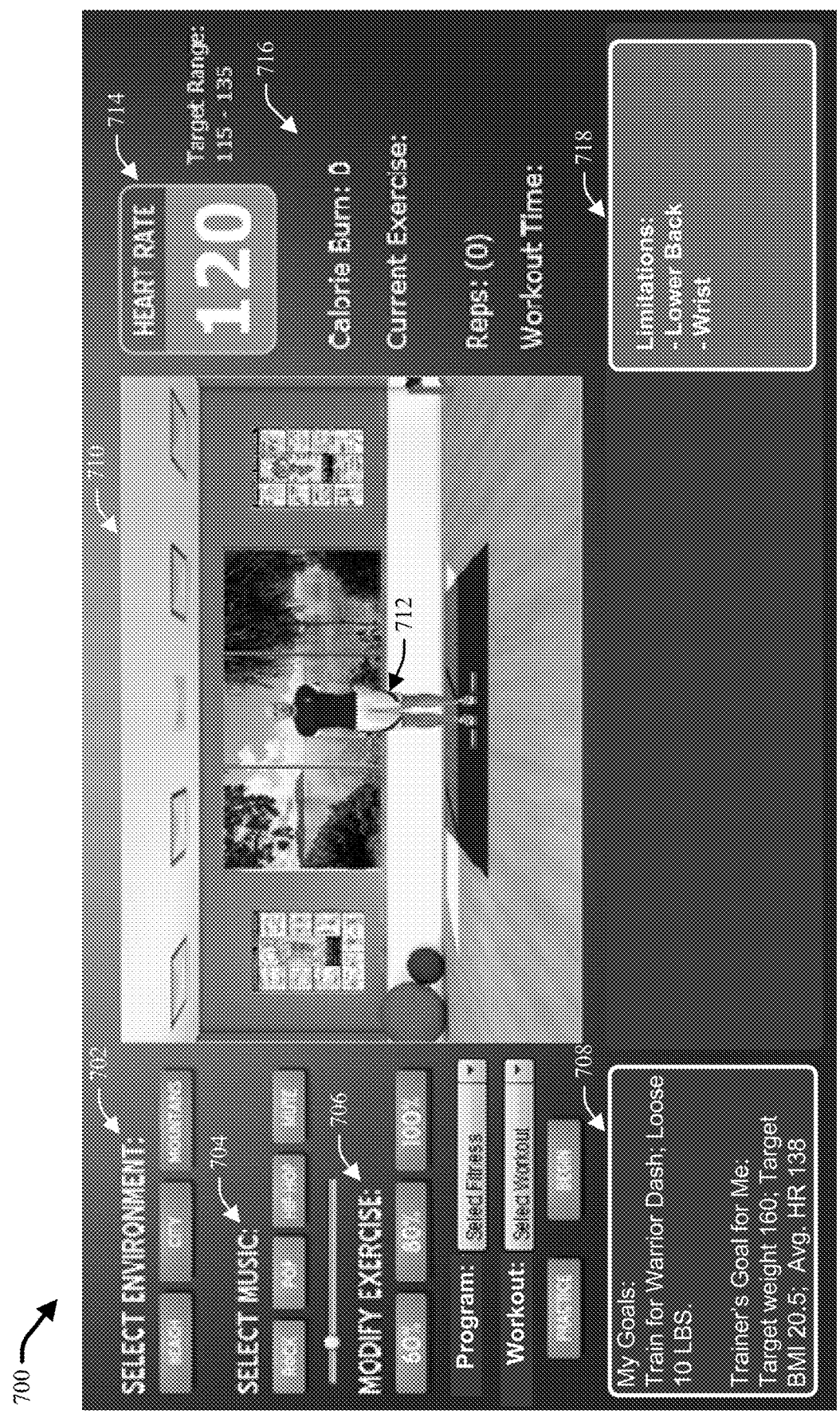
FIG. 7 presents an example user interface that presents a user with an avatar to facilitate guiding the user through a selected fitness routine in accordance with various aspects and embodiments described herein.

FIG. 7 presents an example user interface 700 that presents a user with an avatar to facilitate guiding the user through a selected fitness routine in accordance with various aspects and embodiments described herein. Repetitive description of like elements included in respective embodiments of systems, methods and interfaces described herein is omitted for sake of brevity.

In an aspect, interface component 206 can generate interface 700 for presentation to a user (e.g., via rendering component 236) during performance of a selected fitness routine or activity. Interface 700 includes an avatar 712 displayed within a workout space 710. The appearance of the avatar and/or the workout space are customizable (e.g., via avatar customization component 410). In an aspect, as described above, the avatar 712 is configured to function as the user's personal trainer and provide instruction to the user regarding performance of the selected fitness routine. In particular, the avatar 712 is configured to respond in real-time to physical and physiological activity input received for the user as the user performs the fitness routine in accordance with aspects described herein. For example, as the user performs a fitness routine, the avatar 712 can provide various real-time reaction to the user's performance based on received and analyzed physical and physiological activity data for the user (e.g., in accordance with aspects described herein). For instance, the avatar can call out commands, tell the user how to correct certain physical deviations from the routine (e.g., based on physiological data and/or movement data for the user), provide physical demonstration of moves, motivate the user with facial and body movement expression, etc. As described above, these reactions can be specifically tailored to the user's personal tastes, goals and abilities (e.g., based on user profile information) and/or the user's current context (based on received context information). In some aspects, the avatar 712 is configured to perform the fitness routine for the user to follow. In other aspects, the avatar can perform parts of the fitness routine during performance of the fitness routine by the user when demonstration is necessary (e.g., to correct improper technique by the user).

Interface 700 can also include various tools and menu options to facilitate customizing aspects of the workout routine and/or the appearance of the interface. For example, interface 700 can include a 'select environment section' 702 wherein a user can select a background environment (e.g., a beach, a city, mountains), for display in the workout space 710. Interface 700 can also include section a 'select music section' 704 which allows the user to select a type of music for playing during a workout. In an aspect, this section can be linked to another music database (e.g., the user's playlist or an external media streaming system) to allow for selection of a wide variety of music option. Section 706 includes a 'modify exercise section' wherein a user can modify various aspects of an exercise prior to or during performance. For example, the user can select the intensity of the workout (e.g., 60%, 80%, 100%, etc.). Modify exercise section 706 can also provide for selection of a fitness program and or workout to perform and/or modification of a selected workout program or routine. In order to begin a selected workout, the user can select the begin button. In an aspect, prior to beginning the workout, the user can select the practice button which takes the user through various simulations of the respective exercises in the routine as demonstrated by the avatar 712.

Interface 700 can also include various visual feedback areas (e.g., 714 and 716) that provide the user with information regarding the user's performance during the workout. For example, interface 700 can include a heart rate meter 714 that displays the user's current heart rate next to a target heart rate range marker. In an aspect, the heart rate meter 120 can change colors to provide an indication whether the user is above, below or at the target heart rate. In another example, area 716 can provide real-time feedback regarding an amount of calories the user has burned, the current exercise the user is performing, the number of repetitions completed and the current time point in the workout. Further, interface 700 can provide the user with various information sections, such as a goal section 708 noting the user's goals and the goals set by the user's trainer, and a limitation section 718 noting physical limitations of the user.

Figure 8:
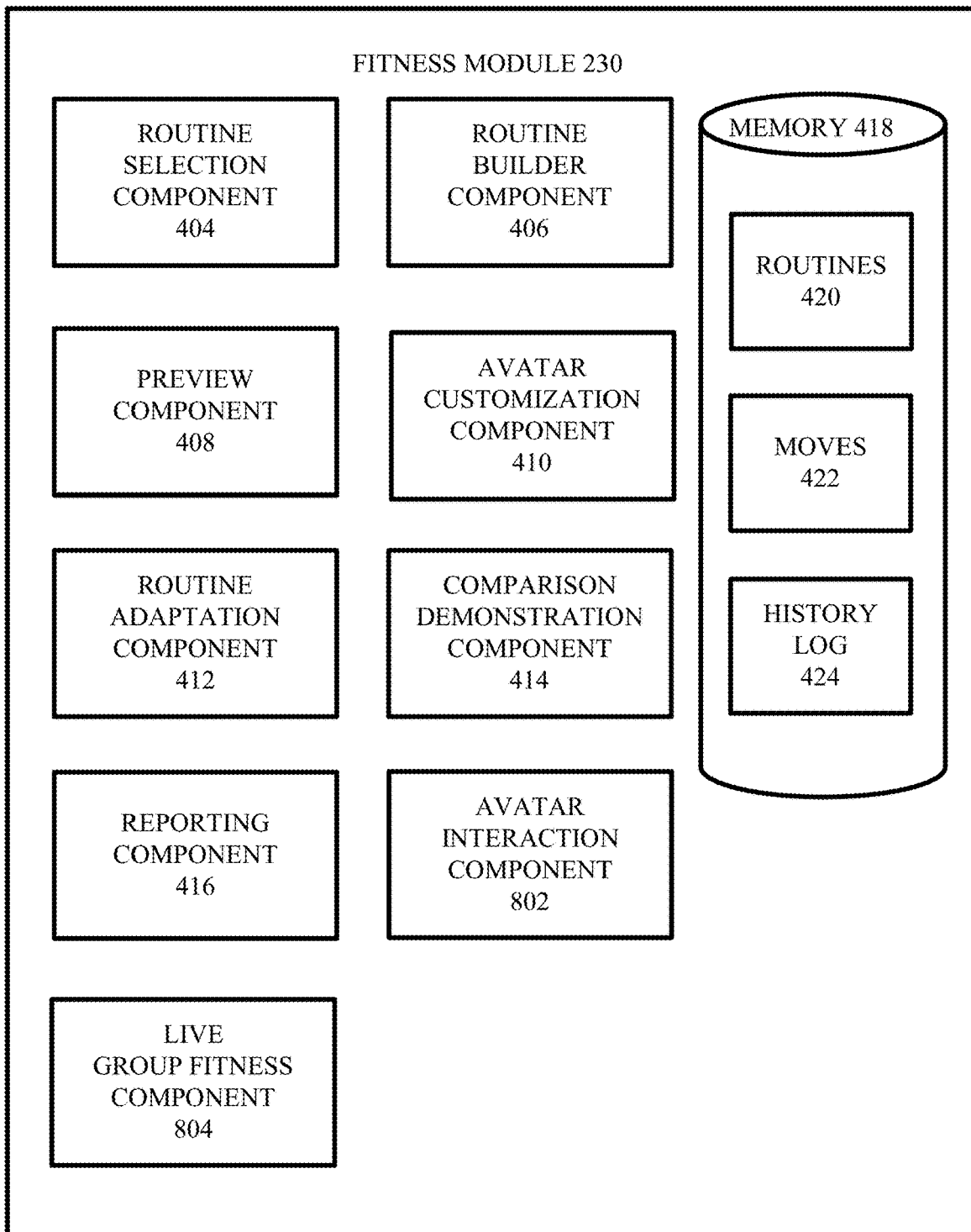
FIG. 8 illustrates another example fitness module for employment with an avatar guidance system in accordance with various aspects and embodiments described herein.

FIG. 8 provides another example embodiment of fitness module 230 in accordance with various aspects described herein. Repetitive description of like elements included in respective embodiments of systems and methods described herein is omitted for sake of brevity.

In accordance with the subject embodiment, fitness module 230 can also include avatar interaction component 802 and live group fitness component 804. Avatar interaction component 802 is configured to facilitate generating and presenting an avatar to a user that is responsive to not only the user's physical state and context but the physical states and contexts of one or more other users. In an aspect, avatar interaction component 802 provides a virtual gaming experience between two or more users. According to this aspect, the two or more users can request to participate in a gaming or interactive mode for a specific monitored program, routine, or activity. Each of the users can grant authorization of sharing information (e.g., in real-time or non-real time) regarding their respective performance of the program, routine, or activity between one another's user sessions. Depending on the nature of the program, routine or activity and the gaming or interactive mode selected, any of the user's avatars can react to both feedback about themselves and feedback about the other users.

In particular, avatar interaction component 802 can receive and analyze feedback for a primary user to which an avatar is presented and one or more other users that are also employing avatar guidance system 200 to perform a similar monitored program, routine or activity. Based on feedback indicating how the other one or more users are performing the monitored program, routine, or activity, avatar interaction component 802 can direct analysis component 212 and reaction component 214 to determine an appropriate reaction for the primary user's avatar. For example, a group of users at various different locations around the world can be involved in a running club. Using avatar guidance system 200 the respective users can set up group runs where they respectively set out to run a same distance together in a race format. For example, each of the users can select the same distance and terrain, start the run at the same time, and have their respective avatars serve as their individual coaches throughout the run. However, not only can the respective avatars respond and react to their respective user's feedback (e.g., as discussed herein), the respective avatars can also react to feedback received for any of the participating users. For example, assuming the respective users names are Abby, Bobby, Carmen, Donna, and Erin. Erin's avatar can tell Erin when to speed up, when to slow down, how to breath, etc. based on physical and physiological feedback received for Erin and Erin's personal profile and health information. In addition, Erin's avatar can tell Erin when to speed up and when to slow down based on how Abby, Bobby, Carmen, and Donna are performing (e.g., when the goal is to win the race). For example, Erin's avatar can note where the other users are in terms of position, speed, fatigue, cramping, etc. Based on this information for example, Erin's avatar can tell Erin to slow down and save some energy for the next mile because she is way ahead of the pack.

It should be appreciated that the above noted group race running example is merely one application of avatar interaction component 802. For example, avatar interaction component 802 can facilitate real-time interaction between two or more user's participating together in a variety of different fitness programs routines or activities whether the group participation is competitive in nature (e.g., a tennis match, a boxing match) or collaborative in nature (e.g., a soccer match where the group of users are on the same team).

Group fitness component 804 is configured to provide a group fitness atmosphere for two or more users of avatar guidance system 200 that have chosen to participate in a group fitness routine. The routine is considered a group fitness routine because the two or more users have selected to perform the same routine at the same time (or substantially the same time) and the two or more users have authorized sharing of one or more aspects of their personal avatar experience with one another during performance of the group fitness routine.

In an aspect, group fitness component 804 can facilitate generation of a shared user interface that is presented to the respective users participating in the group fitness routine. In one aspect, the interface can include avatars representative of the respective users in the group. As the respective users perform the fitness routine, their respective avatars can mimic what the real users are doing (e.g., their movement, facial expression, sounds, etc.). Thus the interface presented to any one of the respective users can resemble that of a real and live group fitness classroom (or other share environment) in which all the users are present together and performing the fitness routine together.

In another aspect, group fitness component 804 can facilitate generation of a shared trainer or coach to facilitate the group fitness routine. According to this aspect, each of the participating users can be presented with the same avatar coach or trainer. This avatar can respond to user feedback for each of the respective users in accordance with the aspects described herein. However, the responses provided by the avatar based on any one of the users feedback are collectively received by the group. For example, the avatar trainer can instruct one of the group fitness participants to pick up the pace and then demonstrate a movement to encourage the participant to pick of the pace. This avatar response directed to one of the participants can be seen and heard by each of the participants in a live manner. Similarly, using avatar interaction component 802, the shared trainer can respond to one of the group member's feedback on feedback from other users participating in the group fitness class. For example, the trainer can point out the perfect form exhibited by one of the group fitness members to the other group fitness members. In another example, the avatar trainer can tell a first group fitness member to kick his legs higher (based on the particular fitness move) like a second group fitness member is doing.

In another aspect, group fitness component 804 can provide for a shared trainer experience wherein each of the participants are monitored by the same avatar respectively presented thereto and see and hear the same avatar reactions in a live fashion. However, rather than reacting to individual users, group fitness component 804 can direct routine adaptation component 412 to dynamically modify the routine based on collective feedback from the users as a group. For example, in response to a determination that the majority of the users in the group are becoming extremely fatigued, the routine adaptation component 412 can adapt the group fitness routine accordingly. In response, the shared avatar trainer can instruct the group regarding the adaptation of the routine.

Figure 9:
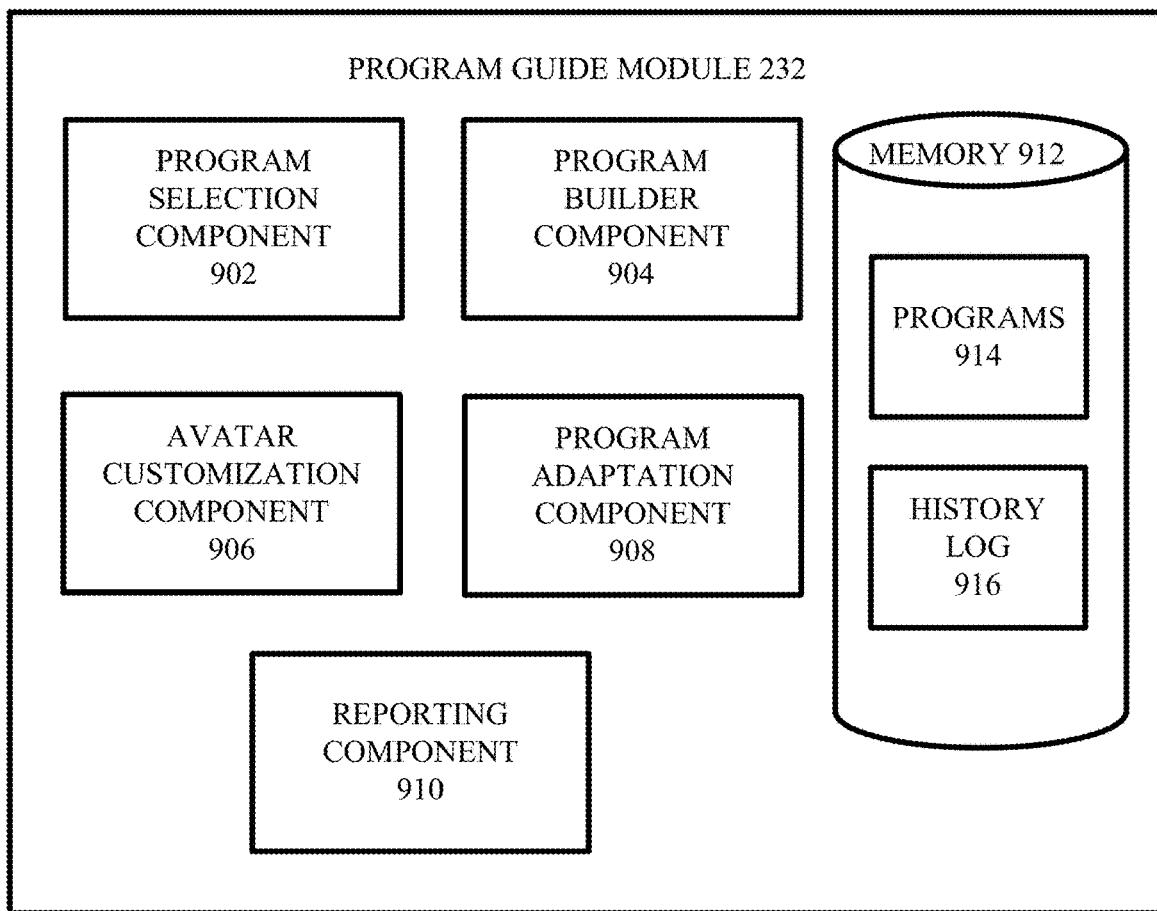
FIG. 9 illustrates an example program guide module for employment with an avatar guidance system in accordance with various aspects and embodiments described herein.

FIG. 9 provides an example embodiment of program guide module 232 in accordance with various aspects described herein. Repetitive description of like elements included in respective embodiments of systems and methods described herein is omitted for sake of brevity.

Program guide module 232 is specifically configured to facilitate guiding or assisting a user with adhering to a program using an avatar in association with various aspects of avatar guidance platform 202. In particular, program guide module 232 is configured to guide a user with performing a program having a plurality of predetermined actions or behaviors for the user to perform (or not perform) over a period of time to achieve a goal of the user. The period of time and goal can vary. However, program guide module 232 is particularly suited for guiding a user through a program that lasts several hours, days, weeks or even months wherein user input 234 is received over the course of the program. For example, a suitable program can include a health and/or fitness program designed to cause the user to get in better shape and health over a period of three weeks, three months, a year, etc. In another example, a suitable program can include a dietary program designed to help a user lose or gain weight in a healthy manner. Another suitable program can include a stress reduction program designed to help a user reduce and combat stress throughout her day. Other examples of suitable programs include an addiction recovery program, a mental health program, an anger management program, and any conceivable program that includes performance or non-performance of specific user behaviors to achieve a physical/physiological or mental goal wherein adherence can be monitored based on analysis of regularly received physical (e.g., motion/movement data and image data) and physiological (e.g., biometric/biochemical) information for the user and/or context information for the user.

During performance of a monitored program, information regarding one or more of the user's physiological state or condition, body movement/position, appearance, and context (e.g. location, time of day, people near the user), is dynamically received and analyzed in view of known requirements of the monitored program, and in some aspects user profile information, to determine or infer whether, how and to what degree the user deviates and/or is likely to deviate from the monitored program (in accordance with aspects described herein). Based on this analysis, reaction component 214 determines or infers a suitable reaction for manifestation by an avatar presented to the user and the avatar control component 208 and avatar generation component 226 cause the avatar presented to the user to perform the reaction. The reaction is configured to provide the user with guidance and/or motivation with adhering to the program and can include visual and audible reactions in the avatar (e.g., speaking, moving, facial expression, tone of voice, etc.). In some aspects, the reaction can include initiation of electronic communication (e.g., sending a notification, initiating an emergency call), and provision of external media (e.g., images, articles, a map, videos, songs, etc.) to the user to facilitate guiding the user with adherence to the program.

For example, a user can select a health and/or fitness program to perform and have monitored by avatar guidance platform 202. The health and fitness program can include a specific fitness and diet regimen that the user is to follow for a period of 21 days. Over the course of the program, reception component 204 can receive information indicating what food and drink the user has consumed (e.g., as input directly by the user, as provided/determined via various biometric sensors input, as determined via image analysis of food eaten by the user, etc.) and when the user has consumed it. Reception component 204 can also receive biochemical information for a user throughout the program (e.g., via input from the user, via one or more devices 104, via intelligent fitness device 118, via input from a remote laboratory service, etc.). As described supra, the biochemical information can related to one or more characteristics about the user's physiological state, such as levels of various biomarkers, known physiological conditions/diseases exhibited by the user based on the various levels, and/or health states of various human body systems. For example, throughout the health and fitness program, analysis component 212 can determine a user's blood sugar levels (e.g., glucose levels), cortisol levels, cholesterol levels, vitamin/mineral levels, hormone levels, electrolyte levels, antioxidant levels, blood oxygen levels, etc. Analysis component 212 can also determine a level inflammation experienced by a user, a hydration level of the user, a stress level of the user, an energy level of the user, a fatigue level of the user, a hunger level of the user, etc.

Reception component 204 can also receive and/or determine information regarding how many calories the user has consumed and burned user activity/motion levels, user sleep patterns, and physical performance of fitness activities. Reception component 204 can also receive information related to the user's context (e.g., where the user is located, what people, places, things and events are associated with the location, time of day, how the user is feeling, etc.). In addition, information regarding the user preferences, physical health, physical measurements (e.g., height, weight, BMI, body fat, etc.), performance history, schedule, etc., can be included in an accessible profile for the user.

According to this example, based on the dynamically received user input and the user profile information, analysis component 212 can determine when the user is deviating or is about to deviate from the health and fitness program. For example, analysis component 212 can determine or infer whether the user is eating the required/appropriate food and drink, whether the user is about to make bad food choices, whether the user burned/is burning the required amount of calories in a workout, whether the user performed/is performing a required workout, whether the user is performing the required workout in accordance with requirements for the workout, etc. In another example, analysis component 212 can determine whether a user is exhibiting acceptable levels of various biomarkers and/or whether the one or more characteristics about the user's physiological state indicate the user is deviating or is about to deviate from a requirement of the health/fitness routine. For example, analysis component can determine when a user's blood sugar is above an acceptable level for a particular time of the day or when a user has reached a level of fatigue beyond an acceptable level for a particular workout.

Based on such determinations and/or inferences regarding whether, how and to what degree the user is deviating or is about to deviate from the requirements of the health and fitness program, reaction component 214 can determine an action for performance by the user that is known or likely to either correct the deviation, minimize the impact of the deviation and/or prevent the deviation. Reaction component 214 can further select, determine or infer a reaction for manifestation by an avatar presented to the user that is configured to direct or guide the user to perform the action.

For example, a user can perform a general health and wellness program designed to improve the user's health. The health and wellness program can include various requirements associated with the user's diet, sleep patterns, activity patterns, physical exercise patterns, etc. The program can also include various requirements regarding physiological characteristics the user should exhibit throughout the program. For example, these physiological characteristics can pertain to the user's antioxidant levels, glucose levels, cholesterol levels, blood pressure levels, hormone levels, stress levels, energy levels, fatigue levels, inflammation levels, hydration levels, etc. During performance of the program, analysis component 212 can determine when the user's physiological state falls out of balance with that required by the program. For example, analysis component 212 can determine when a user's antioxidant levels have degreased below an acceptable level. Analysis component 212 and/or reaction component 214 can further determine, based on received information regarding a user's drug/alcohol ingestion that the user should reduce the amount of cigarettes and wine the user has been recently ingesting to facilitate increasing the user's antioxidant levels.

Reaction component 214 can further determine a reaction for manifestation by the user's avatar to direct the user to reduce the user's consumption of cigarettes and wine. For example, reaction component 214 can cause the avatar to speak a verbal reprimand to the user regarding the user's drug/alcohol consumption and instruct the user to reduce the user's drug/alcohol consumption. The tone of voice, facial expression and body language of the avatar can be determined to convey disapproval and concern. In addition, the reaction component 214 can have the avatar present the user (e.g., via a verbal instruction or via presentation of a video, image, web article, etc.) with information regarding the severe health consequences of smoking and drinking to the level exhibited by the user. In an aspect, the avatar can provide personalized encouragement to encourage the user to reduce his or her drug/alcohol consumption. For example, the avatar can remind the user of his or her goals for beginning the program or provide the user with an image of herself in a health state when her antioxidant levels where high compared to an image of the user in her current health state.

Accordingly, the avatar can function as the user's personalized guide configured to follow the user and track the user's behavior and physical/physiological state over the course of program and help the user adhere to the program. To provide for various aspects of avatar guidance system 200 when applied to facilitate a guiding a user through a program, program guide module 232 can include program selection component 902, program builder component 904, avatar customization component 906, program adaptation component 908 and reporting component 910. Program guide module 232 can also include various data objects stored in memory 912 (which can be inclusive of memory 218) that are specific to aspects of program guide module 232. These data objects can include information defining various programs 914 capable of being monitored by program guide module 232 and historical information for respective users logging their performance of various programs 232 using program guide module.

Similar to routine selection component 404 that provide for user selection of various preconfigured fitness routines for a user to select for performance, program selection component 902 provides for user selection of a program for performance by the user from a database of known programs 914 and associated requirements. For example, programs database 914 can include a plethora of different programs arranged by various categorical types (e.g., health and fitness, weight loss, weight gain, marathon training, low sugar diet plan, stress reduction plan, sleep regulation programs, addiction recovery program, etc.). In an aspect, each of these programs can include a description of the requirements of the program and the goals of the program. Each of these programs can be designed for performance over a fixed period of time or a boundless amount of time. For example, a user can select a fitness program designed as a 90 day challenge or select a stress reduction program or alcohol addiction recovery for performance on a daily basis until the user chooses to stop the program.

Similar to routine builder component 406 which facilitates building of a custom fitness routine by a user (or supervisor of the user), program builder component 904 facilitates designing a custom program. In an aspect, a user can select a preconfigured program and change certain variables/requirements of the program to fit the user's needs. In other aspects program builder component 904 can allow a user (or a supervisor of the user) to build a custom program from scratch. For example, a user can set a schedule the user would like to adhere to, defining what the user should do and when and how the user should respond to certain scenarios.

In another aspect, program builder component 904 can automatically adapt a preconfigured program to fit the user's needs based on profile information for the user (e.g., user preferences, user health history, user physical abilities, user habits etc.) or program builder component 904 can build a custom program (e.g., from scratch) for a user based on the user's goals and other profile information for the user (e.g., preferences, demographics, location, language, user, budgetary constraints, habits, health history, physical appearance and measurements, dietary restrictions, medications, schedule, and/or historical performance information (regarding past programs, routines, or activities tracked via avatar guidance system 200)). For example, a user can state that her goal is to lose 10 pounds in one month. Based on various information about the user's preferences (e.g., what foods the user likes/dislikes, what types of physical exercise the user likes/dislikes, how much and when the user likes to work out, etc.), demographics, location, language, user, budgetary constraints, habits, health history, physical appearance and measurements, dietary restrictions, medications, schedule, and/or historical performance information, program builder component 904 can generate a custom health and fitness program that is designed to cause the user to achieve her goal if followed properly. Program builder component 904 can also employ routine builder component 906 to facilitate generating custom fitness routines to include in a health and fitness program.

In an aspect, the user can analyze the custom program and provide input regarding modifications to the program. For example, a health and fitness program output by program builder component 904 could include some requirements that the user would like to change. According to this example, the program could require the user to work out 5 days a week when the user would prefer to work out 4 days a week. Based on input requesting the program to be modified to working out 4 days a week, program builder component 904 can automatically adjust other requirements of the program to maintain the user's goal. For example, program builder component 904 could adjust the intensity of the workouts and/or modify her diet to account for the lost workout day. In other aspect, program builder component 904 can request specific user input to facilitate creating a custom program for the user. For example, depending on the type of program and the user's goal, program builder component 904 can have the user fill out a form (e.g., or otherwise provide input) with answers to a specific set predetermined questions associated with the creation of the type of program. The user's answers can be used to create/customize the program for the user.

In an aspect, in association with generation of a custom health and fitness program for a user, the user can provide program builder 904 with an image of the user and/or avatar guidance platform 202 can receive captured image data of the user (e.g., via visual capture device 110). For example, two or three-dimensional image data can be captured and received for a user. The captured image data can be provided to avatar guidance platform 202 in the form of a two or three dimensional visual replica/representation of the user or avatar guidance platform 202 can employ the captured image data to generate a be a visual replica/representation of the user (e.g., a two or three-dimensional avatar representation of the user). In addition to image data, physical measurements (e.g., regarding user height, weight, dimensions of body parts, BMI, etc.) can be received for the user and/or detected via the image data. This measurement data can facilitate generation of a two or three dimensional visual representation of the user.

According to this aspect, the user can provide input regarding characteristics of body features that the user would like to change and how the user would like them to change using the image of the user and/or the visual representation of the user. For example, the user could circle or target certain body parts and indicate how the user would like them to change. According to this example, the user could point to her stomach and indicate she would like to trim off inches from her waist or develop a six pack. In another example, the user could point to her arms and indicate she would like to increase the diameter of her biceps. In an aspect, this input can be received from the user by directly allowing the user to draw on/mark up the image/visual representation of the user. For example, the user could place lines or marks on parts of the user's body indicating how the user would like the body parts to appear.

Based on received input indicating characteristics of body features that the user would like to change and how the user would like them to change based on user input regarding an image or visual replica of the user, user profile information, and any other user input regarding requirements for the program, (e.g., duration of the program, preferences for the program, exercises and foods the you would like included/excluded from the program, etc.), program builder component 904 can design a custom diet and/or exercise program for the user. The custom diet and exercise program is specifically tailored to achieve the user's goals (e.g., the changes to the user's physical appearance as pointed on by the user with respect to an image or visual representation of the user).

In another aspect, in association with generation of a custom health and fitness program for a user, the user can provide program builder 904 with an image or visual representation of physical features the user desires. For example, the user could provide program builder component 904 with a picture of an athlete and request to have a program designed for the user that will cause the user to look like the athlete. In another example, the user could provide program builder component 904 with an image of a supermodel and indicate that she would like to transform her body to look like the supermodel. In another example, the user could provide program builder component 904 with a picture of a specific body part and request a program that would help the user transform his or her corresponding body part to appear like that in the picture. For example, the user can provide program builder component 904 with an image of a person's shoulders and indicate he would like his shoulder to look like the picture.

According to this aspect, based on received input indicating characteristics of body features that the user would like to have based on image data representing those characteristics, user profile information, and any other user input regarding requirements for the program, (e.g., duration of the program, preferences for the program, exercises and foods the you would like included/excluded from the program, etc.), program builder component 904 can design a custom diet and/or exercise program for the user. The custom diet and exercise program is specifically tailored to achieve the user's goals (e.g., the changes to the user's body features to have the characteristics of those provided in the image data.

Similar to avatar customization component 410, Avatar customization component 906 can provide for customizing the appearance and personality of an avatar selected by the user to guide the user through a program. For example, the user can choose the gender, age, ethnicity, language, clothing, voice, and personality of their avatar. The user can also choose an avatar from a database of preconfigured avatar's having various appearances and personalities. In an aspect, the avatar can embody a persona selected by the user, such as the user's conscience (e.g., the voice of reasoning or angel on the user's shoulder), the user's friend, the user's mother, the user's coach/trainer, the user's doctor, the user's therapist, etc. In another aspect, the user can select multiple avatars to help guide the user with different aspects of a program. For example, with respect to a diet and exercise program, the user can select a first avatar to facilitate adherence to aspects of the program related to the user's diet and a second avatar to facilitate aspects of the program related to the user's exercise.

Similar to routine adaptation component 412, program adaptation component 908 can facilitate dynamically adapting aspects and requirements of a program during the course of the program. Program adaptation component 908 can adapt aspects and requirements of a program based on a variety of aspects including but not limited to: user physical and physiological activity data and context data, reference data for the user physical and physiological activity data and context data for the program, and user profile information (e.g., user preferences, user goals, past performance history, etc.). For example, program adaptation component 908 can adjust and/or dynamically determine new or modified requirements of a program based on a determination that the requirements are too difficult or too easy because the user is consistently not meeting or exceeding the requirements of the program, respectively.

In another example, program adaptation component 908 can analyze a user' history of performance with respect to adherence to a program and dynamically adapt the requirements of the program to account for the user's past performance. For example, where a user ran an extra 5.0 miles on the workout the day before, program adaptation component 908 and/or routine adaptation component 412 can change the requirements of today's workout to account for the extra 5.0 miles from the day before. For example, where today's workout was supposed to be a longer run, program adaptation component can determine that the user's goals (e.g., to get in shape for an upcoming race) would be better suited if the workout today was switch to yoga (e.g., to prevent injury due to over exercise). In another example, program adaptation component 908 can adapt current requirements of a user's program based on how the user is feeling (e.g., sore, sick, energized, sad, tired, etc.), an amount of sleep received, an amount of activity of the user that day/week, an amount of stress the user is experiencing, what the user's current physiological state is, what the user's current context is, what the user ate that day (e.g., ate an extra number of calories, earn an extra number of jumping jacks), unexpected changes to the user's schedule, unexpected injuries, events in the user's life, how the user is progressing in the program, resources available to the user (e.g., group meetings, therapy, exercise equipment, food options, etc.

In another example, program adaptation component 908 is configured to regularly (e.g., once an hour, twice a day, once a day, once a week, etc.) evaluate a user's progress through a program in view of the user's goals and determine whether and how to adapt the requirements of the program based on the user's progress. For example, when a user's is hoping to lose X amount of weight and the user is not on target to achieve this goal if the user adheres to the current requirements of the program for the remainder of the program, program adaptation component 908 can adjust the dietary and/or exercise requirements of the program to ensure the user will achieve her goal.

Similar to reporting component 416, reporting component 910 can send information regarding a user's performance of a program in real-time or substantially real-time to another entity (e.g., another user, another system) for interpretation thereof. For example, with respect to drug rehabilitation program, reporting component 910 can send information regarding a user's adherence or deviation from the program to the user's therapist in real-time. In another example, with respect to a diet and exercise program, reporting component can send information regarding the user's performance of the program to the user's real life (e.g., human) trainer in real-time.

Figure 10:
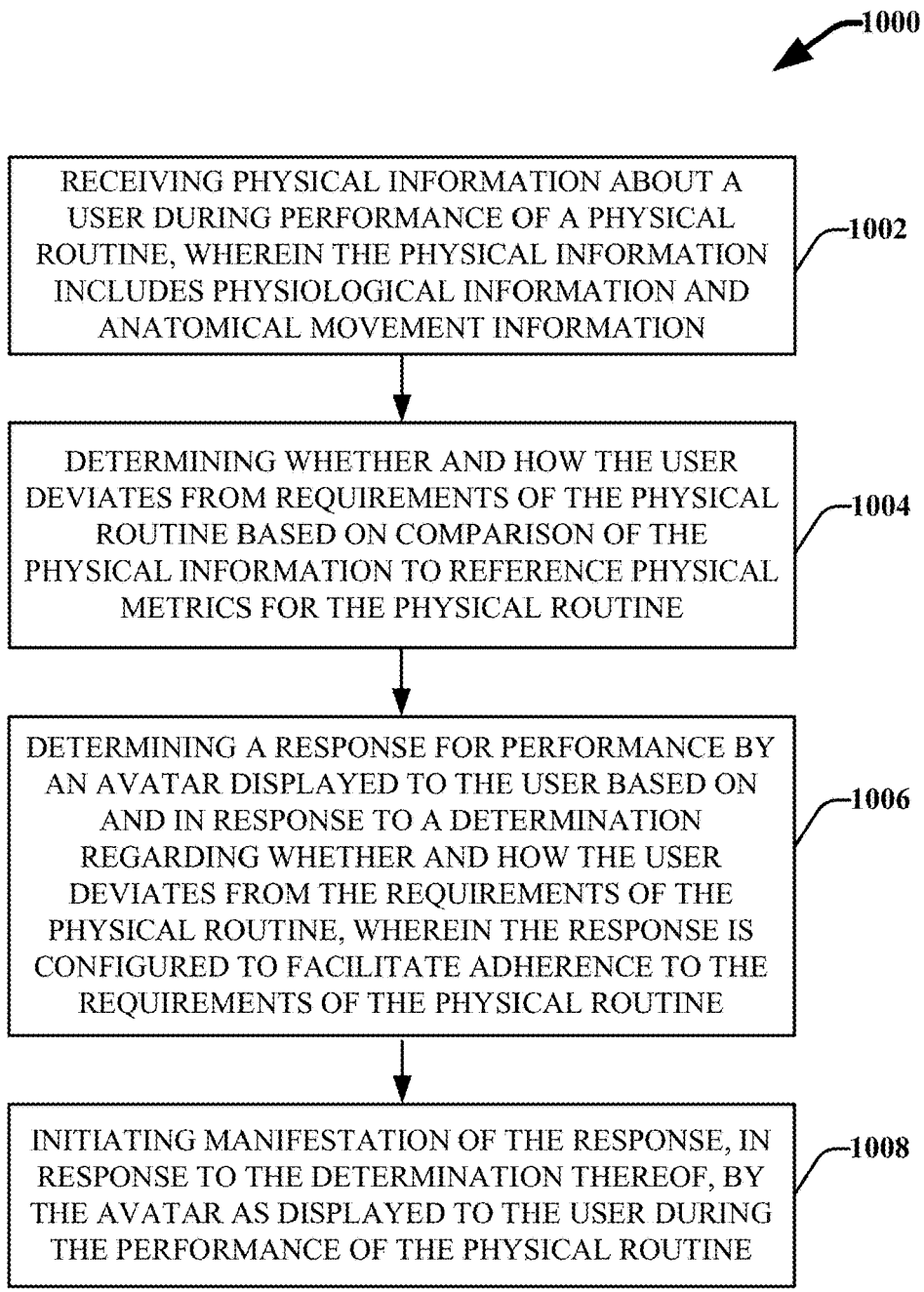
FIG. 10 presents a flow diagram of an example method for generating a personalized avatar that is responsive to a user's physical state and context, in accordance with various aspects and embodiments described herein.
Figure 11:
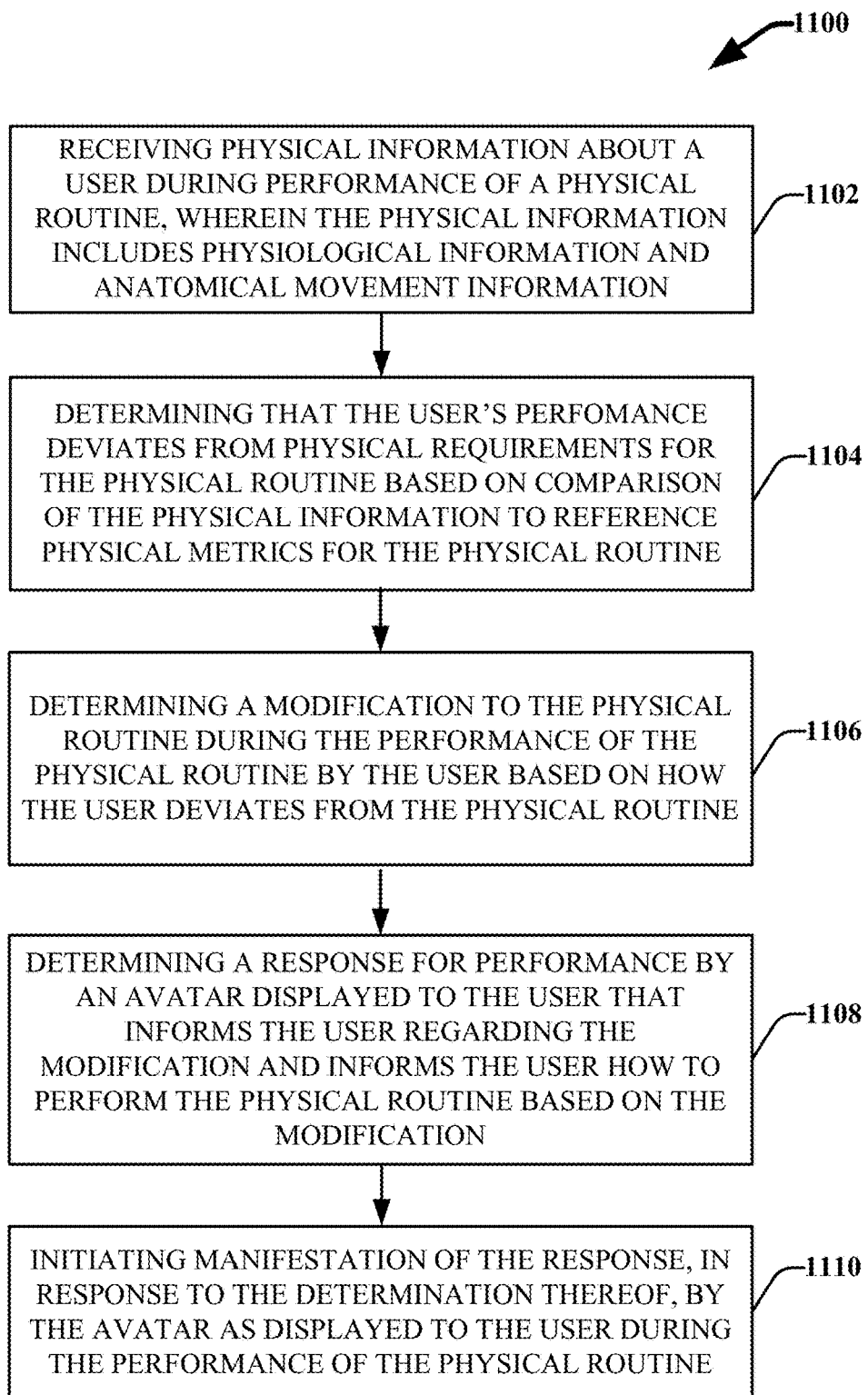
FIG. 11 presents a flow diagram of another example method for generating a personalized avatar that is responsive to a user's physical state and context, in accordance with various aspects and embodiments described herein.
Figure 12:
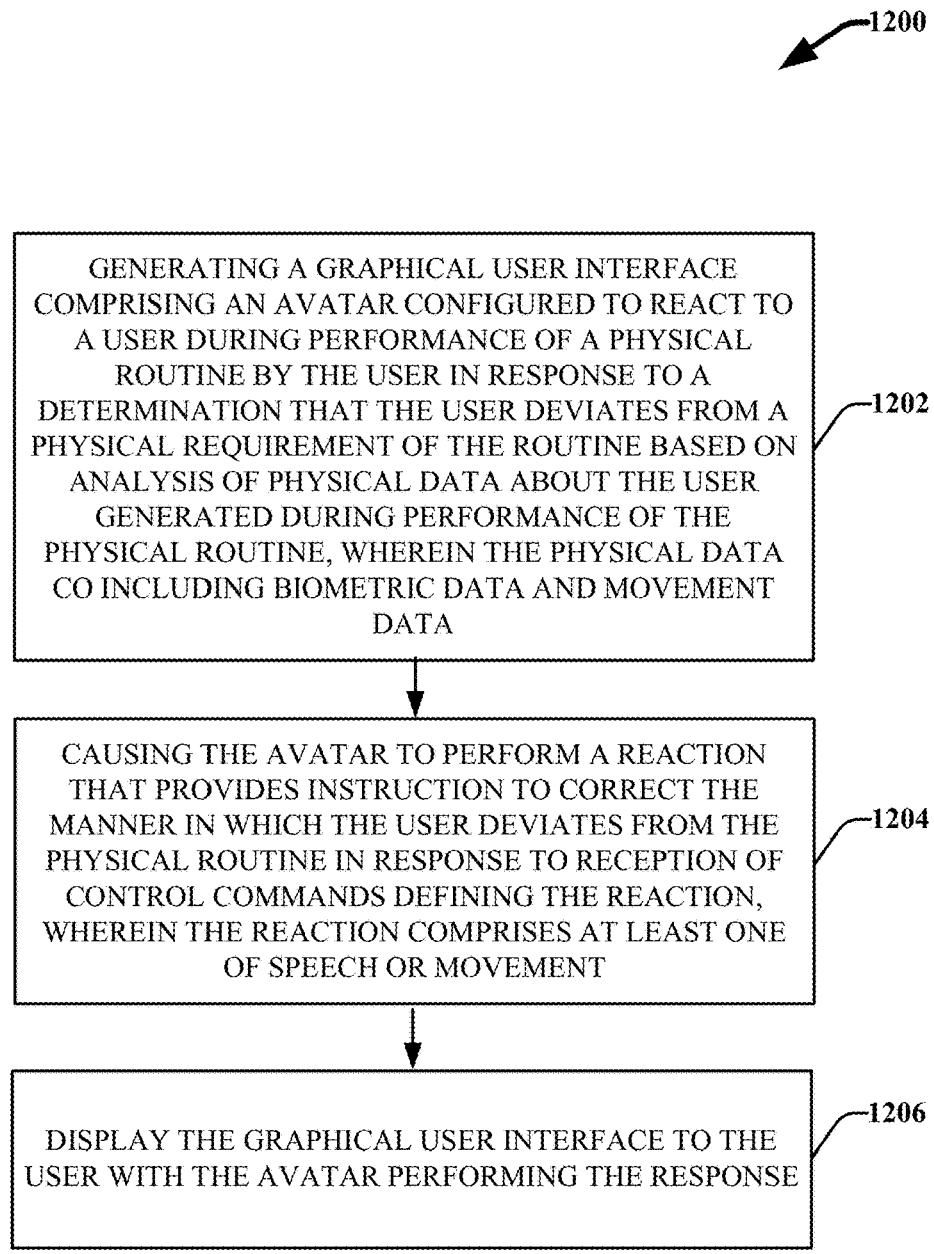
FIG. 12 presents a flow diagram of another example method for generating a personalized avatar that is responsive to a user's physical state and context, in accordance with various aspects and embodiments described herein.

In view of the example systems and interfaces described herein, example methods that can be implemented in accordance with the disclosed subject matter can be further appreciated with reference to flowcharts in FIGS. 10-12. For purposes of simplicity of explanation, example methods disclosed herein are presented and described as a series of acts; however, it is to be understood and appreciated that the disclosed subject matter is not limited by the order of acts, as some acts may occur in different orders and/or concurrently with other acts from that shown and described herein. For example, a method disclosed herein could alternatively be represented as a series of interrelated states or events, such as in a state diagram. Moreover, interaction diagram(s) may represent methods in accordance with the disclosed subject matter when disparate entities enact disparate portions of the methods. Furthermore, not all illustrated acts may be required to implement a method in accordance with the subject specification. It should be further appreciated that the methods disclosed throughout the subject specification are capable of being stored on an article of manufacture to facilitate transporting and transferring such methods to computers for execution by a processor or for storage in a memory.

FIG. 10 illustrates a flow chart of an example method 1000 for generating a personalized avatar that is responsive to a user's physical state and context, in accordance with various aspects and embodiments described herein. At 1002, information about a user is received during performance of a physical routine by the user (e.g., via reception component 204). The information includes physiological information and anatomical movement information. For example, as a user performs a workout routine or a particular sports activity, information regarding the user's heart rate, blood pressure, perspiration, cortisol level, glucose level, etc. can be received. In addition, information regarding what movements the user is performing, how the user's body is positioned during the movement and intensity of the movement can be received. At 1004, it is then determined whether and how the user deviates from requirements of the physical routine based on comparison of the information to reference physical and physiological activity metrics for the physical routine (e.g., by analysis component 212). For example, analysis component can determine that the user's physiological state indicates that the user does not comply with what the user's physiological state should be for a particular exercise of the physical routine. In another example, analysis component can determine that the user's body position during a particular exercise yoga exercise is on target or not on target with how it should be.

At 1006, a response is determined for performance by avatar displayed to the user, based on and in response to, a determination regarding whether and how the user deviates from the requirements of the physical routine (e.g., via reaction component 214). The response is configured to facilitate adherence to the requirements of the physical routine. For example reaction component 214 can determine a response that includes provision of spoken instruction and physical demonstration by the avatar regarding an action for the user to perform that corrects a deviation. According to this example, where the user's pace and intensity of an exercise move is below the required level, the avatar response can include act of performance of the exercise move at the required intensity level with exclamatory words of encouragement spoken in an enthusiastic tone telling the user to "pick up the pace, let's go let's go!" Once the user corrects the deviation, the avatar's behavior can change accordingly (e.g., the avatar can go back to evaluating the exercise as opposed to demonstrating, and the avatar can congratulate the user for adhering to the requirements of the fitness routine). At 1008, manifestation of the response is initiated, in response to the determination thereof, by the avatar as displayed to the user during the performance of the physical routine (e.g., by the avatar control component 208, and the avatar generation component 226). In other words, the avatar presented to the user is caused to perform the response.

FIG. 11 illustrates a flow chart of another example method 1100 for generating a personalized avatar that is responsive to a user's physical state and context, in accordance with various aspects and embodiments described herein. At 1102, information about a user is received during performance of a physical routine by the user (e.g., via reception component 204). The information includes physiological information and anatomical movement information. For example, as a user performs a workout routine or a particular sports activity, information regarding the user's heart rate, blood pressure, perspiration, cortisol level, glucose level, etc. can be received. In addition, information regarding what movements the user is performing, how the user's body is positioned during the movement and intensity of the movement can be received. At 1104, it is then determined that the user's performance deviates from physical and physiological activity requirements for the physical routine based on comparison of the information to reference physical and physiological activity metrics for the physical routine (e.g., by analysis component 212). For example, analysis component can determine that the user's physiological state indicates that the user is consistently (with respect to a deviation frequency threshold) falling below physical intensity requirements for the routine (e.g., based on heart rate, perspiration, fatigue, range of motion, etc.).

At 1106, a modification to the physical routine is determined during the performance of the physical routine by the user based on how the user deviates from the physical routine (e.g., by routine adaptation component 412). For example, the routine adaptation component can determine that the user should change the required exercises to an easier option. At 1108, a response for performance by an avatar displayed to the user is determined that informs the user regarding the modifications and informs the user how to perform the physical routine based on the modification (e.g., via reaction component 214). The response is configured to facilitate adherence to new requirements of the modified physical routine. At 1118, manifestation of the response by the avatar is initiated in response to the determination thereof, by the avatar as displayed to the user during the performance of the physical routine (e.g., by the avatar control component 208, and the avatar generation component 226).

FIG. 12 illustrates a flow chart of another example method 1200 for generating a personalized avatar that is responsive to a user's physical state and context, in accordance with various aspects and embodiments described herein. At 1202, a graphical user interface is generated that includes an avatar configured to react to a user during performance of a physical routine by the user in response to a determination that the user deviates from a physical requirement of the routine based on analysis of biometric and movement data about the user generated during performance of the physical routine (e.g., via interface component 206). At 1202, the avatar is caused/directed to perform a reaction that provides instruction to correct the manner in which the user deviates from the physical routine in response to reception of control commands defining the reaction, wherein the reaction comprises at least one of speech or movement (e.g., via avatar generation component 226). At 1206, the graphical user interface is displayed to the user with the avatar performing the response (e.g., via rendering component 226).

IV—Example Avatar Visualization System

In one or more aspects, a system is provided that includes a reception component configured to receive information corresponding to a user's physical appearance and physical health, an analysis component configured to determine or infer one or more changes to the user's physical appearance based on predicted performance of a health and fitness program by the user and the user's physical health, and a visualization component that is configured to generate a visual representation of the user based on the information and the one or more changes to the user's physical appearance.

In another aspect, a method is disclosed that includes receiving information corresponding to a user's physical appearance and physical health, predicting one or more changes to the user's physical appearance based on predicted performance of a health and fitness program by the user and the user's physical health, and generating a visual representation of the user based on the information and the one or more changes to the user's physical appearance.

In yet another aspect, a method is provided that includes using a processor to execute the computer executable instructions stored in a memory to perform the various acts. These acts include receiving information corresponding to a user's physical appearance and physical health, predicting one or more changes to the user's physical appearance based on predicted performance of a health and fitness program by the user and the user's physical health, generating a visual representation of the user based on the information and the one or more changes to the user's physical appearance, and displaying the visual representation via a graphical user interface.

In various additional implementations, a method is provided that includes receiving, by a system comprising a processor, biochemical information about a physiological state or condition of a user, including information identifying a presence or a status of one or more biomarkers, determining, by the system, one or more characteristics of the physiological state or condition of the user based on the information identifying the presence or the status of the one or more biomarkers, adapting an appearance of an avatar presented to the user based on the one or more characteristics to reflect the one or more characteristics.

Figure 13:
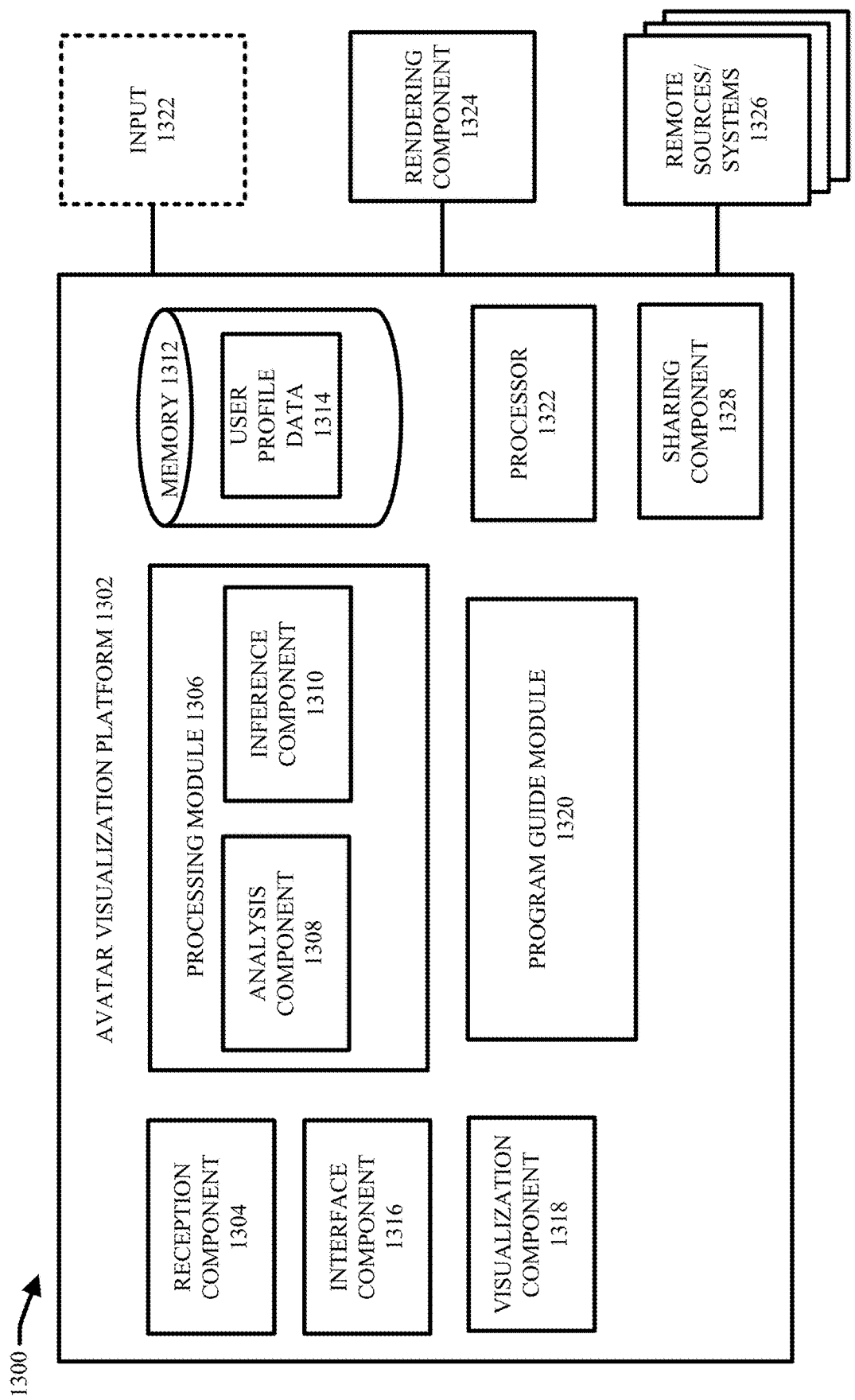
FIG. 13 presents an example avatar visualization system that facilitates visualizing how the user will appear in response to adhering to a health and fitness program in accordance with various aspects and embodiments described herein.

FIG. 13 presents an example avatar visualization system 1300 that facilitates visualizing how the user will appear in response to adhering to a health and fitness program in accordance with various aspects and embodiments described herein. System 1300 can include same or similar features and functionalities as system 100. In an aspect, system 1300 employs the architecture of system 100, including one or more of the various components/devices of system 100, wherein avatar visualization platform 1302 corresponds to avatar platform 114. Avatar visualization platform 1302 can thus include same or similar features and functionalities as avatar platform 114. Repetitive description of like elements employed in respective embodiments of systems and interfaces described herein are omitted for sake of brevity.

Avatar visualization system 1300 can include avatar visualization platform 1302, input 1322, rendering component 1324 and one or more remote sources/systems 1326. Input 1322, rendering component 1324 and the one or more remote sources/systems 1326 can respectively correspond to input 234, rendering component 236 and one or more remote sources/systems 238 discussed with respect to FIG. 2. For example, the input 1322 can include physical (e.g., movement/motion and image data), physiological (e.g., biometric/biochemical), contextual information about a user. The input 1322 can also include information included in a user profile of the user (e.g., health history, demographics, preferences, etc.).

In various embodiments, avatar visualization platform 1302 is configured to generate a visual representation or replica (e.g., an avatar) of a user based on received appearance data for the user, received physiological information for the user, and known health information for the user (including physical characteristics of the user and physiological characteristics of the user). In particular, avatar visualization platform 1302 can generate an avatar that is a visual replica of the user as the user currently appears. Accordingly, as the user's appearance changes over the course of performance of a health and fitness program (or other suitable program), the appearance of the avatar can also change to provide a mirrored visualization of the changes in the user. For example, throughout the course of the program (e.g., on a continuous basis, one an hour, once a day, etc.), an appearance of the user can be evaluated, captured and imparted to the avatar. Thus in essence, the user's avatar can resemble a mirror image of himself over the course of a program.

In some embodiments, avatar visualization platform 1302 is configured to generate an avatar that has an appearance and/or behavior that reflects a current physiological state or condition of the user. According to these embodiments, reception component 1304 can receive biometric/biochemical information for a user. For example, as described supra, the biometric/biochemical information can include but is not limited to information regarding a user's: glucose level, cortisol level, potassium level, blood oxygen level, blood alcohol level, inflammation level, nitric oxide level, folic acid level, calcium level, magnesium level, creatine kinase level, vitamin B12 level, vitamin D, ferritin level, total cholesterol level, hemoglobin level, HDL level, LDL level, triglycerides levels, fatty acid levels, insulin level, hormone levels (e.g., thyroid hormones (thyroid-stimulating hormone (TSH), metabolic hormones, reproductive hormones, etc.), liver enzyme levels, electrolyte levels (e.g., sodium, potassium, chloride, etc.), antioxidant levels, platelet levels, white blood cell concentration, red blood cell concentration, and iron levels. In another example, the biochemical information can identify presence and concentration of drug residues in the body, pathogens in the body, bacteria in the body, and antibodies. Additional biometric information can include information regarding a user's heart rate, blood pressure, V02 max, temperature, respiration, and perspiration.

As discussed infra, this biochemical/biometric information can be received from a variety of sources, including biometric sensing devices worn by or implanted into a user (e.g., devices 104), external biometric detection devices (e.g., intelligent fitness device 118) employed by the user (e.g., handheld spectroscopic devices, blood pressure cuffs, etc.), laboratory reports received electronically from an external system, and direct user input (e.g., following performance of a home biometric test). According, the biometric/biochemical information can be received prior, during (e.g., in real-time), and/or following performance of a monitored routine, activity, or program, in accordance with the various aspects and embodiments described herein.

Avatar visualization platform 1302 can include a processing module 1306 that can perform same or similar functions as processing module 210. For example, processing module 1306 can include an analysis component 1308 that is configured to perform same or similar functions as analysis component 212. In particular, based on the received biochemical/biometric information for a user (e.g., including information identifying a presence or a status of one or more biomarkers), analysis component 1308 can determine one or more characteristics of a physiological state or condition of the user. For example, based on detected presence of a particular biomarker, analysis component 1308 can determine a known medical condition or disease exhibited by the user. In another example, analysis component 1308 can determine whether and to what degree levels of the respective biomarkers are abnormal (e.g., with respect to predefined values or ranges for normal vs. abnormal levels). Analysis component 1308 can further determine or infer known conditions or diseases of the body that are attributed to the abnormal levels of the respective biomarkers.

In another example, based on the information identifying the presence and/or status/level of various biomarkers, analysis component 1308 can determine one or more characteristics associated with a state of a human body system of the user, such as whether the body system is in a healthy state or an unhealthy state (and varying degrees between severely unhealthy or extremely healthy) and why, whether the system is functioning properly or improperly and why, whether the system is functioning at a desired performance level (e.g., in association with a particular physical activity), etc. These human body systems include at least one of: the integumentary system, the skeletal system, the nervous system, the cardiovascular system, the endocrine system, the muscular system, the lymphatic system, the respiratory system, the urinary system, the excretory system, the reproductive system, the digestive system, and the immune system.

Avatar visualization platform 1302 can further include a visualization component 1318 that is configured to adapt an appearance of the avatar based on the one or more characteristics of the physiological state/condition of the user to reflect the one or more characteristics of the physiological state/condition of the user. For example, visualization component 1318 can adapt a color of the avatar, a size of the avatar, a shape of the avatar, or a texture of the avatar, based on the one or more characteristics. In another example, avatar visualization component 1318 can change an appearance of features/body parts of the avatar based on the one or more conditions. For example, visualization component 1318 can add or remove wrinkles or lines to the avatar, change the avatar's hair length, thickness, or color, change an appearance of the avatars face (e.g., puffy vs. refreshed, add bags under the eyes, etc.), change a color of the avatars skin, add or remove sun spots or freckles to the avatars skin, add or remove acne from the avatar's skin, add or remove bruises and varicose veins from the avatar's skin, etc.

In one implementation, when the one or more characteristics of the physiological state/condition of the user relate to a characteristic of a human body system of the user (e.g., the integumentary system, the skeletal system, the nervous system, the cardiovascular system, the endocrine system, the muscular system, the lymphatic system, the respiratory system, the urinary system, the excretory system, the reproductive system, the digestive system, or the immune system) the visualization component 1318 can highlight one or more parts of a body of the avatar based on the characteristic of the human body system of the user to reflect the characteristic of the human body system. For instance, the visualization component 1318 can be configured to cause the one or more parts of the body of the avatar area to change color, flash, or change in size or shape.

In an aspect, avatar visualization component 1318 can highlight the one or more body parts, including but not limited to: organs, muscles, tissues, bones, ligaments, veins, etc., associated with a particular human body system to reflect a current health state of the human body system. The health state of the respective body systems can be determined based on in part on the levels of various biomarkers associated with proper and optimal health functioning of the respective body systems. In an aspect, the health state can identify varying levels of health (e.g., extremely unhealthy vs. extremely healthy and varying degrees therebetween) of the body system or a type of disease or condition effecting the body system.

For example, visualization component 1318 can be configured to highlight one or more components of the avatar's cardiovascular system with a specific color or flashing speed to indicate the cardiovascular system is in an unhealthy state, and/or the degree to which the system is in an unhealthy state (e.g., red for very unhealthy, pink medium unhealthy). In another example, visualization component 1318 can highlight one or more components of the avatar's cardiovascular system with a specific color or flashing speed to indicate a level the user is at risk for a cardiovascular disease (CVD). In another example, the visualization component 1318 can highlight one or more parts of the avatar's cardiovascular system to indicate a level of a detected biomarker that reflects on the current health state the cardiovascular system. For example, visualization component 1318 can highlight various components of the avatar's cardiovascular system to reflect a current blood pressure, cholesterol level, blood alcohol level, or glucose level of the user, all of which have an effect a human's cardiovascular health.

In another example, visualization component 1318 can be configured to highlight components of the avatar's integumentary system with a specific color or flashing speed to indicate a physiological condition or disease affecting the user's integumentary system (e.g., a rash, an infection, an insect bite, sunburn, skin cancer, etc. The integumentary system is the organ system that protects the body from various kinds of damage, such as loss of water or abrasion from outside. The system comprises the skin and its appendages (including hair, scales, feathers, hooves, and nails). The integumentary system has a variety of functions; it may serve to waterproof, cushion, and protect the deeper tissues, excrete wastes, and regulate temperature, and is the attachment site for sensory receptors to detect pain, sensation, pressure, and temperature. In most terrestrial vertebrates with significant exposure to sunlight, the integumentary system also provides for vitamin D synthesis.

In another example, visualization component 1318 can be configured to highlight components of the avatar's skeletal system with a specific color or flashing speed to indicate a physiological condition or disease affecting the user's skeletal system, such as osteoporosis, osteomalacia, arthritis, rickets, tendinitis, bursitis, leukemia, etc. In another example, visualization component 1318 can be configured to highlight components of the avatar's endocrine system with a specific color or flashing speed to indicate levels of various hormones in the user's body. In another example, visualization component 1318 can be configured to highlight components of the avatar's muscular system with a specific color or flashing speed to indicate a level of lactic acid or muscle fatigue experienced by a user. In another example, visualization component 1318 can be configured to highlight components of the avatar's the immune system with a specific color or flashing speed to indicate a current health status of the user's immune system, to indicate the user has a virus or infection, to indicate the is immunosuppresed, etc.

Figure 14:
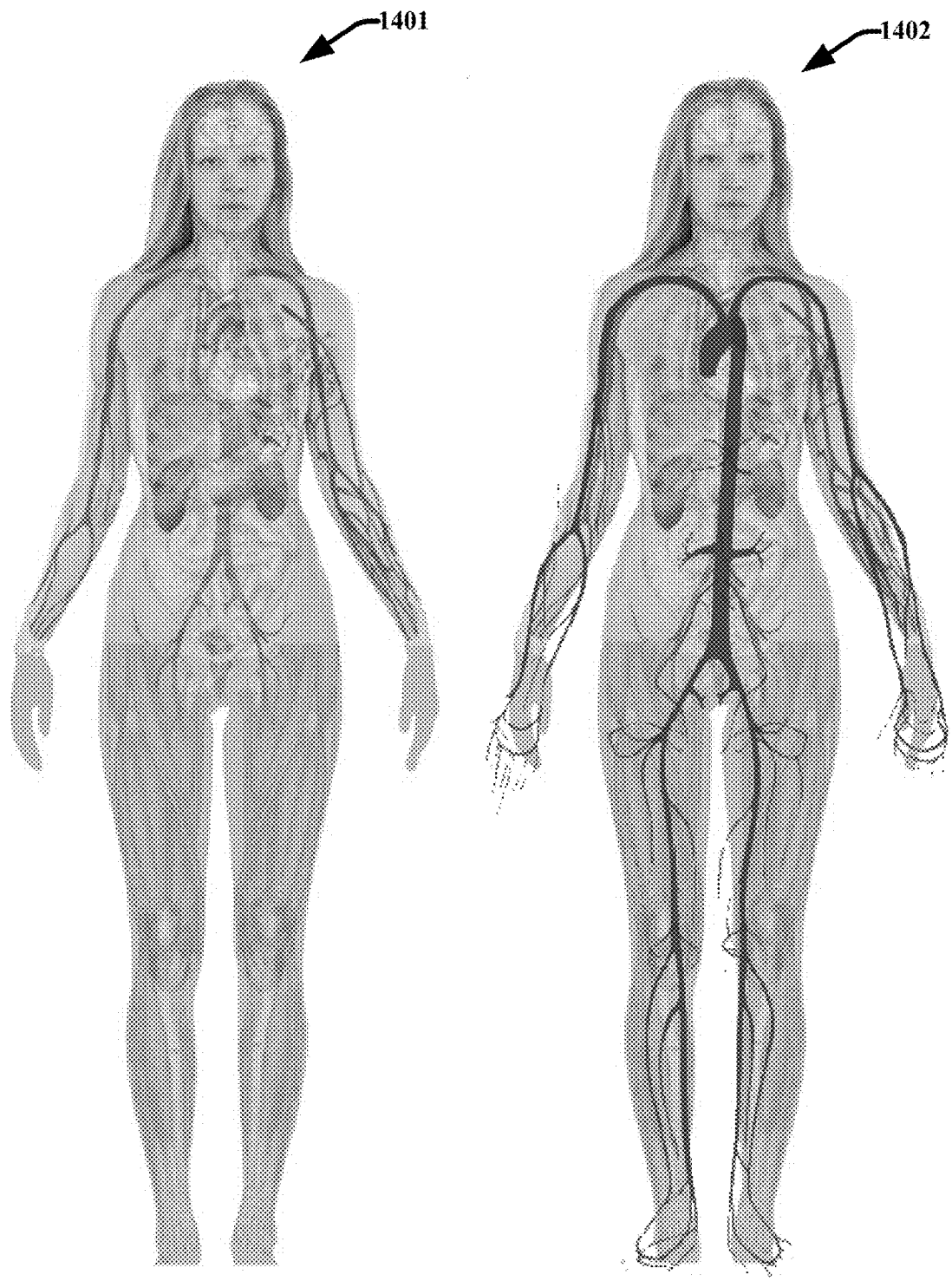
FIG. 14 presents example representations of an avatar that can be presented to a user in accordance with various aspects and embodiments described herein.

For example, FIG. 14 presents example representations 1402 and 1402 of an avatar that can be presented to a user in accordance with various aspects and embodiments described herein. Representation 1401 includes an avatar with various internal components of a human body represented in different colors. In an aspect, the colors of the various internal components of the avatar depicted in representation 1401 indicate that the user in a healthy state. On the contrary, representation 1402 includes the avatar with various components of the circulatory system highlighted in a dark green. In an aspect, these components of the avatar's circulatory system are depicted in dark green to signify the user is exhibiting various indicators of cardiovascular disease.

In various embodiments, rather than targeting specific body parts/components based on identified conditions or biochemical/physiological states of those body parts, visualization component 1318 can be configured to cause a user's avatar to appear in a specific color based on various physiological states/conditions affecting the user. Each color can indicate a particular physiological state/condition affecting the user. For example, based on analysis of one or more biomarkers, analysis component 1308 can determine a level of inflammation experienced by the user, a level of fatigue experienced by the user, or an energy level experienced by the user. Visualization component 1318 can further cause a user's avatar to appear a particular shade of red to indicate the degree of inflammation experienced by the user, a particular shade of blue to indicate a level of fatigue experienced by the user, and a particular shade of yellow to indicate the energy level of the user. In another example, analysis component 1308 can determine a degree of hydration of the user, whether the user has an electrolyte imbalance, and antioxidant levels of the user, or a glucose level of the user and visualization component 1318 can adapt a color of the avatar to reflect the respective physiological states. Still in yet another example, analysis component 1308 can determine a user's blood alcohol level, drug level, stress level (e.g., based on various stress related biomarkers), heart rate, and blood pressure, and visualization component 1318 can adapt a color of the avatar to reflect the respective physiological state.

Figure 15:
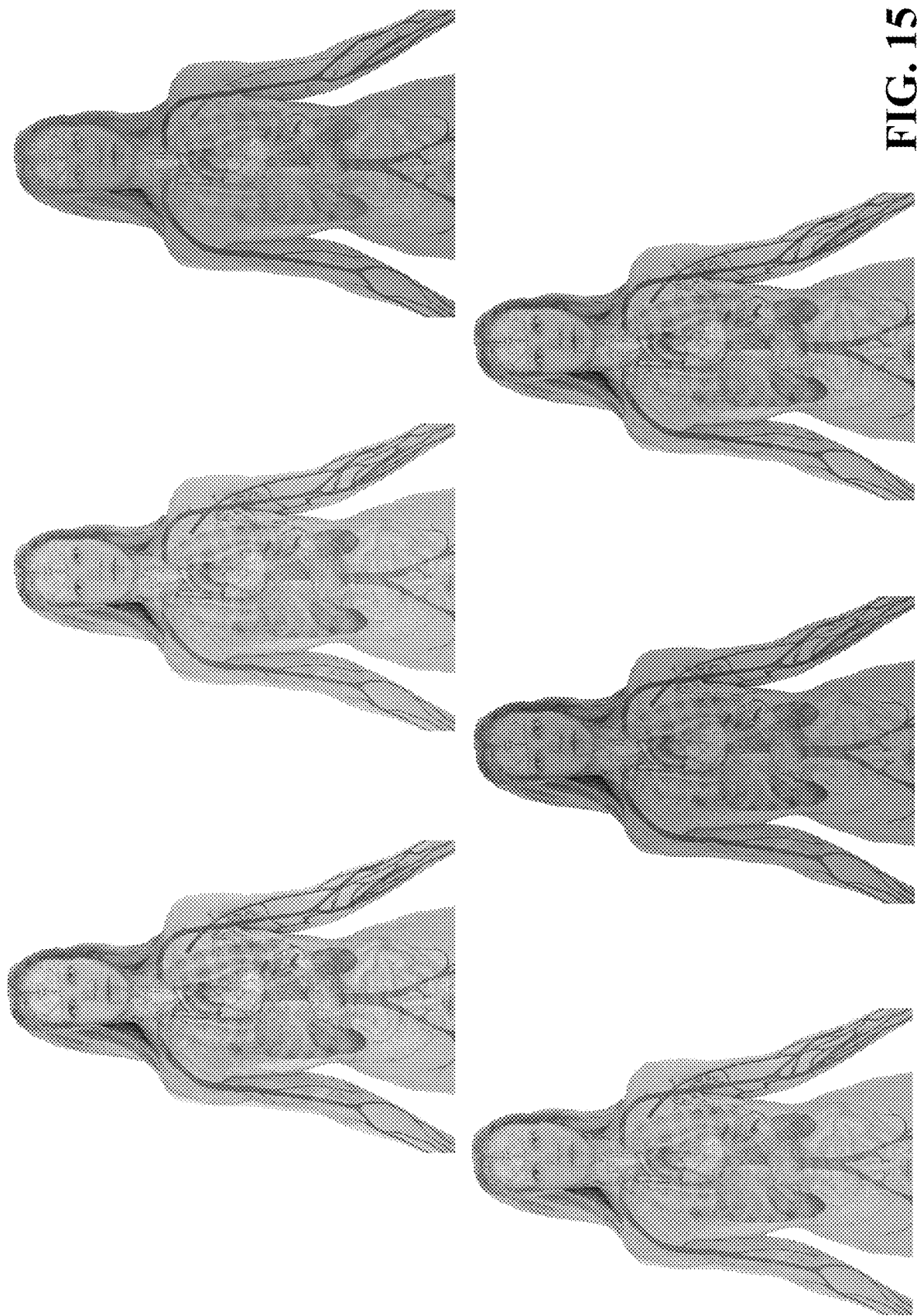
FIG. 15 presents additional example representations of an avatar that can be presented to a user in accordance with various aspects and embodiments described herein.

For example, FIG. 15 depicts a plurality of avatars presented in different colors. Each color can correspond to a particular physical/physiological state or condition exhibited by a user (e.g., over the course of a monitored routine, activity or program). For example, a natural colored avatar can indicate the user is in an optimal health state. A pink avatar can indicate the user is exhibiting a level of fatigue above a desired level. A red avatar can indicate the user is exhibiting severe levels of inflammation and exhaustion or injury. A yellow avatar can indicate the user has high glucose levels, high cholesterol levels, low antioxidant levels, etc. A green avatar can indicate the user is sick or becoming ill. A blue avatar can indicate the user is dehydrated or has an electrolyte imbalance. Accordingly, by looking at the color of one's avatar, a user can quickly and easily understand what is physiologically occurring in the user's body and react accordingly. It should be noted that the above described color correspondences to certain physiological states/condition of a user a merely exemplary. A wide variety of colors and different shades of colors can be used to signify one or more characteristics of a user's current physiological state.

Visualization component 1318 can cause the one or more parts of the body of the avatar to change in size or shape based on determined physiological states/conditions affecting a user (e.g., as determined based on received biometric/biochemical data for the user). For example, visualization component 1318 can cause certain body parts of a user that are inflamed to increase in size. In response to a determination that a user is bloated, visualization component 1318 can cause an avatar's stomach to appear bloated. Visualization component 1318 can also adapt the size of a user's stomach based on how recently the user has eaten (e.g., a full belly can be depicted larger than an empty belly). Visualization component 1318 can also adapt the size of various organs to reflect a degree to which the respective organs are underperforming or over performing. For example, visualization component 1318 can increase or decrease the size of an avatar's heart based an increase or decrease in a user's heart rate, respectively. In another example, visualization component 1318 can increase or decrease a size of an avatar's head based on a level of stress experienced by the user.

In some implementations, a particular appearance of a user's avatar can also reflect an actual physical appearance of the user based on captured image data for the user and information regarding the user's height, weight, BMI, etc. For example, a user's avatar can be adapted to resemble an actual current appearance of the user (e.g., mirror image or substantially mirror image). Based on this example, visualization component 1318 can generate an avatar that has a physical external appearance of the user based on captured image data of the user. In other aspect, a user's avatar can correspond to a general male or female human having one or more external physical feature similarities to the user.

Visualization component 1318 can also be configured to adapt a behavior of an avatar based on one or more characteristics of a user's physiological state or condition (e.g., as determined based on received biometric/biochemical information for a user). For example, visualization component 1318 can change a demeanor or body language of a user to reflect an energy level (e.g., tired, high strung), mood, or intoxication level of the user. In another example, visualization component can cause a user's avatar to perform certain predefined behaviors based on a physiological state/ condition of a user. For example, when a user is experiencing high stress level, visualization component 1318 can cause a user's avatar to appear stressed and bite his or her nails. When a user is exhausted or tired, visualization component 1318 can cause a user's avatar to lie down. In another example, when a user is hungry, visualization component 1318 can cause a user's avatar to appear holding onto a knife and fork and licking his or her lips.

The behavior of a user's avatar can also reflect actual behaviors of the user. For example, the avatar can be configured to mimic the movement and behavior of the user based on received input indicating a movement, motion or body position of the user. According to this example, if a user is walking, sitting, running, eating, etc., the avatar can likewise perform the movements or actions of walking, sitting, running, eating, etc. While performing these movements/behaviors, visualization component 1318 can also cause the avatar to have an appearance, facial expression, body language, tone of voice, etc., that reflect the current physiological states/conditions affecting the user. In addition, the facial expression, tone of voice, and body language of a user's avatar can change to reflect a user's current physiological state or condition. For example, if a user's is tired, the user's avatar can speak slower and at a lower volume and toner relative to a speed and volume when the user is energized.

The above described embodiments provide a user with a visual indicator of the user's physiological health and physical health at. The appearance and behavior of the avatar can change at any point in time based on reception of new user input. Thus depending on the mechanisms employed to receive the user input (e.g., manual user input, input received from external devices or testing service employed by the user, input receive by worn or implanted biosensing devices, etc.), a user's avatar can constantly adapt throughout the user's day or workout, or adapt each time new readings are taken (e.g., once a day, once a week, etc.). As a result, the user can quickly and easily look at his or her avatar and see a clear visual indication of what is going on with his or her mental and physical health and be encouraged to constantly and consciously adapt his or her behavior to improve or optimize the user's mental and physical well being.

In one embodiment, avatar visualization platform 1302 can also include a sharing component 1328 to facilitate sharing of a user's avatar with other users, such as via a virtual social networking community, an electronic notification message, or other form of electronic communication posting/sharing. In particular, as described above, a user's avatar can have an appearance and/or behavior that reflect a current physical/physiological state of a user and/or physical appearance of a user. Accordingly, a user can control the behavior and appearance of his or her avatar based on the user's lifestyle to reflect the user's healthy or unhealthy dietary habits, fitness practices, sleep habits, drug/alcohol intake, etc. As a means of motivation to improve one's mental and physical health or to achieve a desired physiological/physical state and/or appearance, a user can share his or her avatar with other users, for example via a social networking community, other virtual community, or in an electronic message. For example, a user's avatar can appear as the user's social networking symbol or icon as a representation of the user. The appearance and/or behavior of the avatar when employed as the user's social networking symbol or icon can continuously update in response to changes in the user's physical/physiological state and appearance. Accordingly, other user's will be able to clearly see when a user's physical and/or mental health is deteriorating and/or improving and provide encouragement or praise to keep the user on track to achieve his or her mental/physical health goals (e.g., such as those defined by a program the user has elected to follow).

In various embodiments, avatar visualization platform 1302 is further configured to generate a visual representation of the user that is a prediction of how the user will appear at a future point in time based on performance of a health and fitness program by the user. For example, the user can select, (and/or design, or otherwise be assigned) a specific health and fitness program for performance using fitness module 1302 (wherein fitness module 1302 can include same or similar features and functionalities of fitness module 230). Using avatar visualization platform 1302, the user can be provided a visual representation that demonstrates how the will predicatively look after performance/completion of the program if the user adheres to the requirements of the program. In addition, the user can select various time points in the program (e.g., after week 1, after week 2, after week 3, etc.) and avatar visualization platform 1302 can generate a visual representation of the user that demonstrates how the user will predicatively look at the respective time points if the user adheres to the requirements of the program.

This feature of avatar visualization platform 1302 allows a user to dynamically pick and choose different health and fitness programs and/or change different variables of a health and fitness program and see how the user would appear in the future based on the selected health and fitness program and/or the different variables. Accordingly, a user can select a health and fitness program that will cause the user to achieve an optimally desired appearance. For example, as the user selects different health and fitness programs and/or can changes variables of a selected health and fitness program, avatar visualization platform 1302 can dynamically adapt the appearance of an avatar presented to the user that corresponds to a predicted visualization of how the user will appear based on completion and adherence to the different health and fitness or the health and fitness program with the respectively chosen variables. As a result, the user can select a health and fitness program based on how it will affect the user's appearance.

In an aspect, the avatar is generated and presented to the user via a rendering component 1324 located at a client device (e.g., client device 106). Rendering component 1324 can include suitable hardware (e.g., a display screen, a hologram generation device, etc.) and software (e.g., software for generating a GUI and/or software for accessing and rendering network based interface, such a browser) to accomplish generating and presenting an avatar. Generally, avatar visualization platform 1302 can include memory 1312 that stores computer executable components and processor 1322 that executes the computer executable components stored in the memory, examples of which can be found with reference to FIG. 20.

It is to be appreciated that although avatar guidance visualization platform 1302 is illustrated as being a stand-alone component, such implementation is not so limited. For example, avatar visualization platform 1302 can be located at a client device (e.g., client device 106), a remote server (e.g., avatar server 116) or the cloud. In another aspect, one or more components of avatar visualization platform 1302 can be located at both the client device and the remote server. In yet another aspect, the components of avatar guidance platform can be distributed between the client and the server. Still in yet another aspect, avatar visualization platform 1302 can be included within avatar guidance platform 202, or vice versa. All or portions of avatar visualization platform 1302 can be operatively coupled to all or portions of avatar guidance platform 202, or vice versa. Moreover, avatar visualization platform 1302 can be granted access to all or portions of avatar guidance platform 202, or vice versa.

Avatar visualization platform 1302 can include reception component 1302, processing module 1306, interface component 1316, visualization component 1318 and program guide module 1320. Reception component 1302 is configured to receive various inputs 1322 including the data noted with respect to input 234. In accordance with aspects of avatar visualization platform 1302, input 1322 particularly includes a variety of information about the user's physical health and appearance. In an aspect, this physical health and/or appearance information is provided by the user (or another user such as the user's medical caregiver or therapist) or extracted from a remote system/source (e.g., electronic medical/health records for the user provided by a medical institution). In another aspect, physical health and/or appearance information for a user is captured via various sensing devices 106 worn by or otherwise attached to the user, intelligent fitness device(s) employed by the user (e.g., intelligent fitness devices 118), other remote medical/sensing equipment employed by the user (e.g., a heart monitor, a scale, etc.), and/or a visual capture device (e.g., visual capture device 110) pointed at the user. In an aspect, health and/or appearance information is received by reception component 1304 during a capture process prior to generation of a visual replica of the user. In another aspect, this physical health and/or appearance data can be received for the user in real-time as the user performs a fitness routine or health and fitness program.

In an aspect, physical health and appearance information received for a user is stored by avatar visualization platform 1302 in association with a user profile established for the user (e.g., user profile data 1314). User profile data 1314 can also include the various profile information described with respect to user profile data 222. For example, a user can establish a profile with avatar visualization platform 1302 that includes information defining the user's preferences (e.g., diet and exercises preferences), health information, demographics and schedule. The profile can also include a logged history of captured physical and physiological activity data for the user over the course of performance of various fitness and/or other programs by the user (e.g., using avatar guidance platform 202), and other logged/monitored information for the user (e.g., habits, food and drink consumption, activities levels, sleep patterns, etc.).

Physical health information for a user can include any information regarding a user's mental and physical health. For example, physical health information can include but is not limited to: physical measurements (e.g., height, weight, BMI) of the user, physical and physiological conditions effecting the user, mental illness, any past or current physical injuries affecting the user, surgeries received by the user, history of medical conditions associated with the user and the user's relatives, any medications taken by the user, and tobacco and alcohol consumption of the user etc. Health information can also include information related to physiological indicators/measures that are capable of being determined for a user using various know clinical laboratory tests, including information related to the user's genetic make-up, protein levels, hormone levels, blood type, white/red blood cell count, metabolism, etc. Health information can also include information regarding physical fitness practices and abilities of the user (e.g., how fast the user can run, how high the user can jump, how much weight the user can lift, flexibility of the user, range of motion of the user, etc.).

Appearance information for a user includes two or three-dimensional image data captured/taken of the user. For example, the user can have image data taken of himself or herself (e.g., a picture, a video, a series of three-dimensional image data captures of the user from different camera perspectives relative to the user, etc.) as the user stands still and/or as the user performs various test/model movements (e.g., using a visual capture device 110). At this time, data regarding the user's physiological state can also be captured by various medical devices or biometric sensing devices (e.g., devices 106) and received by reception component 1304. For example, the physiological data captured and provided to reception component 1304 (e.g., via a wired or wireless connection) can include information regarding the user's blood pressure, perspiration, respiration, white blood cell count, temperature, glucose level, drugs present in the body, antigens present in the body, etc. Other example data that can be captured and reported by a sensing/medical device can include information indicating the user's physical measurements (e.g., height, weight, BMI, etc.).

In an aspect, image data captured for a user is used to generate a visual representation of the user corresponding to the user's current appearance. In one aspect, the visual capture device employed to capture the image data (e.g., visual capture device 110) can generate this visual representation. In another aspect, the visual capture device can provide the captured image data to reception component 1304 and visualization component 1318 can employ the image data to generate the three dimensional representation of the user as the user currently appears. For example, visualization component 1318 can generate an avatar that resembles the current appearance of the user. Interface component 1316 is configured to generate a graphical user interface that includes the avatar. In an aspect, interface component 1316 can include same or similar functionalities as interface component 206. An interface including an avatar generated by visualization component 1318 is further presented to the user via rendering component 1324.

In an aspect, an avatar generated by visualization component 1318 can further be configured to exhibit the various features and functionalities of avatars discussed herein. For example, an avatar generated by visualization component 1318 that resembles the appearance of a user can function as the user's guide or coach in association with performance of a monitored program, routine or activity, as discussed with respect to avatar guidance system 200.

In addition to generating an avatar that resembles a user's current appearance. Visualization component 1318 is further configured to generate a visual representation of the user that is a prediction of how the user will appear at a future point in time based on performance of a health and fitness program by the user. In particular, processing module 1306 is configured to analyze received input regarding a user's current appearance and determine or infer how the user's appearance will change in response to performance of specific health and fitness program based on the user' current physical appearance, the user's health information (as included in the user's profile), other profile information for the user (e.g., age, gender, ethnicity, etc.), and the requirements of the health and fitness routine.

For example analysis component 1308 can employ information relating different diet and exercise program, and/or features of the respective programs to measurable appearance metrics including but not limited to: to weight loss, weight gain, fat loss, fat gain, dimensions of body parts, and muscle definition/appearance, with respect to individual human body parts and/or the human body as a whole. Analysis component 1308 can further adjust these appearance metrics to account for specific health information for the user (e.g., physical measurements, physical conditions, surgeries received, medications taken, dietary restrictions, metabolism, and other health information), along with information regarding the user's age, gender, ethnicity, and/or any other personal information that can have an effect on a user's body appearance and function. For example, the manner in which a specific diet and exercise regimen changes the amount of inches lost and muscle definition established with respect to a user's abdominal area can depend on the user's health profile, age and gender.

Analysis component 1308 can thus determine how a particular user's body and appearance will likely change based on a specific diet and/or exercise regimen. Based on these determined changes, visualization component 1318 can generate a visual representation of the user that depicts how the user will look following performance of the specific diet and/or exercise regimen. In an aspect, visualization component 1318 can modify current image data of a user to account for the changes determined by analysis component 1308. For example, visualization component 1318 can generate an avatar depicting the user as the user currently appears and morph the avatar's appearance, based on the changes determined by analysis component 1308, to generate a new visual representation of the user depicting how the user will appear after performance of the diet and exercise regimen.

In some aspects, analysis component 1308 can specifically determine how a user's body will change at different points over the course of a health and fitness program. According to this aspect, a user can request to see a visualization of how he or she will appear at any point during the health and fitness program. For example, when a user has selected a 90 day program, before beginning the program, the user can be provided with a visualization of how he or she would look after completion of the program. The user could also request to see how he or she would look on day 10, on day 32, on day 45, etc., and visualization component can 1318 generate the respective visual representations of the user. According to this aspect, analysis component 1308 can determine how a user's appearance will change based on analysis of the user's current appearance, health information, and age/gender in view of what will be performed by the user (e.g., diet and exercise wise), over the duration of time from the initiation of the program to the selected time marker.

In an aspect, analysis component 1308 can employ inference component to facilitate inferring how the user's appearance will change in response to performance of the specific health and fitness program based on the user' current physical appearance, the user's health information, and the requirements of the health and fitness routine. Inference component 1310 can include same or similar features and functionalities as inference component 216. In an aspect, inference component 1308 analyze appearance information for a plurality of user's regarding how performance of different health and fitness routines and regimes effected changes in their appearance in view of respective health information (e.g., starting height, weight, BMI, age, ethnicity, medications taken, physical conditions, physical abilities, etc.) for the different users. Inference component 1308 can further employ various machine learning techniques to optimize determinations regarding how a specific user's appearance will be affected by different health and fitness programs (e.g., including specific diet and fitness requirements of the different health and fitness programs).

For example, inference component 1308 can analyze historical performance and appearance information for a set of users having a similar health profile, age and gender as a current user. Inference component 1308 can then determine how performance of these different health and fitness programs actually affected changes their respective appearance and employ this information to infer how performance of the different health and fitness routines will affect the current user's appearance. In an aspect, visualization component 1318 present a user with example images of before and after visualizations/pictures taken of other user's who performed the different health and fitness programs.

Avatar visualization platform 1302 can also include program guide module 1320. Program guide module 1320 can include same or similar functionality as program guide module 232. In particular, program guide module 1320 can include program selection component 902, a program builder component 904. Using these respective components, a user can select or design a specific health and fitness program. The program builder component 904 can also employ various features of fitness module 230 (e.g., routine selection component 404, routine builder component 406, etc.) to facilitate selecting or designing specific fitness routines/activities for inclusion in a health and fitness program. The requirements of a fitness program selected/designed by the user can vary but can generally relate to dietary requirements, fitness requirements, and duration of the program. Based on the health and fitness program selected or designed by the user, visualization component 1318 can generate a representation of the user as the user will appear in response to performance of the program. Accordingly, a user can employ avatar visualization component 1318 in conjunction with fitness module 1320 to facilitate selecting/designing a health and fitness program that will bring about desired changes in the user's appearance.

Figure 16:
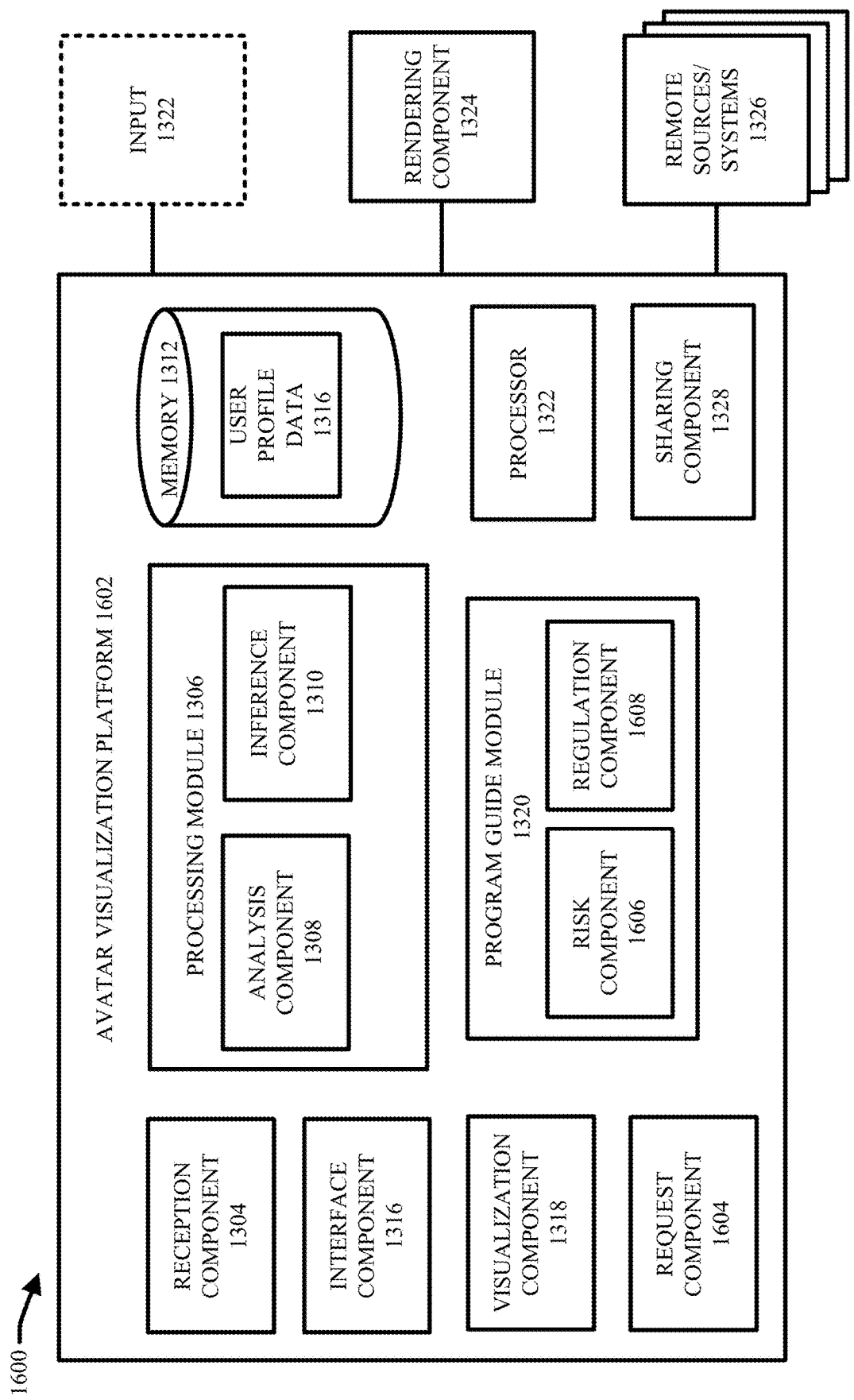
FIG. 16 presents another example avatar visualization system that facilitates visualizing how the user will appear in response to adhering to a health and fitness program in accordance with various aspects and embodiments described herein.
Figure 17:
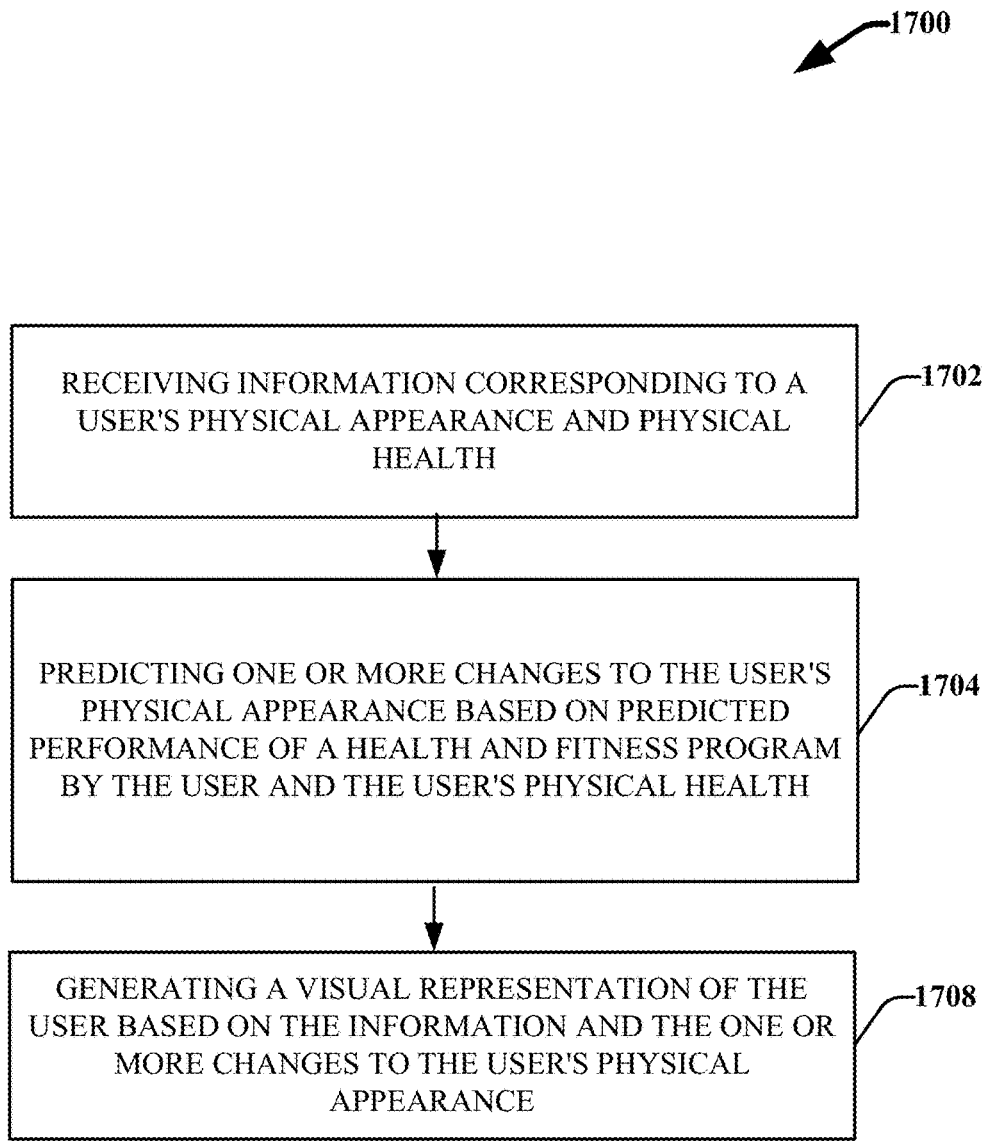
FIG. 17 presents a flow diagram of an example method that facilitates visualizing how the user will appear in response to adhering to a health and fitness program in accordance with various aspects and embodiments described herein.

FIG. 16 presents another example avatar visualization system 1600 that facilitates visualizing how the user will appear in response to adhering to a health and fitness program in accordance with various aspects and embodiments described herein. System 1600 can include same or similar features and functionalities as system 1300, with the addition of request component 1604, risk component 1606 and regulation component 1608 to program guide module 1320. Repetitive description of like elements employed in respective embodiments of systems and interfaces described herein are omitted for sake of brevity.

Avatar visualization platform 1602 is configured to facilitate designing a health and fitness program to achieve a desired visual appearance of the user. In an aspect, a user can provide a request via request component 1604 that includes information identifying one or more characteristics of the user's body that the user would like to achieve. Based on the request, the user's current appearance, and the user's health and physical/physiological state information, program guide module 1320 (e.g., via program builder component 904), can generate a personalized diet and exercise program for the user that is designed to cause the user's appearance to changed in the requested manner.

For example, the user could submit a request via request component 1604 indicating how she would like her stomach to appear, her hips to appear, her thighs to appear, etc. The request can also indicate how much the weight the user would like to lose or gain and/or how much muscle the user would like to lose or gain. In another example, the request can include information regarding muscle toning. The request can also provide a timeline for when the use user would like to achieve the changes to the user's appearance.

In an aspect, in order to identify physical characteristics the user would like to obtain using a health and fitness plan, the user can critique an image of himself or herself or avatar generated by visualization component 1318 that represents the user's appearance. For example, visualization component 1318 can generate an avatar that is presented to the user and represents the user's current appearance. Using the visualization, the user can point out various aspects of the user's physical features that the user would like to change and how the user would like to change them. For example, the user could indicate (e.g., by drawing on or marking up the avatar representation) where the user would like to gain muscle and how much muscle the user would like to gain. In another example, the user could mark places on his or her body whether he or she would like to trim fat or tone up.

In another aspect, in order to identify physical characteristics the user would like to obtain using a health and fitness plan, the user provide an image of a person's body that the user's would like his or her body to resemble, or a particular body part that the user would like have his or her corresponding body part resemble. For example, in association with a request for a custom diet and fitness plan, the user can provide an image of himself or herself when they were in great shape years prior or a picture of a famous fitness model. In another example, the user could provide an image of a set of abdominals that the user would like his or her abdominals to look like.

In some respects, a user's aspirations may be unachievable or unhealthy. For example, a user may request he or she would like to appear a certain way within a period of two weeks and this request would require loosing of an unhealthy amount of weight too quickly. Accordingly, program guide module 1320 can include risk component 1606 and regulation component 1608. Risk component 1606 is configured to evaluate a request and determine health risks associated with achieving the one or more desired changes to the user's physical appearance identified in the request based on the user's current appearance and health, profile information for the user and various existing health standards. In an aspect, when a request provides a duration of time over which the user would like to achieve the physical changes, risk component 1606 can also consider whether the user's aspirations are reasonable and/or achievable in a healthy manner within the duration of time.

Based on the health risks identified or determined by risk component 1606 regulation component 1608 is configured to determine whether the user's goal is obtainable in a healthy and safe manner (e.g., based on various health standards and risk allowance thresholds). For example, regulation component 1608 can return a response to a user's request indicating that the user's goal is or is not possible over the desired duration in a healthy manner and/or that the user's goal is not a recommended healthy goal (e.g., based on various existing health standards). For example, the user may desire to achieve a weight that is unhealthy for the user's height, age, and/or physical training routine (e.g., where the user is an athlete required to perform various physical activities). In an aspect, regulation component 1608 can automatically adjust aspects of a user's request to accommodate risks identified by risk component 1606. For example, regulation component 1608 can increase the duration of time of a health and fitness program to a duration that allows the user to achieve his or her goal in a reasonable manner. In another example, regulation component 1608 can slightly modify physical the degree of physical changes (e.g., the amount of weight lost/gained) request by the user to a reasonable value.

FIG. 20 illustrates a flow chart of an example method 2000 for generating a visualization representing how a user will appear in response to adhering to a health and fitness program, in accordance with various aspects and embodiments described herein. At 2002, information corresponding to a user's physical appearance and physical health is received (e.g., via reception component 1304). At 2004, one or more changes to the user's physical appearance are predicted based on predicted performance of a health and fitness program by the user and the user's physical health (e.g., via processing module 1306). At 2006, a visual representation of the user is generated based on the information and the one or more changes to the user's physical appearance (e.g., via visualization component 1318).

Figure 18:
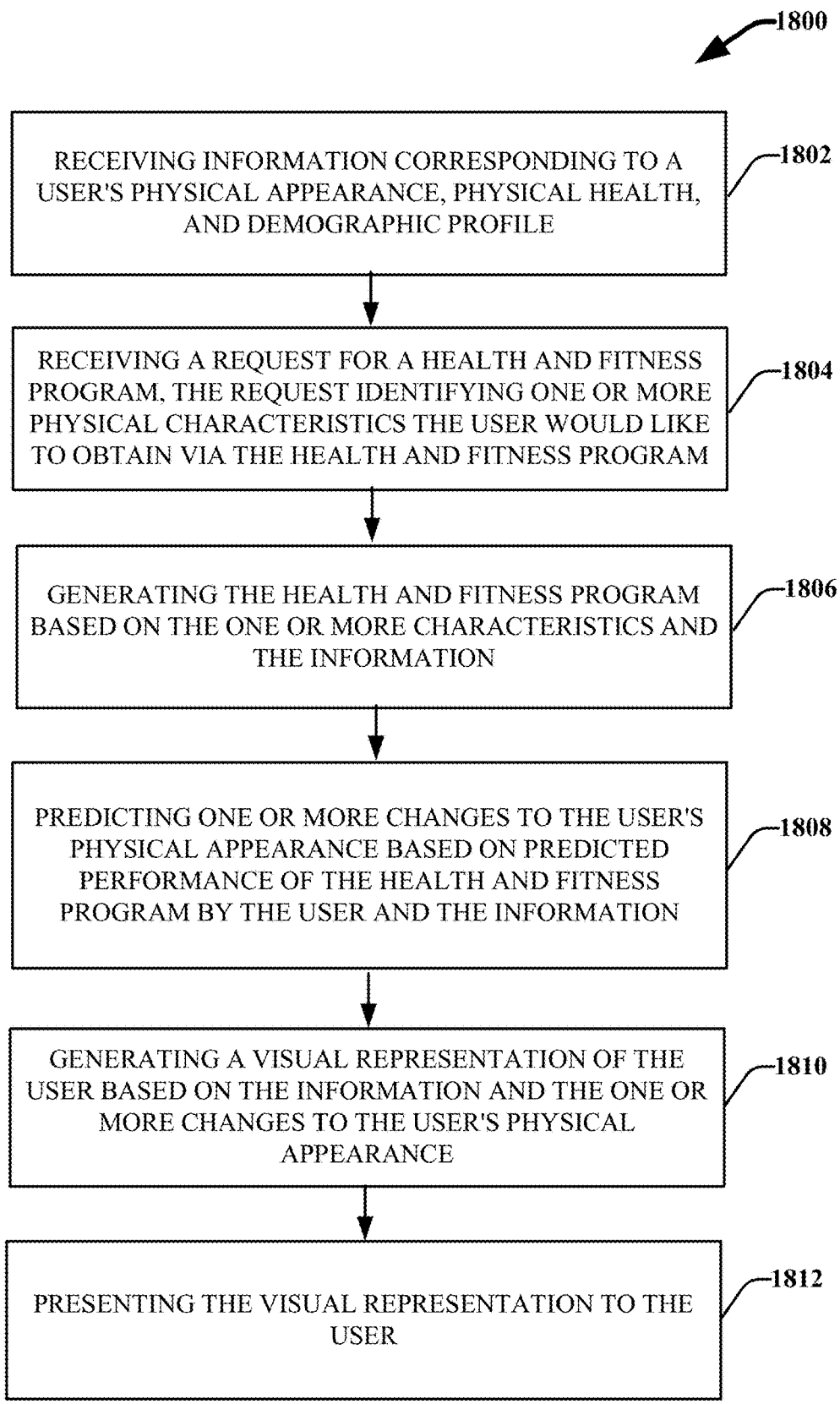
FIG. 18 presents a flow diagram of another example method that facilitates visualizing how the user will appear in response to adhering to a health and fitness program in accordance with various aspects and embodiments described herein.

FIG. 18 illustrates a flow chart of another example method 1800 for generating a visualization representing how a user will appear in response to adhering to a health and fitness program, in accordance with various aspects and embodiments described herein. At 1802, information corresponding to a user's physical appearance, physical health and demographic profile is received (e.g., via reception component 1304). At 1804, a request is received for a health and fitness program, the request identifying one or more physical characteristics the user would like to obtain via the health and fitness program (e.g., via request component 1402). At 1806, the health and fitness program is generated based on the one or more characteristics and the information (e.g., via program guide module 1320). At 1808, one or more changes to the user's physical appearance are predicted based on predicted performance of a health and fitness program by the user and the user's physical health (e.g., via processing module 1306). At 1810, a visual representation of the user is generated based on the information and the one or more changes to the user's physical appearance (e.g., via visualization component 1318).

Figure 19:
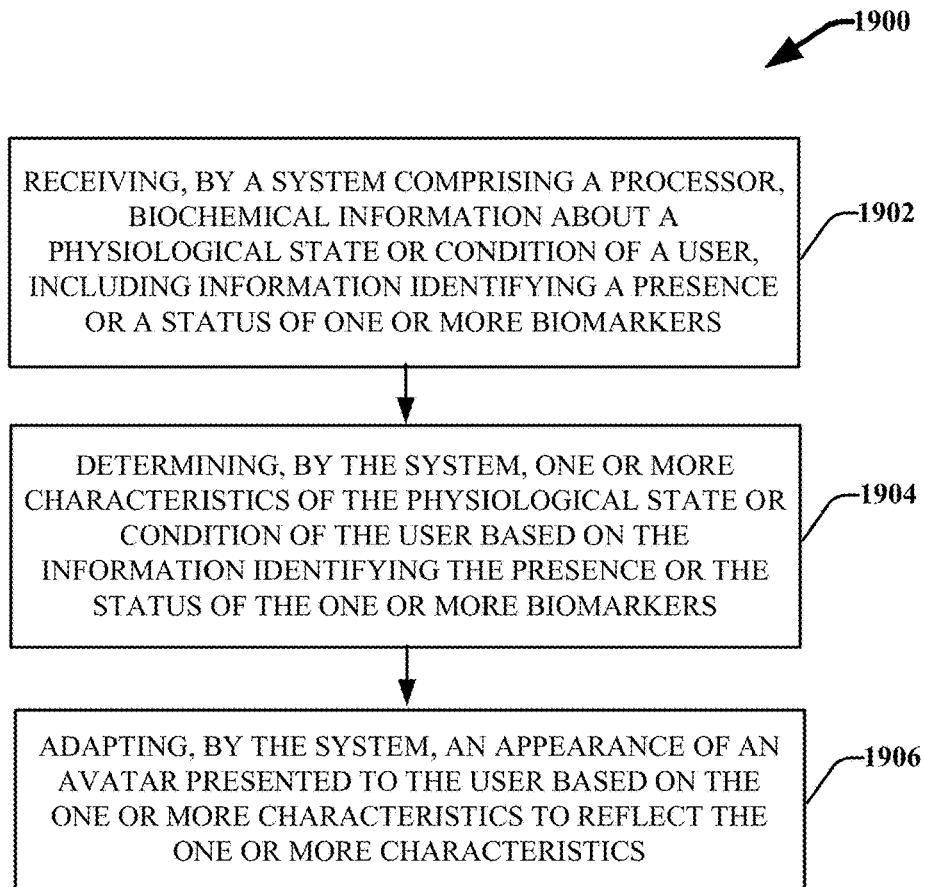
FIG. 19 presents a flow diagram of an example method for generating and presenting an avatar having an appearance based on a current physical/physiological state of a user in accordance with aspects and embodiments described herein.

FIG. 19 illustrates a flow chart of another example method 1900 for generating an avatar having an appearance that corresponds to a current physical/physiological state of a user in accordance with various aspects and embodiments described herein. At 1902, a system comprising a processor receives biochemical information about a physiological state or condition of a user, including information identifying a presence or a status of one or more biomarkers (e.g., via reception component 1304). For example, the system can receive biochemical feedback from a boisensing device or apparatus worn or implanted into the user, or a handheld biosensing spectroscopic biosensing device employed by the user. At 1904, the system determines (e.g., via analysis component 1308) one or more characteristics of the physiological state or condition of the user based on the information identifying the presence or the status of the one or more biomarkers. For example, the system can determine a level or concentration of one or more biomarkers present in the body and/or whether the level/concentration of the one or more biomarkers is within an acceptable range. The system can also determine a physiological state or condition of the user based on the biomarker levels. Then at 1906, the system adapts an appearance of an avatar presented to the user based on the one or more characteristics to reflect the one or more characteristics. For example, the system can cause one or more parts of the avatar to change in color, size, or shape based on the one or more characteristics.

V—Example Operating Environments

The systems and processes described below can be embodied within hardware, such as a single integrated circuit (IC) chip, multiple ICs, an application specific integrated circuit (ASIC), or the like. Further, the order in which some or all of the process blocks appear in each process should not be deemed limiting. Rather, it should be understood that some of the process blocks can be executed in a variety of orders, not all of which may be explicitly illustrated in this disclosure.

With reference to FIG. 20, a suitable environment 2000 for implementing various aspects of the claimed subject matter includes a computer 2002. The computer 2002 includes a processing unit 2004, a system memory 2006, a codec 2005, and a system bus 2008. The system bus 2008 couples system components including, but not limited to, the system memory 2006 to the processing unit 2004. The processing unit 2004 can be any of various available processors. Dual microprocessors and other multiprocessor architectures also can be employed as the processing unit 2004.

The system bus 2008 can be any of several types of bus structure(s) including the memory bus or memory controller, a peripheral bus or external bus, and/or a local bus using any variety of available bus architectures including, but not limited to, Industrial Standard Architecture (ISA), Micro-Channel Architecture (MSA), Extended ISA (EISA), Intelligent Drive Electronics (IDE), VESA Local Bus (VLB), Peripheral Component Interconnect (PCI), Card Bus, Universal Serial Bus (USB), Advanced Graphics Port (AGP), Personal Computer Memory Card International Association bus (PCMCIA), Firewire (IEEE 104), and Small Computer Systems Interface (SCSI).

The system memory 2006 includes volatile memory 10 and non-volatile memory 2012. The basic input/output system (BIOS), containing the basic routines to transfer information between elements within the computer 2002, such as during start-up, is stored in non-volatile memory 2012. In addition, according to present innovations, codec 2005 may include at least one of an encoder or decoder, wherein the at least one of an encoder or decoder may consist of hardware, a combination of hardware and software, or software. Although, codec 2005 is depicted as a separate component, codec 2005 may be contained within non-volatile memory 2012. By way of illustration, and not limitation, non-volatile memory 2012 can include read only memory (ROM), programmable ROM (PROM), electrically programmable ROM (EPROM), electrically erasable programmable ROM (EEPROM), or flash memory. Volatile memory 10 includes random access memory (RAM), which acts as external cache memory. According to present aspects, the volatile memory may store the write operation retry logic (not shown in FIG. 20) and the like. By way of illustration and not limitation, RAM is available in many forms such as static RAM (SRAM), dynamic RAM (DRAM), synchronous DRAM (SDRAM), double data rate SDRAM (DDR SDRAM), and enhanced SDRAM (ESDRAM.

Computer 2002 may also include removable/non-removable, volatile/non-volatile computer storage medium. FIG. 20 illustrates, for example, disk storage 2011. Disk storage 2011 includes, but is not limited to, devices like a magnetic disk drive, solid state disk (SSD) floppy disk drive, tape drive, Jaz drive, Zip drive, LS-70 drive, flash memory card, or memory stick. In addition, disk storage 2011 can include storage medium separately or in combination with other storage medium including, but not limited to, an optical disk drive such as a compact disk ROM device (CD-ROM), CD recordable drive (CD-R Drive), CD rewritable drive (CD-RW Drive) or a digital versatile disk ROM drive (DVD-ROM). To facilitate connection of the disk storage devices 2011 to the system bus 2008, a removable or non-removable interface is typically used, such as interface 2016.

It is to be appreciated that FIG. 20 describes software that acts as an intermediary between users and the basic computer resources described in the suitable operating environment 2000. Such software includes an operating system 2018. Operating system 2018, which can be stored on disk storage 2011, acts to control and allocate resources of the computer system 2002. Applications 2020 take advantage of the management of resources by operating system 2018 through program modules 2024, and program data 2026, such as the boot/shutdown transaction table and the like, stored either in system memory 2006 or on disk storage 2011. It is to be appreciated that the claimed subject matter can be implemented with various operating systems or combinations of operating systems.

A user enters commands or information into the computer 2002 through input device(s) 2028. Input devices 2028 include, but are not limited to, a pointing device such as a mouse, trackball, stylus, touch pad, keyboard, microphone, joystick, game pad, satellite dish, scanner, TV tuner card, digital camera, digital video camera, web camera, and the like. These and other input devices connect to the processing unit 2004 through the system bus 2008 via interface port(s) 2030. Interface port(s) 2030 include, for example, a serial port, a parallel port, a game port, and a universal serial bus (USB). Output device(s) 2036 use some of the same type of ports as input device(s). Thus, for example, a USB port may be used to provide input to computer 2002, and to output information from computer 2002 to an output device 2036. Output adapter 2034 is provided to illustrate that there are some output devices 2036 like monitors, speakers, and printers, among other output devices 2036, which require special adapters. The output adapters 2034 include, by way of illustration and not limitation, video and sound cards that provide a means of connection between the output device 2036 and the system bus 2008. It should be noted that other devices and/or systems of devices provide both input and output capabilities such as remote computer(s) 2038.

Computer 2002 can operate in a networked environment using logical connections to one or more remote computers, such as remote computer(s) 2038. The remote computer(s) 2038 can be a personal computer, a server, a router, a network PC, a workstation, a microprocessor based appliance, a peer device, a smart phone, a tablet, or other network node, and typically includes many of the elements described relative to computer 2002. For purposes of brevity, only a memory storage device 2040 is illustrated with remote computer(s) 2038. Remote computer(s) 2038 is logically connected to computer 2002 through a network interface 2042 and then connected via communication connection(s) 2044. Network interface 2042 encompasses wire and/or wireless communication networks such as local-area networks (LAN) and wide-area networks (WAN) and cellular networks. LAN technologies include Fiber Distributed Data Interface (FDDI), Copper Distributed Data Interface (CDDI), Ethernet, Token Ring and the like. WAN technologies include, but are not limited to, point-to-point links, circuit switching networks like Integrated Services Digital Networks (ISDN) and variations thereon, packet switching networks, and Digital Subscriber Lines (DSL).

Communication connection(s) 2044 refers to the hardware/software employed to connect the network interface 2042 to the bus 2008. While communication connection 2044 is shown for illustrative clarity inside computer 2002, it can also be external to computer 2002. The hardware/software necessary for connection to the network interface 2042 includes, for exemplary purposes only, internal and external technologies such as, modems including regular telephone grade modems, cable modems and DSL modems, ISDN adapters, and wired and wireless Ethernet cards, hubs, and routers.

Figure 21:
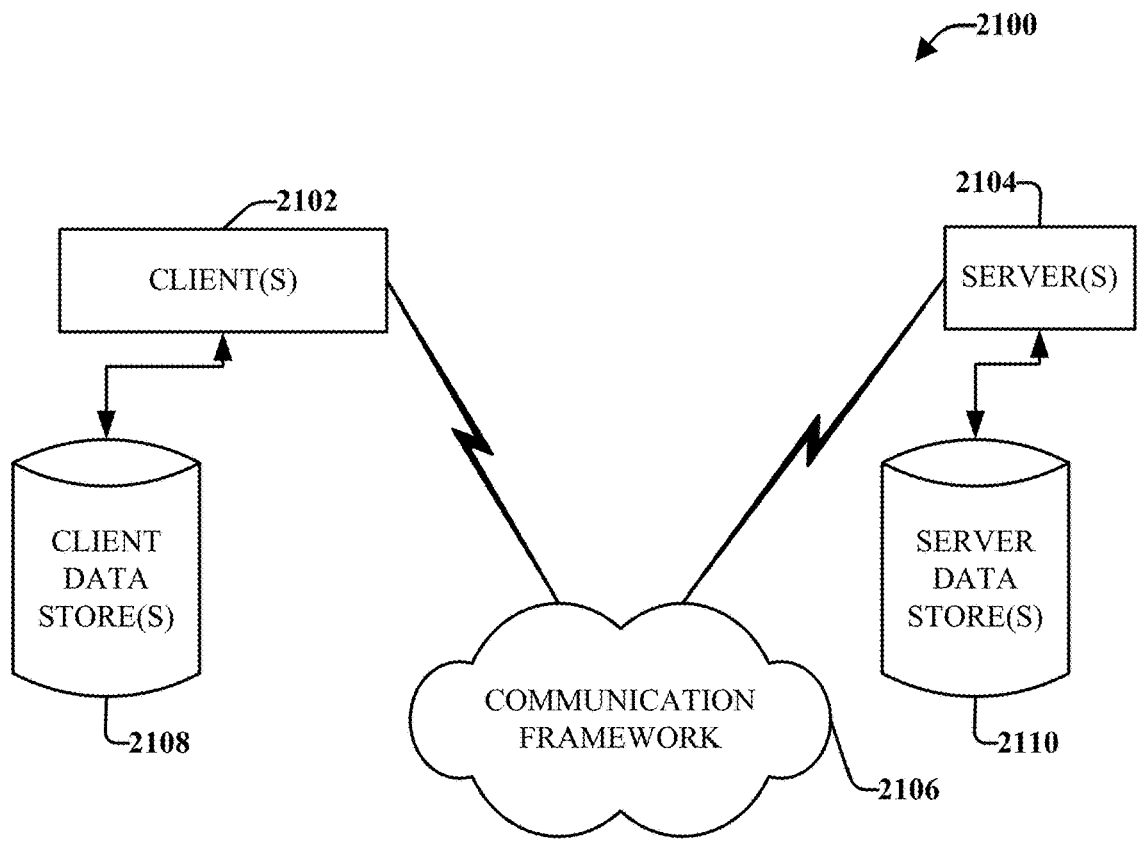
FIG. 21 is a schematic block diagram of a sample-computing environment in accordance with various aspects and embodiments.

Referring now to FIG. 21, there is illustrated a schematic block diagram of a computing environment 2100 in accordance with this disclosure. The system 2100 includes one or more client(s) 2102 (e.g., laptops, smart phones, PDAs, media players, computers, portable electronic devices, tablets, and the like). The client(s) 2102 can be hardware and/or software (e.g., threads, processes, computing devices). The system 2100 also includes one or more server(s) 2104. The server(s) 2104 can also be hardware or hardware in combination with software (e.g., threads, processes, computing devices). The servers 2104 can house threads to perform transformations by employing aspects of this disclosure, for example. One possible communication between a client 2102 and a server 2104 can be in the form of a data packet transmitted between two or more computer processes wherein the data packet may include video data. The data packet can include a metadata, e.g., associated contextual information, for example. The system 2100 includes a communication framework 2106 (e.g., a global communication network such as the Internet, or mobile network(s)) that can be employed to facilitate communications between the client(s) 2102 and the server(s) 2104.

Communications can be facilitated via a wired (including optical fiber) and/or wireless technology. The client(s) 2102 include or are operatively connected to one or more client data store(s) 2108 that can be employed to store information local to the client(s) 2102 (e.g., associated contextual information). Similarly, the server(s) 2104 are operatively include or are operatively connected to one or more server data store(s) 2110 that can be employed to store information local to the servers 2104.

In one embodiment, a client 2102 can transfer an encoded file, in accordance with the disclosed subject matter, to server 2104. Server 2104 can store the file, decode the file, or transmit the file to another client 2102. It is to be appreciated, that a client 2102 can also transfer uncompressed file to a server 2104 and server 2104 can compress the file in accordance with the disclosed subject matter. Likewise, server 2104 can encode video information and transmit the information via communication framework 2106 to one or more clients 2102.

The illustrated aspects of the disclosure may also be practiced in distributed computing environments where certain tasks are performed by remote processing devices that are linked through a communications network. In a distributed computing environment, program modules can be located in both local and remote memory storage devices.

Moreover, it is to be appreciated that various components described in this description can include electrical circuit(s) that can include components and circuitry elements of suitable value in order to implement the embodiments of the subject innovation(s). Furthermore, it can be appreciated that many of the various components can be implemented on one or more integrated circuit (IC) chips. For example, in one embodiment, a set of components can be implemented in a single IC chip. In other embodiments, one or more of respective components are fabricated or implemented on separate IC chips.

What has been described above includes examples of the embodiments of the present invention. It is, of course, not possible to describe every conceivable combination of components or methodologies for purposes of describing the claimed subject matter, but it is to be appreciated that many further combinations and permutations of the subject innovation are possible. Accordingly, the claimed subject matter is intended to embrace all such alterations, modifications, and variations that fall within the spirit and scope of the appended claims. Moreover, the above description of illustrated embodiments of the subject disclosure, including what is described in the Abstract, is not intended to be exhaustive or to limit the disclosed embodiments to the precise forms disclosed. While specific embodiments and examples are described in this disclosure for illustrative purposes, various modifications are possible that are considered within the scope of such embodiments and examples, as those skilled in the relevant art can recognize.

In particular and in regard to the various functions performed by the above described components, devices, circuits, systems and the like, the terms used to describe such components are intended to correspond, unless otherwise indicated, to any component which performs the specified function of the described component (e.g., a functional equivalent), even though not structurally equivalent to the disclosed structure, which performs the function in the disclosure illustrated exemplary aspects of the claimed subject matter. In this regard, it will also be recognized that the innovation includes a system as well as a computer-readable storage medium having computer-executable instructions for performing the acts and/or events of the various methods of the claimed subject matter.

The aforementioned systems/circuits/modules have been described with respect to interaction between several components/blocks. It can be appreciated that such systems/circuits and components/blocks can include those components or specified sub-components, some of the specified components or sub-components, and/or additional components, and according to various permutations and combinations of the foregoing. Sub-components can also be implemented as components communicatively coupled to other components rather than included within parent components (hierarchical). Additionally, it should be noted that one or more components may be combined into a single component providing aggregate functionality or divided into several separate sub-components, and any one or more middle layers, such as a management layer, may be provided to communicatively couple to such sub-components in order to provide integrated functionality. Any components described in this disclosure may also interact with one or more other components not specifically described in this disclosure but known by those of skill in the art.

In addition, while a particular feature of the subject innovation may have been disclosed with respect to only one of several implementations, such feature may be combined with one or more other features of the other implementations as may be desired and advantageous for any given or particular application. Furthermore, to the extent that the terms "includes," "including," "has," "contains," variants thereof, and other similar words are used in either the detailed description or the claims, these terms are intended to be inclusive in a manner similar to the term "comprising" as an open transition word without precluding any additional or other elements.

As used in this application, the terms "component," "module," "system," or the like are generally intended to refer to a computer-related entity, either hardware (e.g., a circuit), a combination of hardware and software, software, or an entity related to an operational machine with one or more specific functionalities. For example, a component may be, but is not limited to being, a process running on a processor (e.g., digital signal processor), a processor, an object, an executable, a thread of execution, a program, and/or a computer. By way of illustration, both an application running on a controller and the controller can be a component. One or more components may reside within a process and/or thread of execution and a component may be localized on one computer and/or distributed between two or more computers. Further, a "device" can come in the form of specially designed hardware; generalized hardware made specialized by the execution of software thereon that enables the hardware to perform specific function; software stored on a computer readable storage medium; software transmitted on a computer readable transmission medium; or a combination thereof.

Moreover, the words "example" or "exemplary" are used in this disclosure to mean serving as an example, instance, or illustration. Any aspect or design described in this disclosure as "exemplary" is not necessarily to be construed as preferred or advantageous over other aspects or designs. Rather, use of the words "example" or "exemplary" is intended to present concepts in a concrete fashion. As used in this application, the term "or" is intended to mean an inclusive "or" rather than an exclusive "or". That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. In addition, the articles "a" and "an" as used in this application and the appended claims should generally be construed to mean "one or more" unless specified otherwise or clear from context to be directed to a singular form.

Computing devices typically include a variety of media, which can include computer-readable storage media and/or communications media, in which these two terms are used in this description differently from one another as follows. Computer-readable storage media can be any available storage media that can be accessed by the computer, is typically of a non-transitory nature, and can include both volatile and nonvolatile media, removable and non-removable media. By way of example, and not limitation, computer-readable storage media can be implemented in connection with any method or technology for storage of information such as computer-readable instructions, program modules, structured data, or unstructured data. Computer-readable storage media can include, but are not limited to, RAM, ROM, EEPROM, flash memory or other memory technology, CD-ROM, digital versatile disk (DVD) or other optical disk storage, magnetic cassettes, magnetic tape, magnetic disk storage or other magnetic storage devices, or other tangible and/or non-transitory media which can be used to store desired information. Computer-readable storage media can be accessed by one or more local or remote computing devices, e.g., via access requests, queries or other data retrieval protocols, for a variety of operations with respect to the information stored by the medium.

On the other hand, communications media typically embody computer-readable instructions, data structures, program modules or other structured or unstructured data in a data signal that can be transitory such as a modulated data signal, e.g., a carrier wave or other transport mechanism, and includes any information delivery or transport media. The term "modulated data signal" or signals refers to a signal that has one or more of its characteristics set or changed in such a manner as to encode information in one or more signals. By way of example, and not limitation, communication media include wired media, such as a wired network or direct-wired connection, and wireless media such as acoustic, RF, infrared and other wireless media.

In view of the exemplary systems described above, methodologies that may be implemented in accordance with the described subject matter will be better appreciated with reference to the flowcharts of the various figures. For simplicity of explanation, the methodologies are depicted and described as a series of acts. However, acts in accordance with this disclosure can occur in various orders and/or concurrently, and with other acts not presented and described in this disclosure. Furthermore, not all illustrated acts may be required to implement the methodologies in accordance with certain aspects of this disclosure. In addition, those skilled in the art will understand and appreciate that the methodologies could alternatively be represented as a series of interrelated states via a state diagram or events. Additionally, it should be appreciated that the methodologies disclosed in this disclosure are capable of being stored on an article of manufacture to facilitate transporting and transferring such methodologies to computing devices. The term article of manufacture, as used in this disclosure, is intended to encompass a computer program accessible from any computer-readable device or storage media.

What is claimed is:

1. A system, comprising:
   a processor; and
   a memory that stores executable instructions that, when executed by the processor, facilitate performance of operations, comprising:
     monitoring user adherence to a defined program followed by a plurality of users based on feedback information, associated with respective performances of the defined program by the plurality of users, received over a course of the defined program, wherein the feedback information comprises at least one of physical movement information related to the plurality of users, or physiological information related to the plurality of users;
     determining whether the plurality of users are deviating or are likely to deviate from requirements of the defined program based on the feedback information;
     generating respective reactions to be performed by respective avatars of the plurality of users, based on a determination that the plurality of users are deviating or are likely to deviate from the requirements of the defined program, to guide the plurality of users to adhere to the defined program, wherein the respective reactions are generated by employing machine learning techniques to analyze learned behaviors of the plurality of users, and wherein individual ones of the respective avatars are responsive to the feedback information from the plurality of users; and
     displaying the respective avatars of the plurality of users at a shared user interface generated and presented to the plurality of users at a device.

2. The system of claim 1, wherein the determining comprises comparison of at least one of feature values or context metrics associated with the feedback information, to at least one of reference metrics or reference value ranges associated with the defined program.

3. The system of claim 2, wherein the comparison of the at least one of feature values or context metrics involves rule-based classification schemes that relate the at least one of reference metrics or reference value ranges to the at least one of feature values or context metrics.

4. The system of claim 1, wherein the determining further comprises determining how the plurality of users are deviating or are likely to deviate from the requirements.

5. The system of claim 1, wherein the determining further comprises determining probability of an extent to which the plurality of users are deviating or are likely to deviate from the requirements.

6. The system of claim 1, wherein at least one reaction of the respective reactions comprises at least one of motion or movement, speech, tone of voice, level of sound, facial expressions, body language, color, speed of movement, or range of motion.

7. The system of claim 1, wherein at least one reaction of the respective reactions comprises provision of external data to at least one user of the plurality of users at the device, wherein the external data comprises at least documents, articles, multimedia, or hyperlinks.

8. A method, comprising:
   monitoring, by a system comprising a processor, user adherence to a defined program followed by a plurality of users based on feedback information, associated with respective performances of the defined program by the plurality of users, received over a course of the defined program, wherein the feedback information comprises at least one of physical movement information related to the plurality of users, or physiological information related to the plurality of users;
   determining, by the system, whether the plurality of users are deviating or are likely to deviate from requirements of the defined program based on the feedback information;
   generating, by the system, respective reactions to be performed by respective avatars of the plurality of users, based on a determination that the plurality of users are deviating or are likely to deviate from the requirements of the defined program, to guide the plurality of users to adhere to the defined program, wherein the respective reactions are generated by employing machine learning techniques to analyze learned behaviors of the plurality of users, and wherein individual ones of the respective avatars are responsive to the feedback information from the plurality of users; and displaying, by the system, the respective avatars of the plurality of users at a shared user interface generated and presented to the plurality of users at a device.

9. The method of claim 8, further comprising:
determining, by the system, probability of an extent to which the plurality of users are deviating or are likely to deviate from the requirements.

10. The method of claim 8, wherein at least one reaction of the respective reactions comprises at least one of motion or movement, speech, tone of voice, level of sound, facial expressions, body language, color, speed of movement, or range of motion.

11. The method of claim 8, wherein at least one reaction of the respective reactions further comprises provision of external data to at least one user of the plurality of users at the device, wherein the external data comprises at least documents, articles, multimedia, or hyperlinks.

12. A non-transitory machine-readable medium, comprising executable instructions that, when executed by a processor, facilitate performance of operations, comprising:
monitoring, by the processor, user adherence to a defined program followed by a plurality of users based on feedback information, associated with respective performances of the defined program by the plurality of users, received over a course of the defined program, wherein the feedback information comprises at least one of physical movement information related to the plurality of users, or physiological information related to the plurality of users;
determining, by the processor, whether the plurality of users are deviating or are likely to deviate from requirements of the defined program based on the feedback information;
generating, by the processor, respective reactions to be performed by respective avatars of the plurality of users, based on a determination that the plurality of users are deviating or are likely to deviate from the requirements of the defined program, to guide the plurality of users to adhere to the defined program, wherein the respective reactions are generated by employing machine learning techniques to analyze learned behaviors of the plurality of users, and wherein individual ones of the respective avatars are responsive to the feedback information from the plurality of users; and displaying, by the processor, the respective avatars of the plurality of users at a shared user interface generated and presented to the plurality of users at a device.

13. The non-transitory machine-readable medium of claim 12, wherein the operations further comprise:
comparing, by the processor, at least one of feature values or context metrics associated with the feedback information, to at least one of reference metrics or reference value ranges associated with the defined program.

14. The non-transitory machine-readable medium of claim 13, wherein the comparing of the at least one of feature values or context metrics involves rule-based classification schemes that relate the at least one of reference metrics or reference value ranges to the at least one of feature values or context metrics.

15. The non-transitory machine-readable medium of claim 12, wherein the operations further comprise:
determining, by the processor, how the plurality of users are deviating or are likely to deviate from the requirements; and
determining, by the processor, probability of an extent to which the plurality of users are deviating or are likely to deviate from the requirements.

16. The system of claim 1, wherein the shared user interface resembles a live group environment in which the plurality of users are present together and performing an activity.

17. The method of claim 8, wherein at least one reaction of the respective reactions comprises initiation of electronic communication to an entity associated with a user of the plurality of users.

18. The method of claim 8, wherein the electronic communication comprises sending a notification to the entity associated with the user.

19. The method of claim 8, wherein the shared user interface resembles a live group environment in which the plurality of users are present together and performing an activity.

20. The non-transitory machine-readable medium of claim 12, wherein the shared user interface resembles a live group environment in which the plurality of users are present together and performing an activity.

* * * * *